US012782362B2

(12) United States Patent
Li et al.

(10) Patent No.: US 12,782,362 B2
(45) Date of Patent: Nov. 3, 2026

(54) MULTIPLEXED DILEU-BIOTIN-AZIDE (DBA) TAG ENABLED ISOBARIC TANDEM ORTHOGONAL PROTEOLYSIS ACTIVITY-BASED PROTEIN PROFILING (isoBOP-ABPP) PLATFORM FOR HIGH-THROUGHPUT QUANTITATIVE PAN-PTM ANALYSIS

(71) Applicant: Wisconsin Alumni Research Foundation, Madison, WI (US)

(72) Inventors: Lingjun Li, Madison, WI (US); Miyang Li, Madison, WI (US); Min Ma, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 666 days.

(21) Appl. No.: 18/334,781

(22) Filed: Jun. 14, 2023

(65) Prior Publication Data

US 2024/0036055 A1 Feb. 1, 2024

Related U.S. Application Data

(60) Provisional application No. 63/352,510, filed on Jun. 15, 2022.

(51) Int. Cl.
*G01N 33/68* (2006.01)

(52) U.S. Cl.
CPC ..... *G01N 33/6848* (2013.01); *G01N 2440/00* (2013.01); *G01N 2458/15* (2013.01)

(58) Field of Classification Search
CPC ........... G01N 33/6848; G01N 2458/15; G01N 2440/00

(Continued)

(56) References Cited

U.S. PATENT DOCUMENTS 7,195,751 B2 3/2007 Pappin et al.
7,355,045 B2 4/2008 Dey et al.

(Continued)

FOREIGN PATENT DOCUMENTS

EP 2108654 10/2009
JP 2005-514404 5/2005

(Continued)

OTHER PUBLICATIONS

Trester-Zedlitz, M et al., Journal of the American Chemical Society 2003, 125, 2416-2425. (Year: 2003).*

(Continued)

*Primary Examiner* — Arlen Soderquist
(74) *Attorney, Agent, or Firm* — LEYDIG, VOIT & MAYER, LTD.

(57) ABSTRACT

The present invention provides improved cleavable biotin-containing isobaric tags for quantitative mass spectrometry proteomics, particularly useful in quantification of post-translational modifications (PTMs) and assessing cysteine containing proteins. The isobaric chemical tags, DiLeu-Biotin-Azide (DBA), consist of three "modules": (1) a DiLeu reporter group for relative quantification using MS/MS; (2) a biotin moiety for selective enrichment via streptavidin beads; and (3) an azide functional group to enable biorthogonal click chemistry. The DBA tags could be used in a high-throughput quantitative pan-PTM analysis platform.

8 Claims, 22 Drawing Sheets

Candidate A

Candidate C

Candidate B

Candidate D

Candidate E

(58) Field of Classification Search
USPC ............................................................ 436/86
See application file for complete search history.

(56) References Cited

U.S. PATENT DOCUMENTS

| | | | | |
|---|---|---|---|---|
| 7,732,378 | B2 | 6/2010 | Thompson et al. | |
| 7,816,304 | B2 | 10/2010 | Schmidt et al. | |
| 9,213,033 | B2 | 12/2015 | Grothe et al. | |
| 9,297,808 | B2 | 3/2016 | Louette et al. | |
| 9,377,469 | B2 | 6/2016 | Louette et al. | |
| 9,388,132 | B2 | 7/2016 | Li et al. | |
| 10,119,974 | B2 | 11/2018 | Li et al. | |
| 2002/0037532 | A1* | 3/2002 | Regnier | G01N 33/6851 435/7.1 |
| 2002/0150961 | A1* | 10/2002 | Bogyo | C07K 5/0215 435/23 |
| 2002/0164649 | A1* | 11/2002 | Singh | G01N 33/6851 435/7.1 |
| 2004/0038319 | A1* | 2/2004 | Aebersold | G01N 33/6803 435/7.5 |
| 2005/0037423 | A1* | 2/2005 | Lerchen | A61K 47/65 435/7.1 |
| 2005/0048489 | A1* | 3/2005 | Thompson | H01J 49/04 435/6.12 |
| 2005/0130235 | A1* | 6/2005 | Hsieh-Wilson | G01N 33/68 435/7.5 |
| 2006/0172319 | A1 | 8/2006 | Yan et al. | |
| 2006/0246530 | A1* | 11/2006 | Krause | G01N 33/6848 435/23 |
| 2008/0242838 | A1 | 10/2008 | Peters et al. | |
| 2008/0299595 | A1* | 12/2008 | Wong | G01N 33/582 435/70.1 |
| 2010/0029495 | A1* | 2/2010 | Schaefer | G01N 33/6851 506/13 |
| 2010/0129842 | A1 | 5/2010 | Pappin et al. | |
| 2010/0178710 | A1 | 7/2010 | Hamon et al. | |
| 2010/0190183 | A1* | 7/2010 | Hoffmann | G01N 33/6848 530/331 |
| 2010/0297250 | A1* | 11/2010 | Boons | C07K 2/00 548/304.1 |
| 2011/0165606 | A1* | 7/2011 | Tutturen | G01N 33/6842 548/304.1 |
| 2013/0035480 | A1* | 2/2013 | Steemers | C07D 495/04 536/25.4 |
| 2013/0078728 | A1 | 3/2013 | Li et al. | |
| 2014/0120565 | A1 | 5/2014 | Coon et al. | |
| 2015/0241437 | A1 | 8/2015 | Zhang et al. | |
| 2016/0258961 | A1 | 9/2016 | Thompson et al. | |
| 2018/0299464 | A1 | 10/2018 | Li et al. | |
| 2019/0225559 | A1 | 7/2019 | Li et al. | |
| 2021/0181206 | A1 | 6/2021 | Li et al. | |

FOREIGN PATENT DOCUMENTS

| | | |
|---|---|---|
| JP | 2009-503485 | 1/2009 |
| JP | 2009-526998 | 7/2009 |
| WO | WO 2004/086050 | 10/2004 |
| WO | WO 2008/005846 | 1/2008 |
| WO | WO 2010/008159 | 1/2010 |
| WO | WO 2010/104981 | 9/2010 |

OTHER PUBLICATIONS

Speers, A. E. et al., Journal of the American Chemical Society 2003, 125, 4686-4687 with 6 pages of supporting information. (Year: 2003).*

Lamos, S. M. et al., Angewandte Chemie International Edition 2006, 45, 4329 -4333. (Year: 2006).*

Li, S. et al., Chemical Communications 2007, 2181-2183 with 6 pages of supporting information. (Year: 2007).*

Dieterich, D. C. et al., Nature Protocols 2007, 2, 532-540. (Year: 2007).*

Zeng, D. et al., Bioorganic & Medicinal Chemistry Letters 2009, 19,2059-2061 with 5 pages of supplementary information. (Year: 2009).*

Geurink, P. P. et al., Angewandte Chemie International Edition 2010, 49, 6802-6805 with 30 pages of supporting information. (Year: 2010).*

Szychowski, J. et al., Journal of the American Chemical Society 2010, 132, 18351-18360 with 16 pages of supporting information. (Year: 2010).*

Martin, B. R. et al, Nature Methods 2012, 9, 84-89 with 2 pages of supplementary information. (Year: 2012).*

Bielski, R. et al, Chemical Reviews 2013, 113, 2205-2243. (Year: 2013).*

Bateman, L. A. et al, Journal of the American Chemical Society 2013, 135, 14568-14573 with 7 pages of supporting information. (Year: 2013).*

Yuan, W. et al., Chemical Communications 2013, 49, 11080-11082 with 9 pages of supplementary information. (Year: 2013).*

Chuh, K. N. et al., Current Opinion in Chemical Biology 2015, 24, 27-37. (Year: 2015).*

Wang, J. et al., Scientific Reports 2015, 5, Article 7896, 12 pages. (Year: 2015).*

Thinon, E. et al., Biochemical Society Transactions 2015, 43, 253-261. (Year: 2015).*

Wright, M. H. et al., Natural Product Reports 2016, 33, 681-708. (Year: 2016).*

Elliott, T. S. et al., Cell Chemical Biology 2016, 23, 805-815 with 43 pages of supplemental information. (Year: 2016).*

Woo, C. M. et al., Analytical and Bioanalytical Chemistry 2017, 409, 579-588 with 21 pages of supplementary material. (Year: 2017).*

Qin, K. et al., ACS Chemical Biology 2018, 13, 1983-1989 with 35 pages of supporting information. (Year: 2018).*

Rabalski, A. J. et al., ACS Chemical Biology 2019, 14, 1940-1950. (Year: 2019).*

Wijetunge, A. N. et al., Bioconjugate Chemistry 2021, 32, 254-258 with 34 pages of supporting information. (Year: 2021).*

Conway, L. P. et al., Chemical Science 2021, 12, 7839-7847 with 63 pages of supplementary materials. (Year: 2021).*

Li, Z. et al., Analytical Chemistry 2022, 94, 3074-3081 with 12 pages of supporting information. (Year: 2022).*

Li, Z. et al., Journal of Proteome Research 2022, 21, 1349-1358 with 22 pages of supporting information. (Year: 2022).*

"Hydrazines," IUPAC. Compendium of Chemical Terminology, 2nd ed. (the "Gold Book"). Compiled by A. D. Mc Naught and A. Wilkinson. Blackwell Scientific Publications, Oxford ( 1997). https://doi.org/10.1351 /goldbook. H02881 (Year: 1997).

Abrams et al. (2011) "S-Nitrosylation of ApoE in Alzheimer's Disease," Biochemistry 50, 3405-3407.

Akter et al. (2015) "DYn-2 Based Identification of *Arabidopsis* Sulfenomes," Molecular & Cellular Proteomics 14.5.

Akter et al. (2018) "Chemical proteomics reveals new targets of cysteine sulfinic acid reductase," Nature Chemical Biology 14, 995-1004.

Albericio et al. (1998) "Use of Onium Salt-Based Coupling Reagents in Peptide Synthesis," J. Org. Chem. 63:9678-9683.

Alcock et al. (2018) "Chemical methods for mapping cysteine oxidation," Chemical Society Reviews 47, 231-268.

Alley et al., "High-sensitivity Analytical Approaches for the StructuralCharacterization of Glycoproteins", Chem. Rev., 113(4): 2668-2732 (2013).

Altelaar et al. (2013) "Next-generation proteomics: towards an integrative view of proteome dynamics," Nature Reviews Genetics 14, 35-48.

An et al., "Glycomics and disease markers", Curr. Opin. Chem. Biol., 13 (5-6):601-607 (2009).

Anumula et al., "Advances in fluorescence derivatization methods for high-performance liquid chromatographic analysis of glycoprotein carbohydrates", Anal. Biochem., 350(1): 1-23 (2006).

Anumula et al., "High resolution and high sensitivity methods for oligosaccharide mapping and characterization by normal phase high

(56) References Cited

OTHER PUBLICATIONS performance liquid chromatography following derivatization with highly fluorescent anthranilic acid", Gtvcobiologv, 8(7): 685-694 (1998).
Anumula, "Quantitative Determination of Monosaccharides in Glycoproteins by High-Performance Liquid Chromatography with Highly Sensitive Fluorescence Detection," Anal. Biochem., 220(2): 275-283 (1994).
Applied Biosystems (2004) Applied Biosystems iTRAQ™ Reagents Chemistry Reference Guide.
Araki et al. (2016) "Redox Sensitivities of Global Cellular Cysteine Residues under Reductive and Oxidative Stress," Journal of Proteome Research 15, 2548-2559.
Arnold et al., "Evaluation of the serum N-linked glycome for the diagnosis of cancer and chronic inflammation", Proteomics, 8 (16): 3284-3293 (2008).
Atwood et al., "Quantitation by Isobaric Labeling: Applications to Glycomics", J.Proteome Res., 7(1): 367-374 (2008).
Aye et al., "Selectivity in Enrichment of cAMP-dependent Protein KinaseRegulatory Subunits Type I and Type II and Their Interactors Using Modified CAMP Affinity Resins", Mo/. Cell. Proteomics, 8(5):1016-1028 (2009).
Backus et al. (2016) "Proteome-wide covalent ligand discovery in native biological systems," Nature 534, 570-574 with 17 pages of Supplementary material.
Bak et al. (2018) "A Quantitative Chemoproteomic Platform to Monitor Selenocysteine Reactivity within a Complex Proteome," Cell Chemical Biology 25, 1157-1167.
Bantscheff et al. (2007) "Quantitative mass spectrometry in proteomics: a critical review," Analytical and Bioanalytical Chemistry 389, 1017-1031.
Bar-Peled et al. (2017) "Chemical Proteomics Identifies Druggable Vulnerabilities in a Genetically Defined Cancer," Cell 171, 696-709.
Bateman et al. (2018) "An Alkyne-Aspirin Chemical Reporter for the Detection of Aspirin-Dependent Protein Modification in Living Cells," J. Am. Chem Soc 135, 14568-14573.
Bicker et al. (2012) "Seeing Citrulline: Development of a Phenylglyoxal-Based Probe to Visualize Protein Citrullination" J. Am. Chem. Soc 134(41): pp. 17015-17018.
Bigge et al. "Nonselective and Efficient Fluorescent Labeling of Glycans Using 2-Amino Benzamide and AnthranilicAcid", Anal. Biochem., 230(2): 229-238 (1995).
Boehm et al. (2007) "Precise Protein Quantification Based on Peptide Quantification Using iTRAQ™," BMC Bioinformatics 8(214):1-18.
Boersema et al. (2009) "Multiplex Peptide Stable Isotope Dimethyl Labeling forQuantitative Proteomics," Nature Protocols 4(4):484-494.
Boersema et al., "Triplex protein quantification based on stable isotope labeling by peptide dimethylation applied to cell and tissue lysates", Proteomics, 8:4624-4632 (2008).
Bork et al., "Increasing the sialylation of therapeutic glycoproteins: The potential of the sialic acid biosynthetic pathway", J. Pharm Sci., 98 (10): 3499-3508 (2009).
Bowman, M.J. et al. "Tags for the Stable Isotopic Labeling of Carbohydrates and Quantitative Analysis by Mass Spectrometry," Anal . Chem. 2007, 79, 5777-5784 (Year: 2007).
Bulaj et al. (1998) "Ionization-reactivity relationships for cysteine thiols in polypeptides," Biochemistry 37, 8965-8972.
Burlet et al. (1993) "Decompositions of cationized heterodimers of amino acids in relation to charge location in peptide ions," J Am Soc Mass Spectrom 4(6):461-469.
Carpino et al. (1995) "Tetramethylfluoroformamidinium Hexafluorophosphate: ARapid-Acting Peptide Coupling Reagent for Solution and Solid Phase Peptide Synthesis," J. Am. Chem. Soc. 117:5401-5402.
Castro et al. (2015) "A systematic review of observational studies on oxidative/nitrosative stress involvement in dengue pathogenesis," Colomb Med (Cali) 46, 135-143.
Chaiyawat et al. (2014) "Aberrant O-GlcNAcylated proteins: new perspectives in breast and colorectal cancer," Frontiers in Endocrinology 5, 193, 1-10.
Chakrabarty et al. (2019) "Recent Advances in Activity-Based Protein Profiling of Proteases," Activity-Based Protein Profiling 420, 253-281.
Chakravarti et al. (2010) "GAPDH regulates cellular heme insertion into inducible nitric oxide synthase," Proceedings of the National Academy of Sciences of the United States of America 107, 18004-18009.
Chen et al. (2013) "Methods for detection and characterization of protein S-nitrosylation," Methods 62, 138-150.
Chen et al. (2017) "Target identification with quantitative activity based protein profiling (ABPP)," Proteomics, 17, 1600212.
Chen et al. (Apr. 2017) "Chemoproteomic profiling of targets of lipid-derived electrophiles by bioorthogonal aminooxy probe," Redox Biology 12, 712-718.
Chen et al., "Quantitative Glycomic Analysis by Mass-Defect-Based Dimethyl Pyrimidinyl Ornithine (DiPyrO) Tags and High-Resolution Mass Spectrometry", Anal. Chem., 90 (13): 7817-7823 (May 2018).
Chio et al. (2020) "Click Chemistry Conjugations," Antibody-Drug Conjugates: Methods and Protocols 2078, 83-97.
Choe et al. (Sep. 19, 2007) "8-Plex quantitation of changes in cerebrospinal fluid protein expression in subjects undergoing intravenous immunoglobulintreatment for Alzheimer's disease," Proteomics. 7(20): 3651-3660.
Chung et al. (2004) "S-nitrosylation of Parkin regulates ubiquitination and compromises Parkin's protective function," Science 304, 1328-1331.
Cioce et al. (Apr. 2021) "Optimization of Metabolic Oligosaccharide Engineering with Ac4GalNAlk and Ac4GlcNAlk by an Engineered Pyrophosphorylase," ACS Chem. Biol. 16, 10, 1961-1967.
Clancy, K.W et al. "Detection and identification of protein citrullination in complex biological systems," Current Opinion in Chemical Biology 2016, 30:1-6. (Year: 2016).
Collins et al. (2004) "Finishing the euchromatic sequence of the human genome," Nature 431, 931-945.
Coste et al. (1994) "Coupling N-Methylated Amino Acids Using PyBroP1 and PyCioP Halogenophosphonium Salts: Mechanism and Fields of Application," J. Org.Chem. 59:2437-2446.
Craft et al. (2013) "Recent advances in quantitative neuroproteomics," Methods 61, 186-218.
Dayon et al. (2008) "Relative Quantification of Proteins in Human CerebrospinalFluids by MS/MS Using 6-Piex Isobaric Tags," Anal. Chem. 80:2921-2931.
Defaus et al., "Mammalian protein glycosylation—structure versus function," Analyst, 139(12): 2944-2967 (2014).
Deng et al. (2013) "Proteome-wide Quantification and Characterization of Oxidation-Sensitive Cysteines in Pathogenic Bacteria," Cell Host & Microbe 13, 358-370.
Deng et al. (2020) "Activity-based protein profiling: Recent advances in medicinal chemistry," European Journal of Medicinal Chemistry 191, 112151.
Dikler et al., "Improving mass spectrometric sequencing of arginine-containing peptides by derivatization with acetylacetone", *J. Mass Spectrom.,* 32(12):1337-1349 (1997).
Dixon et al. (2009) "Identifying druggable disease-modifying gene products," Current Opinion in Chemical Biology 13, 549-555.
Dongre et al., "Influence of peptide composition, gas-phase basicity, and chemical modification on fragmentation efficiency: Evidence for the mobile proton model", *J. Am. Chem. Soc,* 118: 8365-8374 (1996).
Dwek, "Glycobiology: Toward Understanding the Function of Sugars", Chem.Rev., 96(2): 683-720 (1996).
Dwivedi et al. (2017) "Citrullination and Neutrophil Extracellular Traps" ProteinDeimination in Human Health and Disease, pp. 137-159.
Elkon, Keith B. (2013) "Poking Holes in Rheumatoid Joints" Sci. Transl. Med5(2019) pp. 209fs39.

(56) References Cited

OTHER PUBLICATIONS

Esbroeck et al. (2017) "Activity-based protein profiling reveals off-target proteins of the FAAH inhibitor BIA 10-2474," Science 356, 1084-1087.
Evangelista et al., "Acid-catalyzed reductive amination of aldoses with 8-aminopyrene-1 ,3,6-trisulfonate", Electro{)horesis, 17(2): 347-51 (1996).
Evans et al. (2006) "Mechanism-based profiling of enzyme families," Chemical Reviews 106, 3279-3301.
Fagan et al. (2009) "Decreased Cerebrospinal Fluid A beta(42) Correlates with Brain Atrophy in Cognitively Normal Elderly," Annals of Neurology 65, 176-183.
Fagan et al. (Nov. 2009) "Cerebrospinal fluid tau and ptau(181) increase with cortical amyloid deposition in cognitively normal individuals: Implications for future clinical trials of Alzheimer's disease," Embo Molecular Medicine 1, 371-380.
Falb et al. (1999) "In situ Generation of Fmoc-Amino Acid Chlorides Using bis-(trichloro-methyl)carbonate and Its Utilization for Difficult Couplings in Solid-Phase Peptide Synthesis," J. Peptide Res. 53:507-517.
Fantoni et al. (Jan. 2021) "A Hitchhiker's Guide to Click-Chemistry with Nucleic Acids," Chem Rev. 121 12:7122-7154.
Fauq et al. (2006) "Synthesis of acid-cleavable light isotope-coded affinity tags (ICAT-L) for potential use in proteomic expression profiling analysis," Bioconjugate Chemistry 17, 248-254.
Fedorova et al. (2014) "Protein carbonylation as a major hallmark of oxidative damage: Update of analytical strategies," Mass Spectrometry Reviews 33, 79-97.
Feng et al. (2019) "Isobaric Multiplex Labeling Reagents for Carbonyl- Containing Compound (SUGAR) Tags: A Probe for Quantitative Glycomic Analysis," Analytical Chemistry 91, 3141-3146.
Feng et al. (2019) "Multiplex Quantitative Glycomics Enabled by Periodate Oxidation and Triplex Mass Defect Isobaric Multiplex Reagents for Carbonyl-Containing Compound Tags," Analytical Chemistry 91, 11932-11937.
Fert-Bober et al. (2015) "Citrullination of myofilament proteins in heart failure" Cardiovascular Research 108(2): pp. 232-242.
Fert-Bober et al. (2019) "Mapping Citrullinated Sites in Multiple Organs of MiceUsing Hypercitrullinated Library" J Proteome Res. 18(5): pp. 2270-2278.
Ficarro et al. (2002) "Phosphoproteome analysis by mass spectrometry and its application to *Saccharomyces cerevisiae,*" Nature Biotechnology 20, 301-305.
Filipovic et al. (2017) "Oxidative and nitrosative stress pathways in the brain of socially isolated adult male rats demonstrating depressive- and anxiety-like symptoms," Brain Struct Funct 222, 1-20.
Foettinger et al., "Derivatisation of arginine residues with malondialdehyde for the analysis of peptides and protein digests by LC-ESI-MS/MS", *J. Mass Spectrom.,* 41: 623-632. (2006).
Fonovic et al. (2007) "Proteomics evaluation of chemically cleavable activity-based probes," Molecular & Cellular Proteomics 6, 1761-1770.
Forrester et al. (2007) "Assessment and application of the biotin switch technique for examining protein S-nitrosylation under conditions of pharmacologically induced oxidative stress," Journal of Biological Chemistry 282, 13977-13983.
Frost et al. (2015) "High-Resolution Enabled 12-Plex Dileu Isobaric Tags forQuantitative Proteomics" Anal. Chem., 87(3): pp. 1646-1654.
Frost et al. (2017) "Mass Defect-Based Dimethyl Pyrimidinyl Ornithine (DiPyrO) Tags for Multiplex Quantitative Proteomics," Anal. Chem. 89(20): 10798-10805.
Frost et al. (May 2020) "21-plex Dileu Isobaric Tags for High-ThroughputQuantitative Proteomics" Anal. Chem. 92(12): pp. 8228-8234.
Frost et al., "Development and characterization of novel 8-plex DiLeu isobariclabels for quantitative proteomics and peptidomics", Rapid Commun. Mass S{)ectrom, 29 (12): 1115-1124 (2015).
Gaynon et al., "Long-term results of the children's cancer group studies for childhood acute lymphoblastic leukemia 1983-2002: A Children's Oncology Group Report", Leukemia, 24(2): 285-297 (2010).
Geurink et al. (2010) "A Cleavable Linker Based on the Levulinoyl Ester for Activity-Based Protein Profiling," Angewandte Chemie-International Edition 49, 6802-6805.
Giron et al. (2011) "Cysteine tagging for MS-based proteomics," Mass Spectrometry Reviews 30, 366-395.
Glenner et al. (1984) "Alzheimer's disease: Initial report of the purification and characterization of a novel cerebrovascular amyloid protein," Biochemical and Biophysical Research Communications), vol. 120, p. 885-890.
Goedert (2015) "Alzheimer's and Parkinson's diseases: The prion concept in relation to assembled A beta, tau, and alpha-synuclein," Science 349.
Goshe, M.B et al. "Phosphoprotein Isotope-Coded Affinity Tag Approach for Isolating and Quantitating Phosphopeptides in Proteome-Wide Analyses," Anal. Chem. 2001, 73, 2578-2586 (Year: 2001).
Greer, "Novel isotopic N,N-dimethyl leucine (iDiLeu) reagents enable absolute quantification of peptides and proteins using a standard curve approach", J. Am. Soc. Mass. Spectrom., 26:107-119 (2015).
Gu et al. (2016) "High-throughput endogenous measurement of S-nitrosylation in Alzheimer's disease using oxidized cysteine-selective cPILOT," Analyst 141, 3904-3915.
Gu et al. (2016) "Proteomic approaches to quantify cysteine reversible modifications in aging and neurodegenerative diseases," Proteomics Clinical Applications 10, 1159-1177.
Guo et al. (2007) "Stable-Isotope Dimethylation Labeling Combined with LC-ESI MS for Quantification of Amine-Containing Metabolites in Biological Samples," Anal.Chem. 79:8631-8638.
Guo et al. (2009) "Stereospecific Synthesis of Conformationally Constrained y-Amino Acids: New Foldamer Building Blocks That Support Helical Secondary Structure," J. Am. Chem. Soc 131:16018-16020.
Gurbuz et al. (2014) "LC-MS investigations on interactions between isolated [beta]-lactoglobulin peptides and lipid oxidation product malondi," Food Chemistry, Elsevier Ltd 175: 300-305.
Gygi et al. (1999) "Quantitative Analysis of Complex Protein Mixtures UsingIsotope-Coded Affinity Tags," Nature Biotechnology. 17:994-999.
Hacker et al. (2017) "Global profiling of lysine reactivity and ligandability in the human proteome," Nat Chem. 9, 1181-1190.
Hahne et al., "Carbonyl-Reactive Tandem Mass Tags for the Proteome-Wide Quantification of N-Linked Glycans", Anal. Chem., 84 (8): 3716-3724 (2012).
Hansen et al. (2003) "Mass Spectrometric Analysis of Protein Mixtures at LowLevels Using Cleavable 13C-Isotope-Coded Affinity Tag and Multidimensional Chromatography," Mol. Cell. Proteomics 2:299-314.
Hao et al. (2015) "Relative quantification of amine-containing metabolites using isobaric N, N-dimethyl leucine (DiLeu) reagents via LC-ESI-MS/MS and CE-ESI-MS/MS," Analyst 140, 467-475.
Hebert et al., "Amine-reactive Neutron-encoded Labels for Highly Proteomic Quantitation", *Mol. Cell Proteomeics,* 12:3360-3369 (2013).
Hebert et al., "FTMS enabled neturon-encoded chemical tags: 4, 12, and 36 plexes," Presentation, pp. 1-79 (2013).
Hebert et al., "Neutron-encoded mass signatures for multiplexed proteome quantification", *Nat. Meth.,* 10:332-334 (2013).
Heinrich et al. (2013) "Biological nitric oxide signalling: chemistry and terminology," British Journal of Pharmacology 169, 1417-1429.
Hems et al. (2018) "CuAAC click chemistry for the enhanced detection of novel alkyne-based natural product toxins," Chemical Communications 54, 12234-12237.
Hess et al. (2005) "Protein S-nitrosylation: Purview and parameters," Nature Reviews Molecular Cell Biology 6, 150-166.
Hitchcock et al., "Comparative glycomics of connective tissueglycosaminoglycans", Proteomics, 8 (7): 1384-1397 (2008).
Holm et al. (2006) "Specific modification of peptide-bound citrulline residues" Anal Biochem. 352(1): pp. 68-76.

(56) References Cited

OTHER PUBLICATIONS

Holmberg et al. (2005) "The biotin-streptavidin interaction can be reversibly broken using water at elevated temperatures," Electrophoresis 26, 501-510.
Hsu et al. (2003) "Stable-Isotope Dimethyl Labeling for Quantitative Proteomics," Anal. Chem. 75:6843-6852.
Hsu et al. (2006) "Dimethyl Multiplexed Labeling Combined with MicrocolumnSeparation and MS Analysis for Time Course Study in Proteomics," Electrophoresis. 27:3652-3660.
Huang et al. (2006) "Quantitation of Protein Phosphorylation in Pregnant Rat Uteri Using Stable Isotope Dimethyl Labeling Coupled with IMAC," Proteomics 6:1722-1734.
Huang et al. (2019) "Global Portrait of Protein Targets of Metabolites of the Neurotoxic Compound BIA 10-2474," ACS Chemical Biology 14, 192-197.
Hyman et al. (1997)"Editorial on consensus recommendations for the postmortem diagnosis of Alzheimer disease from the National Institute on Aging and the Reagan Institute working group on diagnostic criteria for the neuropathological assessment of Alzheimer disease," Journal of Neuropathology and Experimental Neurology 56, 1095-1097.
Hyre et al. (2002) "Early mechanistic events in biotin dissociation from streptavidin," Nature Structural Biology 9, 582-585.
Jaffrey et al. (2001) "Protein S-nitrosylation: a physiological signal for neuronal nitric oxide," Nature Cell Biology 3, 193-197.
Jensen (2004) "Modification-specific proteomics: characterization of post- translational modifications by mass spectrometry," Current Opinion in Chemical Biology 8, 33-41.
Ji et al. (2005) "Differential Dimethyl Labeling of N-Termini of Peptides AfterGuanidination for Proteome Analysis," J. Proteome Research 4:2099-2108.
Ji et al. (2005) "Identification and Quantification of Differentially Expressed Proteins in E-Cadherin Deficient SCC9 Cells and SCC9 Transfectants Expressing E-Cadherin by Dimethyl Isotope Labeling, LC-MALDI MS and MS/MS," J. Proteome Research 4:1419-1426.
Ji et al. (2005) "Quantitative Proteome Analysis Using Differential Stable IsotopicLabeling and Microbore LC-MALDI MS and MS/MS," J. Proteome Research 4:734-742.
Ji et al. (2006) "Effect of 2MEGA Labeling on Membrane Proteome Analysis UsingLC-ESI QTOF MS," J. Proteome Research 5:2567-2576.
Ji et al. (2007) "A Study of Reproducibility of Guanidination-Dimethylation Labelingand Liquid Chromatography Matrix-Assisted Laser Desorption Ionization Mass Spectrometry for Relative Proteome Quantification," Anal. Chim. Acta 585:219-226.
Jacob et al. (2003) "Sulfur and Selenium: The Role of Oxidation State in Protein Structure and Function," AngewChem Int Ed Engl. 42, 4742-4758.
Kaatsch et al., "Epidemiology of childhood cancer", Cancer Treat. Rev., 36 (4):277-285 (2010).
Kaminski, Z.J. et al. "Mild and Efficient Synthesis of Carboxylic Acid Anhydrides from Carboxylic Acids and Triazine Coupling Reagents," Synthetic Communications vol. 34, No. 18, pp. 3349-3358, 2004 (Year: 2004).
Khidekel et al. (2007) "Probing the Dynamics of 0-GicNAc Glycosylation in theBrain Using Quantitative Proteomics," Nat. Chem. Bioi. 3(6):339-348.
Krawczuk-Rybak et al., "Intellectual functioning of childhood leukemiasurvivors—relation to Tau protein—a marker of white matter injury", Adv. Med. Sci., 57(2): 266-72 (2012).
Kuljanin et al. (Jan. 2021) "Reimagining high-throughput profiling of reactive cysteines for cell-based screening of large electrophile libraries," Nat Biotechnol. 39, 630-641.
Kunieda et al. (2018) "Development of a fluorescent probe for detection of citrulline based on photo-induced electron transfer" Bioorg Med Chem Lett,28(5): pp. 969-973.
Kuyama et al., "An improved method for de novo sequencing of arginine-containing, Nalphatris (2,4,6-trimethoxyphenyl) phosphonium-acetylated peptides", *Rapid Commun. Mass Spectrom.,* 22: 2063-2072 (2008).
Lange et al. (2008) "Selected reaction monitoring for quantitative proteomics: a tutorial," Molecular Systems Biology 4.
Larsen et al. (2005) "Highly selective enrichment of phosphorylated peptides from peptide mixtures using titanium dioxide microcolumns," Molecular & Cellular Proteomics 4, 873-886.
Leitner et al., "Effects of an arginine-selective tagging procedure on the fragmentation behavior of peptides studied by electrospray ionization tandem mass spectrometry (ESI-MS/MS," *Anal. Chim. Acta.,* 528: 165-173 (2005).
Leitner et al., "Improving fragmentation of poorly fragmenting peptides and phosphopeptides during collision-induced dissociation by malondialdehyde modification of arginine residues", *J. Mass Spectrom.,* 42: 950-959 (2007).
Leitner et al., "Probing of arginine residues in peptides and proteins using selective tagging and electrospray ionization mass spectrometry", *J. Mass Spectrom.,* 38: 891-899 (2003).
Lemeer et al. (2008) "Comparative Phosphoproteomics of Zebrafish Fyn/YesMorpholino Knockdown Embryos," Mol. Cell. Proteomics 7:2176-2187.
Lewallen et al. (2015) "Chemical Proteomic Platform to Identify Citrullinated Proteins," Acs Chemical Biology 10, 2520-2528.
Li et al. (2003) "Protein Profiling with Cleavable Isotope-Coded Affinity Tag (ciCAT)Reagents," Mol. Cell. Proteomics 2:1198-1204.
Li et al. (Apr. 2022) "Benchmarking Cleavable Biotin Tags for Peptide-Centric Chemoproteomics," Proteome Res. 21, 5, 1349-1358. DOI: 10.1021/acs.jproteome.2c00174.
Li et al. (Mar. 2020) "TMTpro reagents: a set of isobaric labeling mass tags enables simultaneous proteome-wide measurements across 16 samples," Nature Methods 17, 399-404 with 2 pages of Methods.
Lima et al. (2010) "S-Nitrosylation in Cardiovascular Signaling," Circulation Research 106, 633-646.
Lo Conte et al. (2013) "The Redox Biochemistry of Protein Sulfenylation and Sulfinylation," Journal of Biological Chemistry 288, 26480-26488.
Lopez-Sanchez et al. (2009) "Unraveling the S-nitrosoproteome: Tools and strategies," Proteomics 9, 808-818.
Ishigami et al. (2005) "Abnormal accumulation of citrullinated proteins catalyzedby peptidylarginine deiminase in hippocampal extracts from patients with Alzheimer's disease" Journal of Neuroscience Research 80(1): pp. 120-128.
Lu et al. (2011) "Bioinformatic Analysis and Post-Translational Modification Crosstalk Prediction of Lysine Acetylation," Plos One 6.
Maes et al. (1993) "Significantly increased expression of T-cell activation markers (interleukin-2 and HLA-DR) in depression: further evidence for an inflammatory process during that illness," Prog Neuropsychopharmacol Biol Psychiatry 17, 241-255.
Marletta et al. (1998) "Catalysis by nitric oxide synthase," Current Opinion in Chemical Biology 2, 656-663.
Martin et al. (2011) "Post-translational modifications of tau protein: Implications for Alzheimer's disease," Neurochemistry International 58, 458-471.
Masters et al. (1985) "Amyloid plaque core protein in Alzheimer disease and Down syndrome," Proceedings of the National Academy of Sciences of the United States of America 82, 4245-4249.
McAlister et al., "MultiNotch MS3 Enables Accurate, Sensitive, and Multiplexed Detection of Differential Expression across Cancer Cell Line Proteomes" *Anal. Chem.,* 86(14):7150-7158 (2014).
Mcclatchy et al., "15N Metabolic Labeling of Mammalian Tissue with Slow Protein Turnover", *J. Proteome Res.,* 6:2005-2010 (2007).
Medina-Cleghorn et al. (2015) "Mapping Proteome-Wide Targets of Environmental Chemicals Using Reactivity-Based Chemoproteomic Platforms," Chemistry & Biology 22, 1394-1405.
Meldal et al. (2020) "Recent Fascinating Aspects of the CuAAC Click Reaction," Trends in Chemistry 2, 569-584.
Merrifield (1963) "Solid Phase Peptide Synthesis. I. The Synthesis of aTetrapeptide," J. Am. Chem. Soc 85:2149-2154.

(56) References Cited

OTHER PUBLICATIONS

Merrill et al., "NeuCode labels for relative protein quantification", *Mol. Cell Proteomics,* 13:2503-2512 (2014).
Mertins et al. (2013) "Integrated proteomic analysis of post-translational modifications by serial enrichment," Nature Methods 10, 634-637 with 3 pages of Methods.
Miseta et al. (2000) "Relationship between the occurrence of cysteine in proteins and the complexity of organisms," Molecular Biology and Evolution 17, 1232-1239.
Mnatsakanyan et al. (2019) "Proteome-wide detection of S-nitrosylation targets and motifs using bioorthogonal cleavable-linker-based enrichment and switch technique," Nature Communications 10.
Mocciaro et al. (2012) "Emerging regulatory mechanisms in ubiquitin-dependent cell cycle control," Journal of Cell Science 125, 255-263.
Moellering et al. (2012) "How Chemoproteomics Can Enable Drug Discovery and Development," Chemistry & Biology 19, 11-22.
Molina et al., "Temporal profiling of the adipocyte proteome during differentiation using a five-plex SILAC based strategy", *J. Proteome Res.,* 8: 48-58 (2009).
Morano et al. (2008) "Multiple Isotopic Labels for Quantitative MassSpectrometry," Anal. Chem. 80:9298-9309.
Moremen et al., "Vertebrate protein glycosylation: diversity, synthesis and function", Nat. Rev. Mo/. Cell Biol., 13 (7): 448-462 (2012).
Morino et al. (2005) "Reduced mitochondrial density and increased IRS-1 serine phosphorylation in muscle of insulin-resistant off-spring of type 2 diabetic parents," Journal of Clinical Investigation 115, 3587-3593.
Morris et al., "Studies towards the complete sequence determination of proteins by mass spectrometry: Derivatisation of methionine, cysteine and arginine containing peptides," *Biochem. and Biophys. Res. Comm.,* 51: 247-255. (1973).
Moskovitz (2014) "Detection and Localization of Methionine Sulfoxide Residues of Specific Proteins in Brain Tissue," Protein and Peptide Letters 21, 52-55.
Murray, C.I. et al. (2012) "Identification and Quantification of S-Nitrosylation by Cysteine Reactive Tandem Mass Tag Switch Assay," Mol. Cell. Proteomics 11(2): M111.013441 (Year: 2012).
Nakamura et al. (2015) "Aberrant protein S-nitrosylation contributes to the pathophysiology of neurodegenerative diseases," Neurobiology of Disease 84, 99-108.
Nakamura et al. (Jan. 2013) "Emerging Role of Protein-Protein Transnitrosylation in Cell Signaling Pathways," Antioxidants & Redox Signaling 18, 239-249.
Nakamura et al. (May 2013) "Aberrant Protein S-Nitrosylation in Neurodegenerative Diseases," Neuron 78, 596-614.
Neckers et al. (1971) "Developmental photochemistry. The Norrish Type II reaction," Journal of Organic Chemistry 36, 1838-1840.
Nemmara et al. (2019) "Development of Activity-Based Proteomic Probes for Protein Citrullination," Activity-Based Protein Profiling 420, 233-251.
Nie et al. (2016) "An optimization of the LC-MS/MS workflow for deep proteome profiling on an Orbitrap Fusion," Analytical Methods 8, 425-434.
Noort et al. (2006) "Verification of Exposure to Organophosphates: Generic Mass Spectrometric Method for Detection of Human Butyrylcholinesterase Adducts," Anal. Chem. 78, 18, 6640-6644.
Norton et al., "N-linked glycosylation of the liver cancer biomarker GP73", J.Cell Biochem., 104(1): 136-149 (2008).
Nunez et al. (2017) "iTRAQ-Based Shotgun Proteomics Approach for Relative Protein Quantification," In Multiplex Biomarker Techniques: Methods and Applications (Guest, P. C., ed) vol. 1546 pp. 267-274.
Oda et al., "Accurate quantitation of protein expression and site-specific phosphorylation", *Proc. Natl. Acad. Sci.,* 96: 6591-6596, Rockefeller University, New York, USA (Jun. 1999).
Ong et al. (2002) "Stable Isotope Labeling by Amino Acids in Cell Culture, SILAC, as a Simple and Accurate Approach to Expression Proteomics," Mol. Cell.Proteomics 1:376-386.
Ong et al. (2005) "Mass Spectrometry-Based Proteomics Turns Quantitative," Nat.Chem. Biol. 1 (5):252-262.
Onofrejova et al., "Malondialdehyde tagging improves the analysis of arginine oligomers and arginine-containing dendrimers by HPLC-MS", *J. Sep. Sci.,* 31: 499-506 (2008).
Ovaa et al. (2003) "Chemistry in living cells: Detection of active proteasomes by a two-step labeling strategy," Angewandte Chemie-International Edition 42, 3626-3629.
Ow et al. (2009) "iTRAQ Underestimation in Simple and Complex Mixtures: 'TheGood, the Bad and the Ugly'," J. Proteome Research 8:5347-5355.
Paige et al. (2008) "Nitrosothiol Reactivity Profiling Identifies S-Nitrosylated Proteins with Unexpected Stability," Chemistry & Biology, 15, 1307-1316.
Pan et al., "Single peptide-based protein identification in human proteome through MALDI-TOF MS coupled with amino acids coded mass tagging", *Anal. Chem.,* 75: 1316-1324 (2003).
Parker et al. (2017) "Ligand and Target Discovery by Fragment-Based Screening in Human Cells," Cell 168, 527-541.
Parker et al. (2020) "Click Chemistry in Proteomic Investigations," Cell. 180 605-632.
Paulick et al. (2008) "Application of activity-based probes to the study of enzymes involved in cancer progression," Current Opinion in Genetics & Development 18, 97-106.
Pedowitz et al. (2020) "Metabolic labeling for the visualization and identification of potentially O-GlcNAc modified proteins," Curr Protoc Chem Biol. 12(2): e81.
Petritis et al. (2000) "Parameter optimization for the analysis of underivatized protein amino acids by liquid chromatography and ionspray tandem mass spectrometry," Journal of Chromatography A 896, 253-263.
Polanco et al. (2018) "Amyloid-beta and tau complexity—towards improved biomarkers and targeted therapies," Nature Reviews Neurology 14, 22-39.
Qu et al. (2011) "S-Nitrosylation activates Cdk5 and contributes to synaptic spine loss induced by beta-amyloid peptide," Proceedings of the National Academy of Sciences of the United States of America 108, 14330-14335.
Qu et al. (2012)"S-nitrosylation of Cdk5 Potential implications in amyloid-beta-related neurotoxicity in Alzheimer disease," Prion 6, 364-370.
Qu et al. (2014) "Proteomic Quantification and Site-Mapping of S-Nitrosylated Proteins Using Isobaric iodoTMT Reagents," Journal of Proteome Research 13, 3200-3211.
Rahman, et al., "Filter-Aided N-Glycan Separation (FANGS): A ConvenientSample Preparation Method for Mass Spectrometric N-Glycan Profiling", J Proteome Res, 13 (3): 1167-1176 (2014).
Raijmakers et al. (2008) "Automated Online Sequential Isotope Labeling forProtein Quantitation Applied to Proteasome Tissue-Specific Diversity," Mol. Cell. Proteomics 7:1755-1762.
Rauniyar et al. (2014) "Isobaric Labeling-Based Relative Quantification in Shotgun Proteomics," Journal of Proteome Research 13, 5293-5309.
Rauniyar et al., "Stable isotope labeling of mammals (SILAM) for in vivo quantitative proteomic analysis", *Methods,* 61:260-268 (2013).
Reddie et al. (2008) "Expanding the functional diversity of proteins through cysteine oxidation," Current Opinion in Chemical Biology 12, 746-754.
Retzlaff et al. (2009) "Hsp90 is regulated by a switch point in the C-terminal domain," Embo Reports 10, 1147-1153.
Rhoads et al., "Neutron-Encoded Mass Signatures for Quantitative Top-Down Proteomics", *Anal. Chem.,* 86: 2314-2319 (2014).
Richards et al., "Neutron-encoded Signatures Enable Product lon Annotation From Tandem Mass Spectra", *Mol. Cell Proteomics,* 12:3812-3823 (2013).
Roberts et al. (2017) "Activity-based protein profiling for mapping and pharmacologically interrogating proteome-wide ligandable hotspots," Current Opinion in Biotechnology 43, 25-33.
Rogers et al. (2007) "The Dynamic Phagosomal Proteome and the Contribution ofthe Endoplasmic Reticulum," Proc. Natl. Acad. Sci. USA 104(47):18520-18525.

(56) References Cited

OTHER PUBLICATIONS

Rose et al., "NeuCode Mouse: Multiplexed Proteomics Analysis Reveals Tissue Specific Effects of Deubiquitinase Deletion", pp. 1-65, Presentation in Baltimore, MD (2014).
Rose et al., "Neutorn Encoded Labeling for Peptide Identification", *Anal. Chem.*, 85: 5129-5137 (2013).
Ross et al. (2004) "Multiplexed Protein Quantitation in *Saccharomyces cerevisiae* Using Amine-Reactive Isobaric Tagging Reagents," Mol. Cell. Proteomics 3:1154-1169.
Royle et al., "HPLC-based analysis of serum N-glycans on a 96-well plate platform with dedicated database software", Anal Biochem., 376 (1): 1-12 (2008).
Rudolf et al. (2013) "Chemical proteomics: ligation and cleavage of protein modifications," Current Opinion in Chemical Biology 17, 110-117.
Rudolf et al. (2013) "Copper-Assisted Click Reactions for Activity-Based Proteomics: Fine-Tuned Ligands and Refined Conditions Extend the Scope of Application," Chembiochem 14, 2447-2455.
Saha et al. (Mar. 2021) "Advances in chemical probing of protein O-GlcNAc glycosylation: structural role and molecular mechanisms," Chemical Society Reviews 50, 18, 10451-10485.
Sayre et al. (2008) "Oxidative stress and neurotoxicity," Chemical Research in Toxicology 21, 172-188.
Shankar et al. (2007) "Natural oligomers of the Alzheimer amyloid-beta protein induce reversible synapse loss by modulating an NMDA-type glutamate receptor-dependent signaling pathway," Journal of Neuroscience 27, 2866-2875.
Shek et al. (2006) "Fragmentations of Protonated Arginine, Lysine and Their Methylated Derivatives: Concomitant Losses of Carbon Monoxide or Carbon Dioxide and an Amine," J. Phys. Chem. A 110(27):8282-8296.
Sheng et al., "Preprocessing Significantly Improves the Peptide/Protein Identification Sensitivity of High-Resolution Isobarically Labeled Tandem Mass Spectrometry Data", *Mol. Cell Proteomics*, 14: 405-417 (2015).
Shetty et al. (2007) "Characterization by tandem mass spectrometry of stable cysteine sulfenic acid in a cysteine switch peptide of matrix metalloproteinases," Journal of the American Society for Mass Spectrometry 18, 1544-1551.
Sieber et al. (2006) "Analytical platforms for activity-based protein profiling—exploiting the versatility of chemistry for functional proteomics," Chemical Communications, 2311-2319.
Sinitcyn et al. (2018) "Computational Methods for Understanding Mass Spectrometry-Based Shotgun Proteomics Data," Annu. Rev. Biomed. Data Sci. 1: 207-234.
Sleno (2012) "The use of mass defect in modern mass spectrometry," Journal of Mass Spectrometry 47, 226-236.
Speechley et al., "Health-Related Quality of Life Among Child and AdolescentSurvivors of Childhood Cancer", J. Clin. Oncol., 24 (16): 2536-2543 (2006).
Speers et al. (2003) "Activity-based protein profiling in vivo using a copper(I)-catalyzed azide-alkyne [3+2] cycloaddition," Journal of the American Chemical Society 125, 4686-4687.
Speers et al. (2005) "A tandem orthogonal proteolysis strategy for high-content chemical proteomics," Journal of the American Chemical Society 127, 10018-10019.
Spradlin et al. (2019) "Harnessing the anti-cancer natural product nimbolide for targeted protein degradation," Nat Chem Biol. 15, 747-755.
Stensballe et al. (2001) "Characterization of phosphoproteins from electrophoretic gels by nanoscale Fe(III) affinity chromatography with off-line mass spectrometry analysis," Proteomics 1, 207-222.
Su et al. (2013) "Target identification of biologically active small molecules via in situ methods," Current Opinion in Chemical Biology 17, 768-775.
Sullivan et al., "The exploitation of selective cleavage of singly protonated peptide ions adjacent to aspartic acid residues using a quadrupole orthogonal time-of-flight mass spectrometer equipped with a matrix-assisted laser desorption/ionization source", *Int. J. Mass Spectrom.*, 210-211: 665-676 (2001).
Sun et al. (2002) "Carbonic anhydrase gating of attention: memory therapy and enhancement," Trends in Pharmacological Sciences 23, 83-89.
Sun et al. (2020) "Highly Efficient Peptide-Based Click Chemistry for Proteomic Profiling of Nascent Proteins," Analytical Chemistry 92, 8292-8297.
Supporting Information for Yang et al. "Glycan Analysis by Isobaric Aldehyde Reactive Tags and Mass Spectrometry", Anal. Chem., 85(17): 8188-8195 (2013) (Year: 2013).
Swaney et al. (2013) "Global analysis of phosphorylation and ubiquitylation cross-talk in protein degradation," Nature Methods 10, 676-682.
Swaney et al., "Decision Tree-Driven Tandem Mass Spectrometry for Shotgun Proteomics", *Nat. Meth.*, 5: 959-964 (2008).
Synowsky et al. (2009) "Comparative Multiplexed Mass Spectrometric Analyses of Endogenously Expressed Yeast Nuclear and Cytoplasmic Exosomes," J. Mol. Bioi.385:1300-1313.
Szychowski et al. (2010) "Cleavable Biotin Probes for Labeling of Biomolecules via Azide-Alkyne Cycloaddition," Journal of the American Chemical Society 132, 18351-18360.
Takakashi (1968) "The Reaction of Phenylglyoxal with Arginine Residues in Proteins," The Journal of Biological Chemistry 243(23): pp. 6171-6179.
Tang et al., "Fragmentation reactions of multiply-protonated peptides and implications for sequencing by tandem mass spectrometry with low-energy collision-induced dissociation", *Anal. Chem.*, 65:2824-2834 (1993).
Taniguchi et al., "Human Disease Glycomics/Proteome Initiative (HGPI)", Mo/. Cell. Proteomics, 7(3): 626-627 (2008).
Thompson et al. (2003) "Tandem Mass Tags: A Novel Quantification Strategy for Comparative Analysis of Complex Protein Mixtures by MS/MS," Anal. Chem.75:1895-1904.
Tian et al. (2007) "Solid-phase extraction of N-linked glycopeptides," Nature Protocols 2, 334-339.
Tian et al. (2018) "Chemoproteomics Reveals Unexpected Lysine/Arginine-Specific Cleavage of Peptide Chains as a Potential Protein Degradation Machinery," Analytical Chemistry 90, 794-800.
Ting et al., "MS3 eliminates ratio distortion in isobaric multiplexed quantitative proteomics," *Nat. Meth.*, 8:937-940 (Oct. 2011).
Tutturen et al. (2014) "Assessing the Citrullinome in Rheumatoid Arthritis Synovial Fluid with and without Enrichment of Citrullinated Peptides" J. ProteomeRes. 13(6): pp. 2867-2873.
Uehara et al. (2006) "S-Nitrosylated protein-disulphide isomerase links protein misfolding to neurodegeneration," Nature 441, 513-517.
Ulbrich et al., "Neutron-encoded protein quantification by peptide carbamylation", *J. Am. Soc. Mass Spectrom.*, 25(1):6-9 (2014).
Ulbrich et al., "Organic Acid Quantitation by NeuCode Methylamidation", *Anal. Chem.*, 86: 4402-4408 (2014).
Vincent, et al., "Automated gas-phase purification for accurate, multiplexed quantification on a stand-alone ion-trap mass spectrometer", *Anal. Chem.*, 85:2079-2086 (2013).
Vinogradova et al. (2020) "An Activity-Guided Map of Electrophile-Cysteine Interactions in Primary Human T Cells," Cell. 182, 1009-1026.
Walker et al. (2010) "Protein disulphide isomerase protects against protein aggregation and is S-nitrosylated in amyotrophic lateral sclerosis," Brain 133, 105-116.
Wang et al. (2009) "Targeted Quantitative Mass Spectrometric Identification of Differentially Expressed Proteins between Sax-Expressing and Deficient Colorectal Carcinoma Cells," J. Proteome Research 8:3403-3414.
Wang et al. (2014) "A Chemoproteomic Platform To Quantitatively Map Targets Of Lipid-Derived Electrophiles," Nature Methods, 11, 79-85.
Wang et al. (2017) "PADI2-Mediated Citrullination Promotes Prostate CancerProgression" Cancer Research 77(21): pp. 5755-5768.
Weerapana et al. (2010) "Quantitative reactivity profiling predicts functional cysteines in proteomes," Nature 468, 790-795.
Wenger et al., "Gas-phase purification enables accurate, multiplexed proteome quantification with isobaric tagging", *Nat. Meth.*, 8:933-935 (2011).

(56) References Cited

OTHER PUBLICATIONS

Wijasa et al. (2020) "Quantitative proteomics of synaptosome S-nitrosylation in Alzheimer's disease," Journal of Neurochemistry 152, 710-726.
Wong et al. (1999) "Direct force measurements of the streptavidin-biotin interaction," Biomolecular Engineering 16, 45-55.
Wu et al., "Metabolic Labeling of Mammalian Organisms with Stable Isotopes for Quantitative Proteomic Analysis", *Anal. Chem.,* 76: 4951-4959 (2004).
Xia et al., "Glycan reductive isotope labeling for quantitative glycomics", Anal.Biochem., 387(2): 162-70 (2009).
Xiang, et al., "N,N-Dimethyl Leucines as Novel Isobaric Tandem Mass Tags for Quantitative Proteomics and Peptidomics," Anal. Chem., 82(7):2817-2825 (2010).
Xie et al. (2020) "Simultaneous Affinity Enrichment of Two Post-Translational Modifications for Quantification and Site Localization," Jove—Journal of Visualized Experiments.
Yang et al. (2004) "Approach to the comprehensive analysis of glycoproteins isolated from human serum using a multi-lectin affinity column," Journal of Chromatography A 1053, 79-88.
Yang et al. (2015) "Activity-Based Protein Profiling: Recent Advances in Probe Development and Applications," Chembiochem 16, 712-724.
Yang et al. (2015) "Global, in situ, site-specific analysis of protein S-sulfenylation," Nature Protocols 10, 1022-1037.
Yang et al., "Glycan Analysis by Isobaric Aldehyde Reactive Tags and Mass Spectrometry", Anal. Chem., 85(17): 8188-8195 (2013).
Yang et al., "QUANTITY: An Isobaric Tag for Quantitative Glycomics", Sci. Rep., 5:17585 (2015).
Yao et al. (2011) "SUMOylation-regulated Protein Phosphorylation, Evidence from Quantitative Phosphoproteomics Analyses," Journal of Biological Chemistry 286, 27342-27349.
Yonezawa et al. (2014) "New photocleavable linker: alpha-Thioacetophenone- type linker," Bioorganic & Medicinal Chemistry Letters 24, 2831-2833.
Yuan et al., "Isotope tag method for quantitative analysis of carbohydrates by liquid chromatography-mass spectrometry", J. Chromatogr. A, 1067(1-2): 145-152(2005).
Zareba-Koziol et al. (2014) "Global Analysis of S-nitrosylation Sites in the Wild Type (APP) Transgenic Mouse Brain-Clues for Synaptic Pathology," Molecular & Cellular Proteomics 13, 2288-2305.
Zeng et al. (2009) "Revival of Deuterium-Labeled Reagents for Protein Quantitation," Chem. Commun. pp. 3369-3371.
Zhang et al. (2002) "Controlling Deuterium Isotope Effects in Comparative Proteomics," Anal. Chem. 74:3662-3669.
Zhang et al. (2010) "S-Nitrosylation of Cyclin-Dependent Kinase 5 (Cdk5) Regulates Its Kinase Activity and Dendrite Growth During Neuronal Development," Journal of Neuroscience 30, 14366-14370.
Zhang et al. (Sep. 2010) "Deuterium Isobaric Amine-Reactive Tags for Quantitative Proteomics," Anal. Chem. 82(18):7588-7595.
Zhao et al. (2015) "S-Nitrosylation in Alzheimer's disease," Molecular Neurobiology 51, 268-280.
Zhou et al. (2016) "Chemoproteomic Strategy to Quantitatively Monitor Transnitrosation Uncovers Functionally Relevant S-Nitrosation Sites on Cathepsin D and HADH2," Cell Chemical Biology 23, 727-737.
Zhou et al., "Mass defect-based pseudo-isobaric dimethyl labeling for proteome quantification", *Anal. Chem.,* 85: 10658-10663 (2013).
U.S. Appl. No. 15/182,329, filed Jun. 14, 2016.
U.S. Appl. No. 15/768,299, filed Oct. 14, 2016.
U.S. Appl. No. 16/252,464, filed Jan. 18, 2019.
U.S. Appl. No. 17/121,242, filed Dec. 14, 2020.
Black et al. (1994) "Atrial Natriuretic Peptide," Compendium on Continuing Education for the Practicing Veterinarian, 16, 717-729 and 815.
Xiang et al. (Jun. 1-5, 2008) "N, N-Dimethyl Amino Acids as iTRAQ Reagent for Improved Peptdiomics and Proteomics," Proceedings of the 56th ASMS Conference on Mass Spectrometry and Allied Topics, Denver, CO.
Xiang et al. (May 31-Jun. 4, 2009) "Generating Neuropeptide Standard Curve in a Single LC-MS Run by N, N-Dimethyl Amino Acids Tandem Mass Tags," Proceedings of the 5ihASMS Conference on Mass Spectrometry and Allied Topics.

* cited by examiner

Exact Mass: 581.3472

Candidate A

Candidate B

Candidate C

Candidate D

Candidate E

Candidate C

DBA tag =

115a $C_7H_{16}{}^{15}N$ 115.12476

115b $C_6{}^{13}CH_{16}N$ 115.13108

118a $C_4{}^{13}C_3H_{16}{}^{15}N$ 118.13483

116a $C_6{}^{13}CH_{16}{}^{15}N$ 116.12812

117a $C_5{}^{13}C_2H_{16}{}^{15}N$ 117.13147

118b $C_6{}^{13}CH_{14}D_2{}^{15}N$ 118.14067

116b $C_5{}^{13}C_2H_{16}N$ 116.13444

117b $C_7H_{14}D_2{}^{15}N$ 117.13731

118c $C_5{}^{13}C_2H_{14}D_2N$ 118.14699

116c $C_7H_{16}D_2N$ 116.14028

117c $C_6{}^{13}CH_{14}D_2N$ 117.14363

118d $C_7H_{12}D_4N$ 118.15283

$^{13}C$ $^{15}N$ $^{2}H$

*S-sulfenylation*

*Carbonylation*

*S-sulfinylation*

*Citrullination*

MULTIPLEXED DILEU-BIOTIN-AZIDE (DBA) TAG ENABLED ISOBARIC TANDEM ORTHOGONAL PROTEOLYSIS ACTIVITY-BASED PROTEIN PROFILING (isoBOP-ABPP) PLATFORM FOR HIGH-THROUGHPUT QUANTITATIVE PAN-PTM ANALYSIS

CROSS-REFERENCE TO RELATED APPLICATION

This application claims priority from U.S. Provisional Application No. 63/352,510, filed Jun. 15, 2022, which is incorporated by reference herein to the extent that there is no inconsistency with the present disclosure.

STATEMENT REGARDING FEDERALLY SPONSORED RESEARCH OR DEVELOPMENT

This invention was made with government support under AG052324 and GM108538 awarded by the National Institutes of Health. The government has certain rights in the invention.

BACKGROUND OF THE INVENTION

The human genome project revealed less than 25,000 protein-coding genes (1). However, the total number of proteins in the human proteome is estimated at over one million. Part of this complexity and diversity arises from post-translational modifications (PTMs), a process where proteins are covalently modified during or after their assembly on the ribosome. PTM plays an important role in protein functions because they regulate protein activity, localization, and interaction with other cellular molecules such as glycans, nucleic acids, lipids, and cofactors (2).

Aberrant states of PTMs are frequently implicated in many human diseases, such as cancers, diabetes, and neurodegenerative diseases (3-5). In addition, it is recently recognized that PTMs act in combination on proteins for modulation and regulation purposes, and this PTMs cross-talks further expand the landscape of proteomes in eukaryotes, providing a fine-tuning mechanism in regulating protein function, localization, and interaction with other molecules (6-8). Therefore, identifying and quantifying PTMs is critical for gaining a comprehensive understanding of molecular mechanisms underlying physiological activities and human diseases. Among the protein-coding amino acids, cysteine is the most intrinsically nucleophilic amino acid and sensitive to oxidation. The pKa of the free cysteine thiol is between 8 and 9, meaning that only slight perturbations in the local protein microenvironment can result in ionized thiolate groups with enhanced reactivity at physiological pH (9). In addition to its role in catalysis, cysteine is subject to several forms of oxidative post-translational modifications, including sulphenation (SOH), sulphination ($SO_2H$), nitrosylation (SNO), disulphide formation and glutathionylation, which endow it with the ability to serve as a regulatory switch on proteins that is responsive to the cellular redox state (10). Elevated oxidative/nitrosative stress has been recognized as the key features of many neurodegenerative disorders such as Parkinson's diseases (PD), Alzheimer's disease (AD), and amyotrophic lateral sclerosis (ALS) (11,12). Mass spectrometry (MS)-based proteomics has gained great popularity in detecting and structurally defining covalent changes in a protein.

However, the lack of versatile and high-throughput tools has previously limited studies of PTM dynamics. In order to address these challenges, and to fill in existing knowledge gaps, the improved tagging reagents of the present invention were developed.

SUMMARY OF THE INVENTION

The present invention provides novel isobaric chemical tags, particularly DiLeu-Biotin-Azide (DBA) tags, that are useful in proteomics and quantification of post-translational modifications (PTMs). In an aspect of the invention, the present multiplex isobaric comprises three "modules": (1) an isobaric tag comprising a reporter group (including, but not limited to, a DiLeu reporter group) and for relative quantification using MS/MS (MS2); (2) an enrichment moiety (including, but not limited to, a biotin moiety) for selective purification or enrichment such as through binding with streptavidin beads; and (3) a conjugation moiety (including, but not limited to, an azide functional group to enable biorthogonal click chemistry). An example of such a DBA tag in an embodiment of the invention is illustrated below:

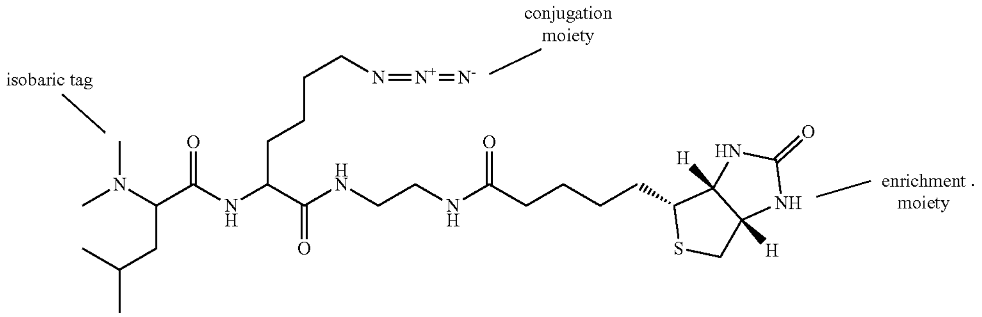 [SMILES: CC(C)CC(C(=O)NC(CCCCN=[N+]=[N-])C(=O)NCCNC(=O)CCCC[C@H]1SC[C@H]2NC(=O)N[C@H]21)N(C)C]

When combined with specific probes able to bind efficiently with the conjugation moiety (including but not limited to probes having alkyne groups), the trifunctional structure can introduce isotopic labels onto the site of a post-translational modification (PTM) and followed by selective purification or enrichment. The invention includes both cleavable (cDBA) and non-cleavable versions (DBA).

As a result, the present invention provides a highly versatile tag for high-throughput quantitative MS/MS analysis of proteins having PTMs. The trifunctional nature enables simultaneous isobaric labeling, high-efficiency click chemistry conjugation, and selective purification or enrichment. In an embodiment, the compatibility with multiplexing enables simultaneous analysis of 21 samples using a simple dimethylated leucine derived reporter group. In addition, the DBA tag is relatively straightforward to synthesize, which makes it more affordable/accessible. When combined with an activity-based protein profiling strategy, special alkyne probes can target various PTMs, including cysteine oxidation, protein carbonylation, and citrullination. Further, DBA provides high reporter ion yield with abundant backbone fragment ions at lower collisional energy levels. The DBAs also have a high enrichment efficiency (90% in proof-of-concept experiments) thanks to the biotin functionality. Finally, the tags only incrementally increase the mass on PTM sites, serving to minimize effect on physical properties and fragmentation efficiency while enhancing analysis.

In an embodiment, the present invention provides a mass spectrometry tagging reagent comprising a compound having: a) an isobaric tag comprising a reporter group having at least one atom that is optionally isotopically labeled and a balancing group also having at least one atom that is optionally isotopically labeled; b) an enrichment moiety; and c) a conjugation moiety able to bind to a molecule of interest. Preferably, one or more carbon atoms in the reporter group are $^{13}C$, one or more oxygen atoms are $^{18}O$, one or more nitrogen atoms in the reporter group $^{15}N$, or combinations thereof. In an embodiment, the isobaric tag comprises one or more dimethylated amino acids or acylated amino acids, where the reporter group contains at least a portion of one or more dimethylated or acylated amino acids. In an embodiment, the isobaric tag comprises a dimethylated leucine group having the formula:

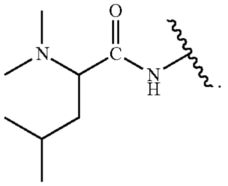 [SMILES: *NC(=O)C(CC(C)C)N(C)C]

In an embodiment, the enrichment moiety comprises a functional group able to bind to a solid support, streptavidin, or avidin, in order to enable enrichment or purification of the tagged molecule of interest. Preferably, the enrichment moiety comprises biotin or a biotin derivative. In an embodiment, the enrichment moiety comprises a moiety having the formula:

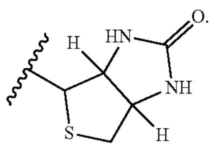 [SMILES: *C1SCC2NC(=O)NC21]

In an embodiment, the conjugation moiety comprises a functional group, including but not limited to an azide or a protected azide, able to bind to a functional group of the molecule of interest or to a functional group of a probe attached to the molecule of interest. By "protected azide" it is meant that the conjugation moiety comprises a functional group that is unreactive under certain conditions, but can be altered to have a reactive azide group under other conditions. Preferably, the conjugation moiety comprises an azide functional group having the formula:

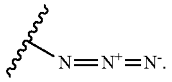

In an embodiment, the molecule of interest comprises an alkynyl group or a dibenzocyclooctyne (DBCO) group able to bind to the conjugation moiety. Preferably, the molecule of interest contains a terminal alkyne or DBCO group having the formula:

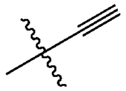

terminal alkyne

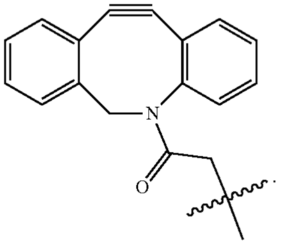

DBCO

In an embodiment, multiple tagging reagents are used to label two or more molecules of interest or a mixture of molecules, wherein the tagging reagents have the same molecular weight as one another, but the reporter group of each tagging reagent has a different mass due to the different isotopically labeled atoms in each reporter group. Similarly, the balancing group of each tagging reagent has a different mass from one another due to the different isotopically labeled atoms in each balancing group. In an embodiment, the reporter group and balancing group will break apart from one another during MS2 fragmentation to produce different fragmentation ions. Each molecule of interest can be labeled individually, pooled together, and introduced into the mass spectrometer for quantitative analysis. Since the tagging reagents have the same mass, the labeled molecules can produce a single peak or combined peaks in MS mode (depending on the resolution of the MS device), but upon MS2 fragmentation, each sample labeled with a different tagging reagent will produce a unique reporter ion due to the mass difference between the reporter groups. Preferably, a molecule labeled with a tagging reagent of the present invention is able to form a strong immonium ion during MS2 fragmentation. The peptides labeled using the compounds described herein may be peptides having PTMs.

In one embodiment, the tagging reagents of the present invention are derived from a peptide comprising two or more amino acids. Preferably the amino acids are natural amino acids, but the present invention contemplates the use of unnatural, non-standard and synthetic amino acids, such as β amino acids, as the amino acid which makes up the reporter group, the balancing group, or both. The amino acids may be modified, including but not limited to amino acids that have been modified to contain one or more additional methyl groups, ethyl groups, acyl groups, or combinations thereof. In an embodiment, the tagging reagents of the present invention are derived from a dipeptide where an amino group of one amino acid has been methylated, ethylated, or acylated. The free carboxyl group of the dipeptide can be attached to an amine reactive group or a target molecule, such as a peptide. During MS2 fragmentation, the dipeptide will fragment to form a reporter ion, preferably an immonium ion, which can be readily detected.

In an embodiment, the isobaric tag portion of the tagging reagent comprises any dimethylated, diethylated, and/or asymmetric alkylated amino acid (D and L) structures. As a non-limiting example, the isobaric tag portion comprises one or more of dimethyl valine, diethyl valine, and/or asymmetric alkylated valine; dimethyl alanine, diethyl alanine, and/or asymmetric alkylated alanine; dimethyl leucine, diethyl leucine, and/or asymmetric alkylated leucine; etc. In an embodiment, the isobaric tag portion of the tagging reagent comprises or are derived from N,N-dimethyl leucine (DiLeu); N,N-dimethyl isoleucine (Di Ile); N,N-dimethyl alanine (DiAla); N,N-dimethyl glycine (DiGly); N,N-dimethyl valine (DiVal); N,N-dimethyl histidine (DiHis); N,N-dimethyl phenylalanine (DiPhe); N,N-dimethyl tryptophan (DiTrp); N,N-dimethyl lysine (DiLys) or N,N-dimethyl tyrosine (DiTyr). In an embodiment, the tagging reagents comprise or are derived from N,N-diethyl leucine; N,N-diethyl isoleucine; N,N-diethyl alanine; N,N-diethyl glycine; N,N-diethyl valine; N,N-diethyl histidine; N,N-diethyl phenylalanine; N,N-diethyl tryptophan; N,N-diethyl lysine or N,N-diethyl tyrosine (i.e., the ethylated counterparts to the above examples).

In an embodiment, one or more atoms in the reporter group, balancing group, or both, in each tagging reagent are the isotopically heavy versions of the atom. Each tagging reagent in the series will have a different combination of atoms that are the isotopically heavy versions of the atoms, such as $^{18}O$, $^{13}C$, $^{15}N$ or D, but with the condition that the total aggregate mass of each tagging reagent is the same as the other tagging reagents in the series. The balancing groups of each tagging reagent will contain the appropriate number of heavy isotopes, such as $^{18}O$, $^{13}C$ $^{15}N$ or D, so that the combined mass of the balancing group and reporter group are the same for each reagent. Varying the atoms which contain the heavy isotope form in the reporter groups and balancing groups allows each tagging reagent to have the same combined mass but a different mass of the reporter group after fragmentation. Preferably, the heavy isotopes used in the tagging reagents do not include deuterium.

In an embodiment, the tagging reagents further comprise one or more linkers positioned between the isobaric tag, enrichment moiety, conjugation moiety, or combinations thereof. Preferably, the one or more linkers are cleavable linkers. In an embodiment, the one or more linkers comprise a polyethylene glycol (PEG) linker, a Boc linker, a dialkoxydiphenylsilane (DADPS) linker, a diol linker, an aminophenol linker, or combinations thereof. Preferably, the tagging reagent comprises a DADPS linker.

In an embodiment, the present invention provides a tagging reagent having the formula:

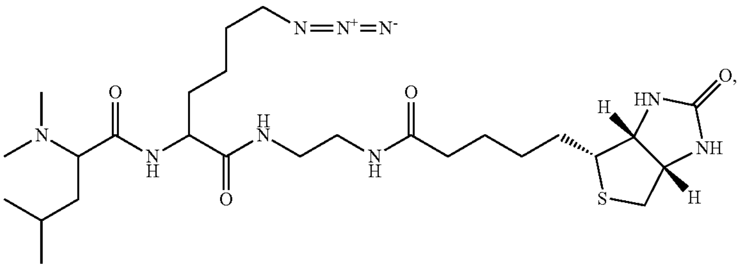

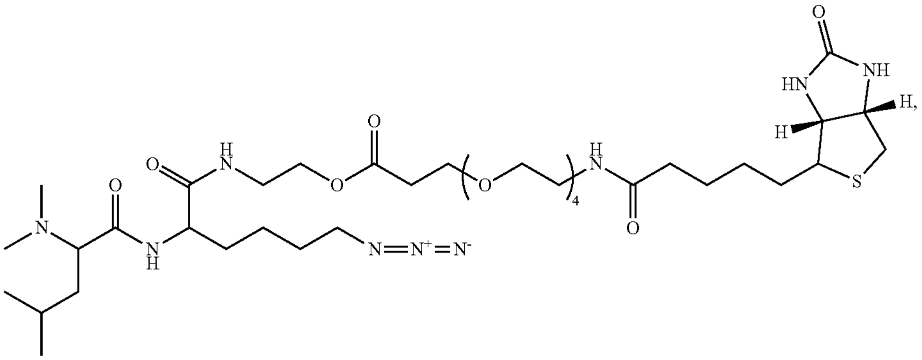

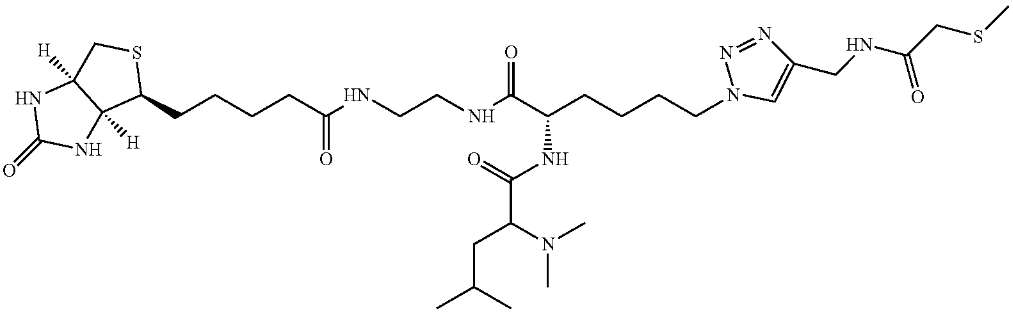

,

-continued
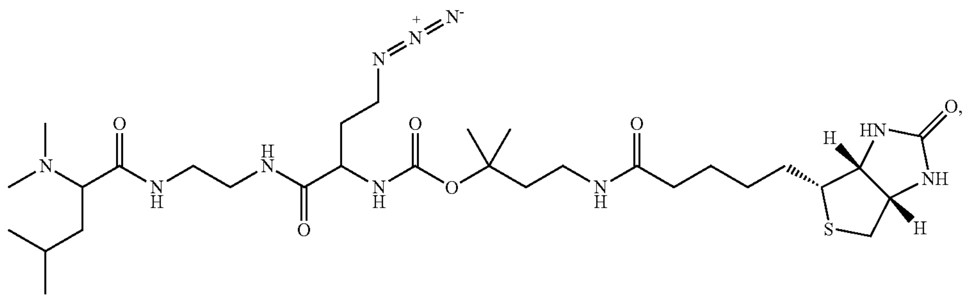
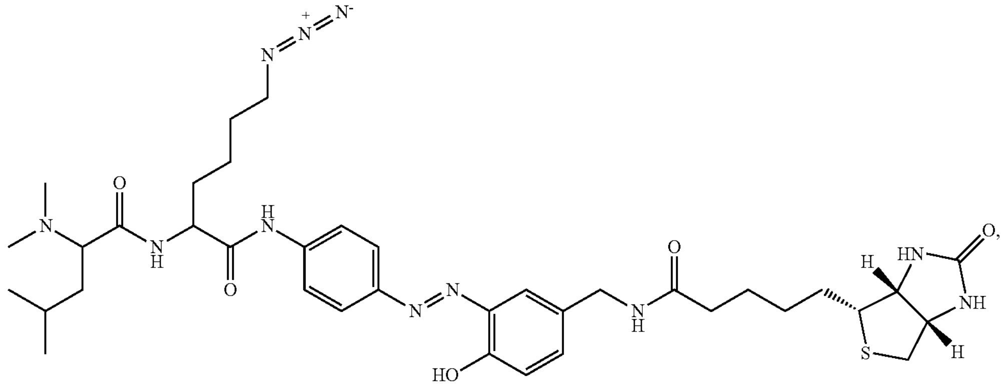
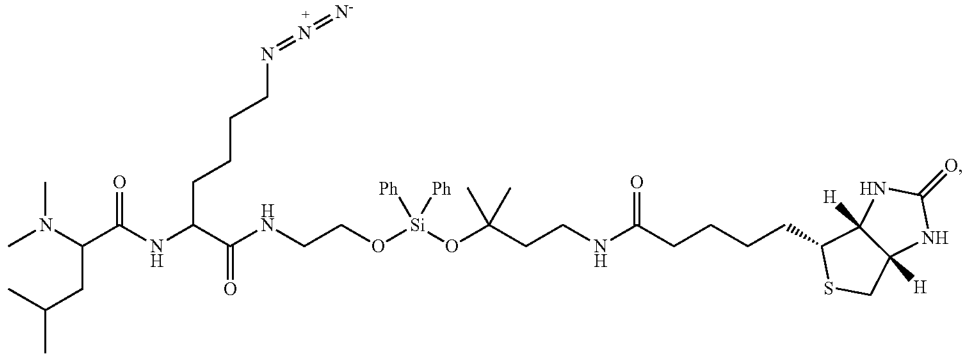
or
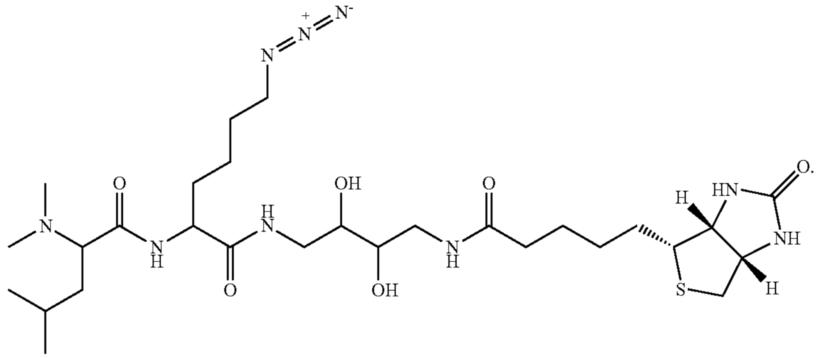

In an embodiment, the present invention provides a tagging reagent having the formula:

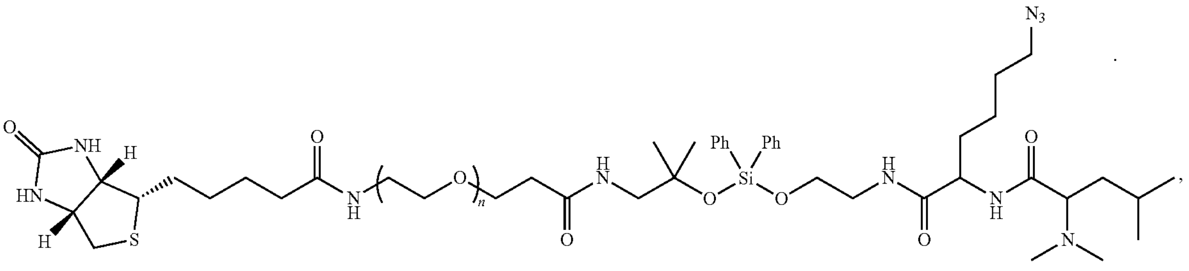

where n is an integer ranging from 0 to 10. Preferably, n is an integer ranging from 2 to 8, from 3 to 7, or from 4 to 6. In an embodiment, n is 4.

The tagging reagents of the present invention demonstrate high labeling efficiency and enrichment selectivity as well as enhance fragmentation of reporter ions that facilitate quantitation at reduced collisional energies with unambiguous localization of the modification sites.

In an embodiment, the present invention provides a method of analyzing a molecule, said method comprising the steps of:

a) providing the molecule;
b) labeling the molecule with a compound having: i) an isobaric tag comprising a reporter group having at least one atom that is optionally isotopically labeled and a balancing group also having at least one atom that is optionally isotopically labeled; ii) an enrichment moiety; and iii) a conjugation moiety able to bind to a molecule of interest;
c) purifying or enriching the labeled molecule;
d) fragmenting the purified molecule to generate an immonium ion from the purified molecule; and
e) detecting and analyzing fragments of the purified molecule.

In an embodiment, the molecule is a peptide or protein, preferably a peptide or protein having one or more post-translational modifications (PTMs), including but not limited to phosphorylation, acetylation, hydroxylation, methylation, glycosylation, carbonylation, lipidation, citrullination, sulfation, sulfenylation, sulfinylation, sulfonylation, and hydroxylation. In an embodiment, labeling the molecule of interest with the labeling compound comprises the step of reacting the conjugation moiety with a functional group of the molecule. In a further embodiment, labeling the molecule comprises the step of reacting the modification site of the peptide or protein to contain a terminal alkyne or DBCO group able to react with an azide group of the labeling compound. Preferably, this reaction is a high yield reaction.

In an embodiment, the molecule of interest is reacted in order to contain a functional group able to react with the conjugation moiety of the labeling compound. For example, a peptide or protein having a PTM may be reacted with a probe, where one a portion of the probe is able to react to the modified site of the peptide or protein, and another portion of the probe contains a terminal alkyne or DBCO group.

Once the molecule of interest is labeled with the compound, the labeled molecule may be purified or enriched by binding the enrichment moiety of the labeled molecule to a solid support or a biomolecule having a high binding affinity. In an embodiment, the enrichment moiety comprises biotin or a biotin derivative, and purifying or enriching the labeled molecule comprises binding the labeled molecule to a solid support, streptavidin, or avidin, followed by one or more purification steps to remove unbound molecules.

The present invention also provides a kit comprising two or more tagging reagents (also referred to as labeling compounds) as described above, wherein each tagging reagent comprises: a) a reporter group having at least one atom that is optionally isotopically labeled and a balancing group also having at least one atom that is optionally isotopically labeled; b) an enrichment moiety; and d) a conjugation moiety able to bind to a molecule of interest; wherein the reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same. Preferably, the tagging reagents are able to generate an immonium ion.

Preferably, the kit comprises two or more tagging reagents, three or more tagging reagents, four or more tagging reagents, five or more tagging reagents, six or more tagging reagents, seven or more tagging reagents, eight or more tagging reagents, nine or more tagging reagents, ten or more tagging reagents, eleven or more tagging reagents, twelve or more tagging reagents, thirteen or more tagging reagents, fourteen or more tagging reagents, fifteen or more tagging reagents, or sixteen or more tagging reagents.

DETAILED DESCRIPTION OF THE INVENTION

Definitions

Figure 1:
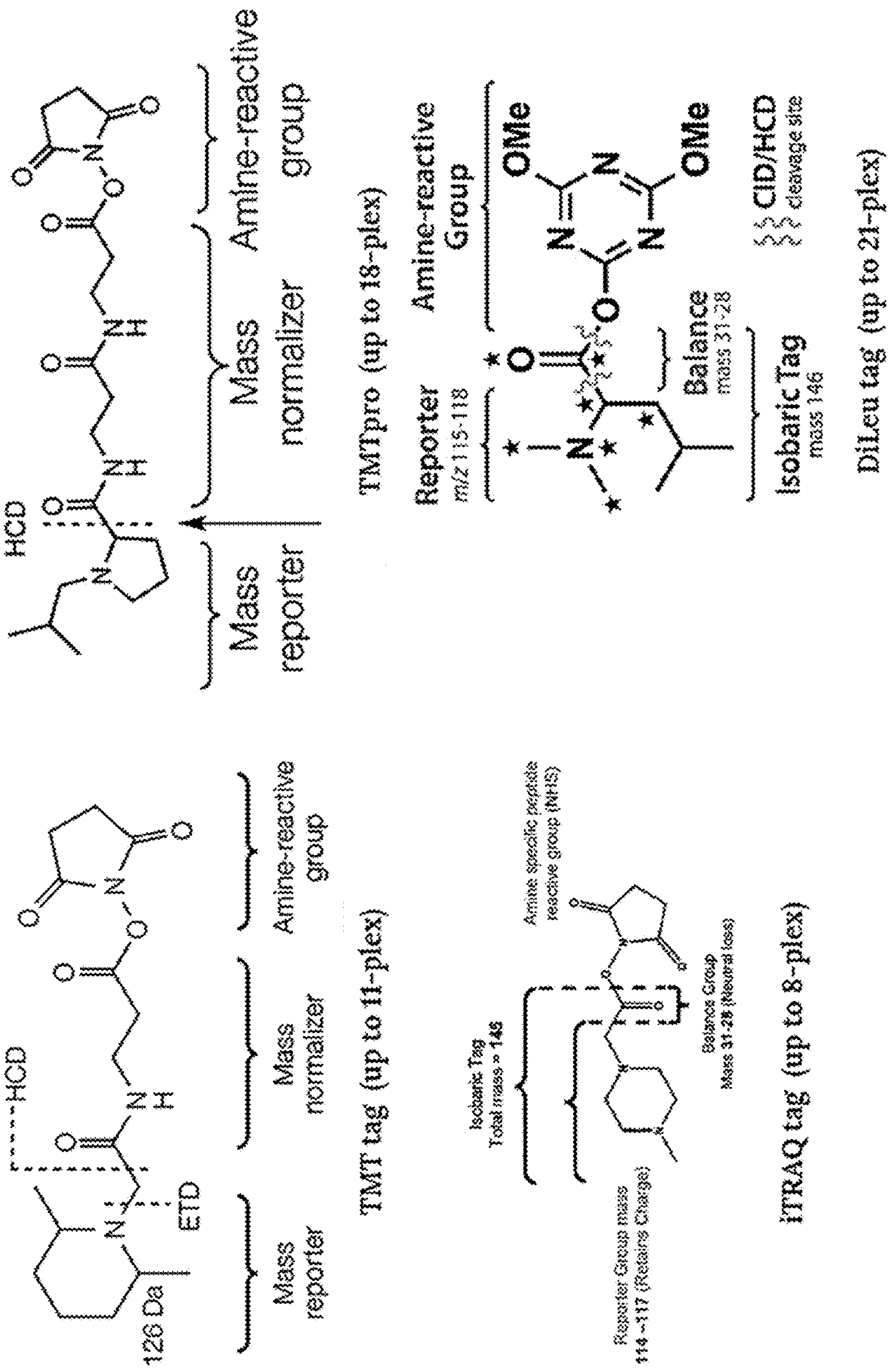
Prior Art Fig. 1
FIG. 1 shows different types of isobaric tags comprising a reporter group and balancing group or mass normalizing group. Also illustrated is the number of multiplexing (i.e., the number of samples that can be analyzed simultaneously using) for each isobaric tag.

As used herein the terms "tagging" and "labeling" refers to reacting a reagent or compound with a molecule of interest, including but not limited to peptides having a post-translational modification (PTM), so that one or more functional groups are attached to the molecule of interest. A "tagged" or "labeled" peptide or molecule of interest refers to a peptide or molecule of interest having the one or more functional groups attached.

The terms "peptide" and "polypeptide" are used synonymously in the present disclosure, and refer to a class of compounds composed of amino acid residues chemically bonded together by amide bonds (or peptide bonds). Peptides are polymeric compounds comprising at least two amino acid residues or modified amino acid residues. Peptides include compositions comprising a few amino acids and include compositions comprising intact proteins or modified proteins. Peptides include proteins and further include compositions generated by degradation of proteins, for example by proteolytic digestion. Peptides and polypeptides may be generated by substantially complete digestion or by partial digestion of proteins. Identifying or sequencing a peptide refers to determination of its composition, particularly its amino acid sequence, and characterization of any modifications of one or more amino acids comprising the peptide or polypeptide.

"Protein" refers to a class of compounds comprising one or more polypeptide chains and/or modified polypeptide chains. Proteins may be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins may also include non-naturally occurring derivatives, analogues and functional mimetics generated by chemical synthesis. Exemplary derivatives include chemical modifications such as alkylation, acylation, carbamylation, iodination or any modification that derivatizes the protein. In the present invention, proteins may be modified by labeling methods, such as metabolic labeling, enzymatic labeling or by chemical reactions. Proteins may be modified by the introduction of stable isotope tags, for example as is typically done in a stable isotope dilution experiment. Proteins of the present invention may be derived from sources, which include but are not limited to cells, cell or tissue lysates, cell culture medium after cell growth, whole organisms or organism lysates or any excreted fluid or solid from a cell or organism.

An "amino acid" refers to an organic compound containing an amino group ($NH_2$), a carboxylic acid group (COOH), and any of various organic side groups that have the basic formula $NH_2CHRCOOH$. Natural amino acids are those amino acids which are produced in nature, such as isoleucine, alanine, leucine, asparagine, lysine, aspartic acid, methionine, cysteine, phenylalanine, glutamic acid, threonine, glutamine, tryptophan, glycine, valine, proline, serine, tyrosine, arginine, and histidine as well as ornithine and selenocysteine.

"Fragment" refers to a portion of molecule, such as a peptide. Fragments may be singly or multiply charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond, or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a parent analyte, such as a polypeptide analyte, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum. Molecule fragments are able to be detected, identified and optionally quantified using methods as known in the art.

The term "alkyne" refers to a hydrocarbon containing at least one carbon-carbon triple bond. Similarly, the term "alkynyl" refers to a monoradical of a branched or unbranched unsaturated hydrocarbon group having one or more triple bonds. Alkynyl groups include those having from 2 to 20 carbon atoms, preferably having from 2 to 12 carbon atoms. Alkynyl groups include medium length alkenyl groups having from 4-10 carbon atoms, and long alkynyl groups having more than 10 carbon atoms, particularly those having 10-20 carbon atoms.

As used herein, "isotopically labeled", "isotopic", "isotopes", "isotope", "isotopically-different", "isotopically enriched" and the like refer to compounds (e.g., tagging reagents, target analytes, labeled samples and end-products, etc.) whereby a process has introduced one or more isotopes into the relevant compound in excess of the natural isotopic abundance for that atom. "Isotopically-heavy" refers to a compound or fragments/moieties thereof that have been enriched with one or more high mass, or heavy isotopes (e.g., stable isotopes such as deuterium, $^{13}C$ $^{15}N$, and $^{18}O$).

In an embodiment, an isotopically enriched compound comprises a specific isotopic composition, wherein one or more isotopes are present in an abundance that is at least 10 times greater, for some embodiments at least 100 times greater, for some embodiments at least 1,000 times greater, for some embodiments at least 10,000 times greater, than the abundance of the same isotopes in a naturally occurring sample. In another embodiment, an isotopically enriched compound has a purity with respect to a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched compound is a compound that has been purified with respect to a specific isotopic composition, for example using isotope purification methods known in the art.

Overview

Proteomics includes the analysis of "proteoforms" that arise from genetic variations and post-translational modifications (PTMs) of proteins. Discovery-based proteomics studies rely on quantifying differences in protein expression across biological states to characterize complex mechanisms and recognize potential diagnostic biomarkers of disease and therapeutic targets. Stable isotope labeling paired with liquid chromatography tandem mass spectrometry (LC-MS/MS) is a well-established approach for simultaneous identification and quantification of multiple samples in parallel. These labeling techniques (e.g., SILAC, NeuCode, iTRAQ, TMT, etc.) impart isotopic mass differences that give rise to unique peaks in MS spectra allowing for the calculation of relative abundances of proteins in a sample. As an example, a series of isobaric tagging reagents may comprise a reporter group (which forms the reporter ion during fragmentation) and a balance group. Each tagging reagent in a series will have a different combination of atoms comprising isotopically light and/or heavy versions of the atoms, but with the condition that the total aggregate mass of each tagging reagent is the same as the other tagging reagents in the series. The balancing groups of each reagent will contain the appropriate number of light and/or heavy isotopes, so that the combined mass of the balancing group and reporter group are the same for each reagent. After fragmentation, the reporter group for each tagged peptide or molecule will present a different mass due to the differently isotopically labeled atoms.

FIG. 1 illustrates different types of isobaric tags comprising a reporter group and balancing group suitable for incorporation into the compounds of the present invention (see Xiang et al., Anal. Chem., 2012, 82(7): 28-17-2825). In particular, the Li et al. group previously developed "DiLeu" isobaric tags as an efficient and cost-effective alternative for quantitative proteomics (see, for example, U.S. Pat. No. 9,388,132). Leveraging their earlier work, the Li group sought to expand their DiLeu platform to better capture PTMs, including but not limited to cysteine derivatives.

The present invention provides a set of novel isobaric chemical tags, including but not limited to DiLeu-Biotin-Azide (DBA), which have compact structure and are able to be synthesized with low to moderate synthetic complexity in-house. The multiplex tags of the present invention comprise three modules, where an isobaric reporter group is employed for relative quantification on MS2 spectra; a biotin derived moiety is able to achieve selective enrichment by binding to streptavidin or similar beads, and an azide functional group is able to be used for biorthogonal click chemistry or similar binding of target molecules.

Further description and embodiments of the present invention are presented in the non-limiting examples below.

Benefits and Comparisons to Existing Technology

The trifunctional architecture of DBA tag makes it highly versatile. It is able to achieve isobaric labeling, click chemistry conjugation and selective purification or enrichment at one time. Since the quantification is based on MS2, high-throughput analysis can be readily implemented. No similar commercially available tags utilize a MS2 based quantification strategy, and they are not able to achieve more than duplex analysis at a single experiment, while the present DBA tags can easily analyze 12 or 21 samples simultaneously.

The present isobaric tags also permit an accessible and cost-efficient synthesis approach. The overall synthetic route for DBA tag consists of six steps with simple organic chemistry using accessible building blocks. Previously reported and commercially available analogs such as TEV tag and DADPS-Biotin-Azide commonly possess bulky structures and are difficult to produce in-house, which prevent their broad applications to more general researchers and labs.

The DBA tags also serve as a platform for various PTM analysis which is benefited from its modular design. Through activity-based protein profiling (ABPP) strategy, special alkyne probes or DBCO-containing probes can target various different PTMs including but not limited to cysteine oxidation, protein carbonylation and citrullination, where all of those can be labeled by DBA tag via biorthogonal click chemistry. This application was successfully demonstrated on S-nitrosylation (SNO), S—S-sulphenation (SOH) and protein carbonylation using peptide standards.

The present tags also enable simple labeling protocols and high labeling efficiency. Copper(I)-catalyzed azide/alkyne cycloaddition (CuAAC) reaction, so-called click chemistry, is biorthogonal, readily operated and very efficient. It bridges the DBA tag and the sites of proteins or peptides with specific PTMs which have been derivatized by precursor alkyne probes in advance. Complete labeling was observed when comparing the database search results for the enriched peptides from MCF7 cell lysate in which modification was set as either fixed or variable. MALDI-MS results also exhibited complete labeling efficiency on peptide standards.

Experiments with the present tags also demonstrated high reporter ion yield with abundant backbone fragment ions at lower collisional energy level. The modification sites can be unambiguously assigned by abundant backbone fragment ions, while the relative quantification can be achieved based on reporter ion intensities, all in a single scan event. Even for successive adjacent modified sites, they were accurately pinpointed no matter the locations are in the middle of the sequences or at the terminus.

Decent signal of reporter ions can also be used as the diagnostic ions for developing targeted quantitative analysis enabled by parallel reaction monitoring mass spectrometry (PRM-MS).

The present tags also are able to provide high specificity of enrichment performance. A classic biotin-streptavidin interaction was employed for selective enrichment. The cDBA allows for using high-capacity streptavidin beads and enriched peptides or proteins can be readily eluted in 10% ammonium hydroxide, which is volatile and instrument friendly. Over 90% enrichment efficiency was achieved in the proof-of-principle total cysteine analysis on MCF7 cell lysate.

The present tags exhibited only moderate increment residue mass on modification sites. DBA tag, especially for cDBA version, only introduce less than 300 Da mass increment on the modification sites after enrichment and elution, which is comparable to or even less than similar commercially available products. The small mass increment does not greatly affect the physical properties of enriched peptides such as solubility and chromatography retention time, but instead, the tertiary amine in the increment structure is able to enhance the ionization efficiency and boost signal response in MS analysis.

EXAMPLES

Example 1—Development of Cleavable DiLeu-Biotin-Azide (cDBA) Isobaric Tags to Enable Isobaric Tandem Orthogonal Proteolysis Activity-Based Protein Profiling (isoBOP-ABPP) Platform for High-Throughput Quantitative Chemical Proteomics and Pan-Post Translational Modification (PTM) Analysis In an aspect of the invention, the trifunctional architecture of the present tags, together with specific alkyne or DBCO probes, is able to simultaneously introduce isotopic labels onto desired molecules, such as onto the site of post-translational modifications (PTM) of peptides, and achieve selective purification or enrichment, making the present tags broadly applicable to the high-throughput quantitative analysis of a wide variety of low abundance PTMs based on activity-based protein profiling strategy, and accessible to a broad cross-section of researchers.

Both non-cleavable and cleavable versions of the present tags have been developed, in which a cleavable linker is introduced between the biotin derived moiety and the remnant structure of a cleavable DBA tag (cDBA). In a proof-of-concept total cysteine analysis of a complex biological sample, the performance of both DBA and cDBA tags was benchmarked, and comparable results of cDBA have been observed to a similar commercial product DADPS-Biotin-Azide. The high labeling efficiency and enrichment selectivity have been confirmed and enhanced fragmentation of reporter ions facilitate quantification at reduced collisional energies with unambiguous localization of the modification sites. These preliminary results demonstrate the potential of developing the DBA tags into a high-throughput quantitative pan-PTM analysis platform.

Multiplex sets are being synthesized and their applicability to various types of protein PTMs are being explored further. The present DBA tags are suitable for labeling, enrichment and LC-MS/MS analysis of PTMs using peptide and protein standards, peptide mixtures and complex biological protein extracts.

Example 2—Development of Cleavable DiLeu-Biotin-Azide (cDBA) Isobaric Tags and Isobaric Tandem Orthogonal Proteolysis Activity-Based Protein Profiling (isoBOP-ABPP) Platform for High-Throughput Quantitative Chemical Proteomics In view of the lack of versatile and high-throughput tools for studying PTMs, the present invention provides tagging reagents for the identification and quantification of PTMs globally in a high-throughput manner with economic cost and simple procedures. Moreover, accumulating evidence suggest abnormal S-nitrosylation of several proteins are involved in Alzheimer's disease (AD) pathogenesis. The present tagging reagents further allow for the study of how global S-nitrosylation profiles change in cerebrospinal fluids (CSF) during different stages of AD progression. Additionally, these tagging reagents offer versatile analytical capacity for various PTMs, and can be used to examine PTM crosstalk and elucidate how combinations of multiple PTMs can be generated and affect protein functions and interactions. These topics are summarized below and then discussed in greater detail.

Stage 1—The design and synthesis of multiplexed DiLeu-Biotin-Azide (DBA) tags and establishment of isobaric tandem orthogonal proteolysis activity-based protein profiling (isoBOP-ABPP) method to facilitate quantitative PTM analysis. Several candidates of DiLeu-Biotin-Azide (DBA) tag were synthesized, followed by systematic evaluation of the performance of these candidates including labeling/enrichment efficiency and fragmentation pattern in tandem mass spectrometry (MS/MS). The structure of the best candidate was then selected, and isotopic version of DiLeu incorporated to construct a set of isobaric multiplexed DBA tags.

Stage 2—Discovery and investigation of global S-nitrosylation in Alzheimer's diseases using multiplexed DBA tag based on quantitative proteomics approach for a better understanding of molecular mechanisms underlying neurodegenerative diseases. S-nitrosylation plays a pivotal role in many neurodegenerative diseases and the DBA tag offers a high-throughput quantitative tool for global analysis of S-nitrosylation. Quantitative proteomics is conducted using DBA tag on cells samples from AD mouse model and CSF samples from human patients. Bioinformatics analysis helps to identify differentially expressed proteins or modification sites as putative biomarkers or targets followed by subsequent biological validation.

Stage 3—Expansion of the scope of application of DBA tag and establishment of a pan-PTM high-throughput quantitative proteomics platform for various PTM study and crosstalk investigation. The utility of DBA tag is able to be expanded due to the design of its chemical structure and unique features of biorthogonal reactions. Besides various cysteine oxidation, protein carbonylation and citrullination are also amenable to chemical tagging. Thus, by altering alkyne probe to chemical selectively label different PTM sites, various PTM are able to be derivatized, captured, enriched (i.e., purified), and analyzed. The versatility of the application of DBA tag makes it an ideal pan-PTM high throughput quantitative analysis platform. Furthermore, the combination of different PTM constitutes the next level of complexity for proteomics research and this research field is able to benefit from a pan-PTM proteomics platform enabled by the present tags.

Nitrosative stress and the role of protein S-nitrosylation in AD. Numerous studies suggest that the dysregulated redox signaling is crucial in the pathophysiology, inflammatory responses and neuroprogressive nature of major depression (13-15). Reactive oxygen and nitrogen species (ROS and RNS), including peroxynitrite, superoxides, peroxides and nitric oxide (NO), are produced during normal physiological processes and through interacting with proteins, fatty acids and DNA, perform numerous roles in regulation of cellular function. However, excess ROS/RNS can lead to structural and functional changes resulting in cellular injury. These potentially toxic effects are offset under normal physiological conditions by intrinsic antioxidant mechanisms but increased oxidative and nitrosative stress (O&NS) may cause damage to cellular components, induce harmful autoimmune responses, and ultimately lead to failure of normal cellular processes.

NO, as an important RNS, is a small, highly diffusible signaling molecule generated by three different isoforms of NO synthase (NOS) from L-arginine and NADPH in mammalian cells (16). NO induces a PTM of proteins, called S-nitrosylation. S-nitrosylation is formed via the reaction of NO with thiyl radical or between NO+, which is one electron oxidized form of NO, and the thiol group of cysteine residues in the target protein (17). This nitrosylation reaction forms an S-nitrosothiol (—SNO) and is commonly reversible. It is important to note that S-nitrosylation has unequivocally been shown to function not only in redox homeostasis and toxicity, but also in conveying or regulating physiological cellular signals (18).

Elevated levels of nitrosative stress were found in human AD brains (19). Genetic mutations associated with neurodegenerative diseases, environmental toxins such as certain pesticides, and misfolded proteins including Aβ oligomers can all lead to excessive nitrosative stress. The resulting aberrant S-nitrosylation of numerous proteins has been implicated in the pathogenesis of several neurodegenerative disorders. For example, S-nitrosylation of XIAP and PDI can cause 'loss-of-function' by impairing E3 ligase ubiquitin ligase activity and molecular chaperone activity, respectively (20, 21). These processes can contribute to accumulation of neurotoxic proteins and activation of apoptotic pathways. Additionally, oligomeric Aβ peptide can result in increased generation of NO and S-nitrosylation of Drp1, resulting in excessive mitochondrial fragmentation, bioenergetic compromise, and consequent synaptic damage. Additionally, Cdk5 is activated when Aβ increases calpain activity to cleave the Cdk5 regulatory subunit p35 to p25. The resulting neurotoxic kinase activity of Cdk5 is further enhanced by S-nitrosylation. Formation of SNO-Cdk5 may also contribute to spine loss by transnitrosylating Drp1, with the resultant SNO-Drp1 participating in mitochondrial fragmentation (22-24). Overall, aberrant S-nitrosylation can trigger many neurodegenerative signaling pathways. Here, novel chemical proteomics methods are utilized to investigate S-nitrosylation and study its role in Alzheimer's diseases.

Isobaric tandem orthogonal proteolysis activity-based protein profiling (isoBOP-ABPP). While human genome sequencing and genetics enable making direct connections between mutations and human disorders at an unprecedented rate, there has been a widening gap between the number of genes and their encoded proteins that have been linked to health and diseases. As a matter of fact, only around 2% of all predicted human gene products are currently targeted with small-molecule drugs and only 10-15% of all human proteins are 'druggable,' with only a 25% overlap between druggable protein targets and known disease-modifying targets (25, 26). This discrepancy is in part because many proteins may not have any obvious binding pocket for pharmacological interrogation or because of a lack of high throughput screening technologies for functional assays to identify small-molecule modulators against these targets. The advent of advanced strategies of chemical proteomics and the activity-based protein profiling (ABPP) approach has empowered significant expansion of the scope of proteins that can be pharmacologically evaluated in living systems, thus promoting identification and prioritization of new therapeutic targets (27-30).

Figure 2:
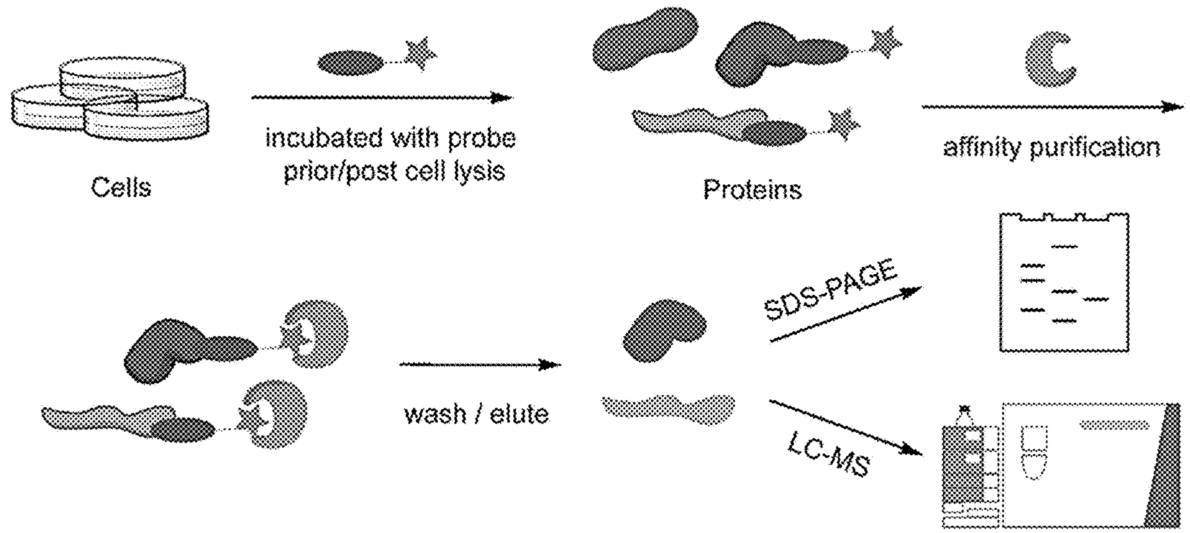
FIG. 2 shows a general workflow for activity-based protein profiling (ABPP) target identification.

In a typical ABPP experiment for target identification, ABPP probes are first incubated with living cells or cell lysates (FIG. 2), along with appropriate negative controls (such as DMSO, inactivated drug, or the original compound in competitive assays). Following target protein binding (based on specific activity between probe and substrate proteins), the probe-protein complexes are enriched through affinity purification against the probe. Next, nonspecific binding proteins are removed through multiple washes before target proteins are eluted. The protein targets are then identified with methods including gel electrophoresis and MS. The use of negative controls allows for relative quantification and mitigates the interference of background and nonspecific binding proteins to some extent. ABPP probes generally have three fundamental components: (i) a reactive group for binding or modifying the target proteins at certain sites, such as the active sites of a given enzyme class or the drug-binding pockets; (ii) a reporter moiety for identification and purification of binding proteins; (iii) a linker, occasionally cleavable, extending the distance between the reporter and the reactive group to avoid steric hindrance (31, 32).

Uniquely, Cravatt and colleagues designed an isotopic tandem orthogonal proteolysis-activity-based protein profiling (isoTOP-ABPP) strategy to profile the intrinsic reactivity of cysteine residues in native proteomes (33, 34). The isoTOP-ABPP approach employed biorthogonal reaction—the copper(I)-catalyzed azide/alkyne cycloaddition (CuAAC) reaction—to bridge the probes and proteins which have been modified with precursor alkyne handle molecules in advance. In addition, the linker containing a tobacco etch virus (TEV)-protease recognition peptide could be efficiently cleaved after enrichment and the isotopically labelled valine could be used for relative comparison in MS measurement (35). However, the bulky nature and synthetic complexity of its chemical structure limited its widespread application and the quantification strategy using isotopic labeling based on MS1 limited its multiplex capacity.

By incorporating isobaric labeling strategy based on fragment ions in MS/MS scan, high-throughput quantitative analysis can be achieved. Commercially available tandem mass tags (TMT/TMTpro) and isobaric tags for relative and absolute quantitation (iTRAQ) have become a mainstream technique in relative protein quantification by examining up to 16 biological samples simultaneously in a single liquid chromatography mass spectrometry (LC-MS) run (36-38). The in-house-constructed N,N-dimethyl leucine (DiLeu) tags are a cost-effective alternative to TMT and iTRAQ tagging approaches (39). The ABPP approach and DiLeu isobaric labeling strategy are combined to establish a novel method coined isobaric tandem orthogonal proteolysis activity-based protein profiling (isoBOP-ABPP) to achieve targeted protein screening as well as high-throughput quantitative analysis.

Pan-PTM high-throughput quantitative proteomics platform. As PTMs play important roles in many physiological and pathological processes, accurate and convenient analysis of each type of PTM is of high significance and relevance. However, due to the various types of PTMs and their diverse functions and localizations on proteins, there is no universal method capable of analyzing every/each type of these PTMs. Most PTMs can be detected by MS-based proteomics, either as a mass increment or a mass deficit relative to the nascent unmodified protein, and MS/MS enables characterization of modified proteins via amino acid sequencing and site-specific localization of post-translationally modified amino acid residues. But the general low abundance of PTMs usually require upstream enrichment to aid LC-MS analysis, where different strategies including affinity purification, antibody recognition and chemical modification are employed (40-45). Moreover, MS is not inherently quantitative, which demands the introduction of stable isotopes into the analytes of interest based on stable isotope dilution principle (46, 47). With the development of biorthogonal reaction, artificial chemical probes could be incorporated into biomolecules with greater flexibility and hence more sophisticated architecture of the chemical structures could be designed and implemented. Here, a pan-PTM high-throughput quantitative proteomics platform is created based on the isoBOP-ABPP method integrating selective PTM probing, efficient PTM enrichment, and isobaric labeling for quantification that allows versatile PTM analysis and potential application to the study of PTM crosstalks in complex biological systems.

Methods and Approaches. Multiplexed Quantification with DiLeu Isobaric Tags.

4-plex DiLeu isobaric tags. DiLeu tags were originally developed as a novel, cost-effective alternative to commercial isobaric tags (e.g., iTRAQ, TMT) (48). The structure of DiLeu resembles other isobaric tags in that it features a reporter group, a mass-balance group, and a reactive group for labeling of primary amines on peptide N-termini and lysine side chains. The first generation of the 4-plex DiLeu isobaric tags yield reporter ions at m/z 115, 116, 117, and 118 upon MS/MS analysis of labeled peptides. The multiplex set can be synthesized in-house using established chemistry in only a few steps with significant cost savings, while offering excellent labeling efficiency and enabling accurate relative quantification (49, 50).

Mass defect-based 12-plex DiLeu isobaric tags. The multiplexing capacity of the DiLeu reagent was recently expanded to enable simultaneous quantification of up to twelve samples in a single MS/MS spectrum using high-resolution MS platforms (49). The tags were modified to include the concept of neutron encoding (NeuCode) method originally developed by Coon and colleagues (51). Mass defect, the cause of a subtle mass change, arises from the fact that nuclear binding energy, the energy required to break down a nucleus into its component nucleons, is different for each isotope of every element (52). Through calculated incorporation of 13C, 15N, and 2H stable isotopes in the reporter structure, eight additional reporter isotopologues were able to be designed that differ in mass from the original four reporters by −6 mDa to yield an isobaric 12-plex set consisting of two 115 labels, three 116 labels, three 117 labels, and four 118 labels. In doing so, the multiplexing capacity was tripled without increasing synthetic complexity or requiring custom isotopic reagents. Resolving each of the 12-plex DiLeu reporter ions requires an MS/MS resolving power (RP) of at least 30,000 (@ 400 m/z), which is readily approachable for modern orbitrap mass spectrometer. Multiplexing offers the ability of parallel sample processing, thereby reducing the number of MS runs and increasing the overlap of proteins detected and quantified across many experiments. In addition, the concise chemical structure of DiLeu and simple synthetic scheme offer a great opportunity for further developing them into advanced architecture for sophisticated applications (53, 54).

Design and synthesis of the prototype of DBA tag and evaluation of its performance. The DBA tag of this embodiment has three unique features: (i) It contains a biotin moiety which is widely used as an enrichment group. The biotin-streptavidin interaction is the strongest noncovalent biological binding known so far, having a dissociation constant, Kd, in the order of $4\times10^{-14}$ M. The strength and specificity of the interaction render it to be one of the most widely used affinity pairs in molecular, immunological, and cellular assays (55); (ii) It contains an azide group which serves as a conjugation site for alkyne modified molecules, where copper(I)-catalyzed azide/alkyne cycloaddition (CuAAC) reaction, known as click chemistry, is readily performed with high efficiency (56, 57); (iii) It contains a DiLeu moiety as a reporter group, which would facilitate MS/MS based relative quantification. Combining all three features together, various chemical structures can be conceived; considering synthetic difficulty, one of the most concise and simplified structure was chosen and synthesized as a prototype (illustrated in FIG. 3).

This prototype DBA tag has a linear structure, in which one end is the biotin moiety for enrichment and the other end is DiLeu reporter ion, with an azide handle branched out in the middle. It can be made with four steps of simple organic reactions at moderate yield, which is relatively easily accessible for common analytical lab settings. In addition, the incorporation of DiLeu reporter ion group was set as the final step for the synthetic route, which is intended for modularized synthesis of multiplex isotopic channels. To evaluate its performance, MS/MS of the tag itself was performed under higher collisional dissociation (HCD) mode at normalized collision energy (NCE) 30, intense reporter ion signal was observed corresponding to the cleavage of DiLeu and biotin fragments. Both of these two peaks could be used as signature of modification. For chemical labeling condition, standard click chemistry protocol utilizing CuSO4 and sodium ascorbate to general Cu(I) in situ which catalyzed alkyne and azide cycloaddition was employed (58). The alkyne modified biomolecules were prepared using standard peptide—atrial natriuretic peptide (ANP)—which contains a free cysteine residue in the middle of the sequence and thiol-reactive probe 2-indo-N-(prop-2-yn-yl)acetamide (IPM). The reaction parameters such as concentrations for the substrates, reaction temperature, and reaction time were further optimized.

Figure 4:
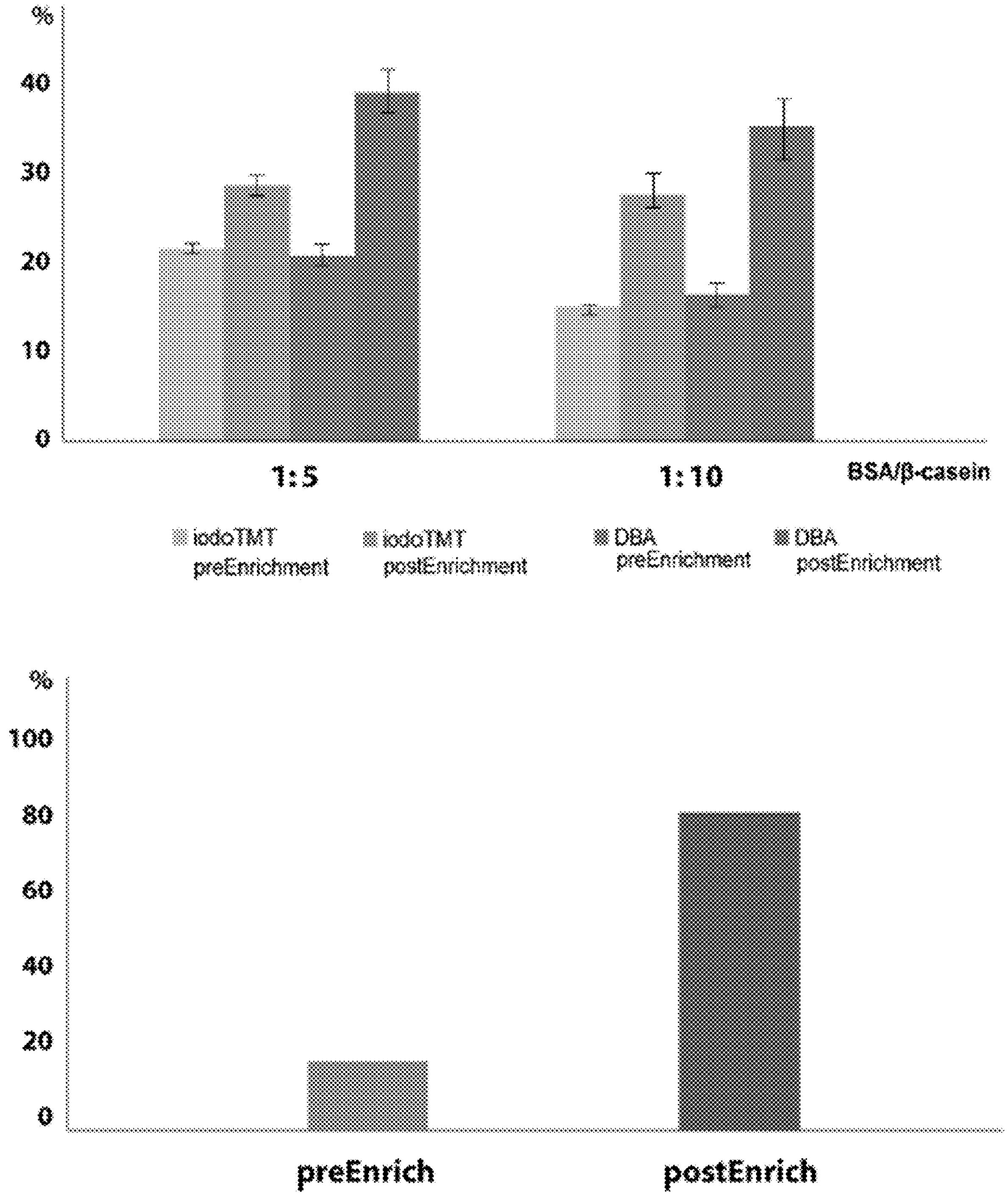
FIG. 4 shows enrichment efficiency comparison between DBA tag and iodoTMT (top) and total cysteine analysis in HeLa cell lines (bottom). Tryptic digested BSA was spiked into tryptic digested β-casein with a ratio at 1:5 or 1:10. The y-axis represents the percentage of cysteine-containing peptides/total peptides.

Enrichment efficiency comparison between DBA tag and iodoTMT and total cysteine analysis in HeLa cell line. As mentioned above, the DBA tag possesses three unique features, among which the most useful and distinct one is enrichment enabled by biotin-streptavidin interaction. According to the design, alkyne-modified biomolecules are converted to DBA probe derivatized form, thus containing biotin moiety and could be captured by streptavidin modified solid phase extraction (SPE). Those non-alkyne-modified molecules are washed off and discarded. To investigate the enrichment efficiency, two model proteins—bovine serum albumin (BSA) and β-casein—were used. BSA has multiple cysteine residues within its sequence, while β-casein only has one cysteine residue in its sequence. When spiking tryptic digested BSA to abundant β-casein, cysteine residues only exist as a minor portion of total peptides. By using IPM (an IAA-like alkyne molecule) to label BSA/β-casein mixture, cysteine residues were installed an alkyne handle, which were then conjugated to the DBA tag through click chemistry. Enrichment efficiency can be calculated by taking ratio of abundance of cysteine containing peptides/total peptides. IodoTMT is a set of commercially available isobaric tags that enable multiplexed quantification of cysteine-containing proteins using tandem mass spectrometry (59, 60). Therefore, the DBA tags were compared against iodoTMT. As shown in FIG. 4, DBA tag exhibited comparable or slightly better enrichment performance compared to iodoTMT.

In addition, among the many developed methods for the detection of SNO, the biotin switch technique (BST) reported by Jaffrey et al. is the gold standard (61). BST and its various modified forms represent indirect detection strategies, in which S-nitrosothiols are selectively reduced with a mild reducing reagent (e.g., ascorbate) and labeled with another tag forming a stable bond for further detection, enrichment, or quantification on the same site (62, 63). Therefore, by performing total cysteine analysis in proteome, the potential application of DBA tag to probe SNO could be assessed. HeLa cell lines were used as complex biological samples. Around 15% of tryptic peptides are cysteine containing peptides in *Homo sapiens* (64), this was validated by cysteine analysis without enrichment (FIG. 4, bottom). After DBA tag labeling and enrichment, majority of peptides were removed, and the percentage of cysteine-containing peptides could reach to above 80%. This result suggested that this new approach provides the capability to identify protein S-nitrosylation sites and quantify changes in S-nitrosylation PTMs by mass spectrometry.

Optimization of instrumental parameters for DBA tag labeled peptide analysis. Liquid chromatography-tandem mass spectrometry (LC-MS/MS) strategies are frequently used to identify specific PTMs. However, labile PTMs such as S-nitrosylation are unstable during collisional induced fragmentation, thus requiring certain chemical derivatization. Chemical derivatization can not only stabilize the primordial modification sites but also change chemical physical properties of peptides on LC and/or MS. Detailed optimizations of instrumental parameters are necessary for obtaining optimal analysis results (65). PTM analysis was performed on Orbitrap Fusion Lumos, a commercialized tribrid mass spectrometer, where precursor ions can be isolated in either quadrupole (Q) or ion trap (IT), and the fragment product ions can be analyzed in both low-resolution ion trap and high-resolution Orbitrap analyzers (66). This lays the foundation of isobaric quantification based on minute mass differentiation of fragment ions. Higher resolution can increase mass accuracy and the sensitivity of low abundance precursor ion detection but decrease the data acquisition rate. Thus, there is always a trade-off between mass spectral resolution and instrument duty cycle. Many other parameters including mass resolution, maximum injection time, isolation window, automatic gain control (AGC) target of MS2 and normalized collision energy (NCE) were screened and optimized further. All the optimizations were performed in top speed mode, which could maximize the number of high-quality MS spectrum acquisition within each duty cycle. Selected reaction monitoring (SRM)—also called multiple reaction monitoring—is emerging as a targeted proteomics approach that a predefined precursor ion and one of its fragments are selected by the two mass filters and monitored over time for precise quantification (67). DBA tag labeled peptides typically generated signature fragments of DiLeu during MS/MS, which commonly used as reporter ions for relative quantification, but could also be utilized for SRM method development. In addition to characteristic reporter ion, those unique precursor peptides representing targeted proteins are essential information need to know in advance.

Results and Discussion

Design and synthesize of multiplexed DiLeu-Biotin-Azide (DBA) tag and establish isobaric tandem orthogonal proteolysis activity-based protein profiling (isoBOP-ABPP) method to facilitate quantitative analysis of post-translational modifications (PTM). Chemical proteomics, in particular activity-based protein profiling (ABPP), combining with bio-orthogonal click chemistry, is widely utilized both in vitro and in vivo (68-71). ABPP is an ideal strategy that can faithfully recapitulate protein-small molecule interactions in situ (i.e., in live cells), and tandem orthogonal proteolysis-activity-based protein profiling (TOP-ABPP) employs on-bead trypsin and TEV digestions to simultaneously identify both probe-labelled proteins and their exact sites of probe modification at the same time (72, 73). However, the bulky structure of the tag in classical isoTOP-ABPP and the reliance on full-MS quantification has limited its usage in broader PTM proteomics studies and high-throughput analysis. Here, in-house constructed DiLeu isobaric tags were incorporated into the structure of a novel chemical probe, DBA tag, establishing an isobaric tandem orthogonal proteolysis activity-based protein profiling (isoBOP-ABPP) method to overcome the limitations of isoTOP-ABPP.

Figure 5:
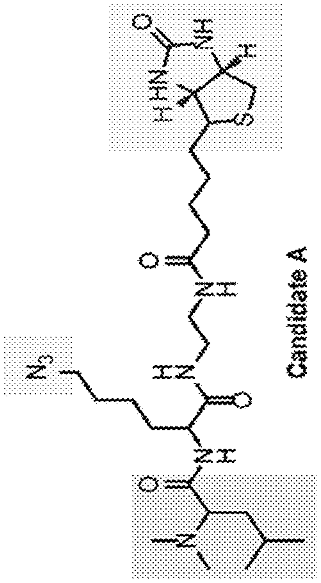
FIG. 5 shows the chemical structures of DBA tag candidates in an embodiment of the invention with the DiLeu, Biotin and Azide groups shaded.
Figure 5:
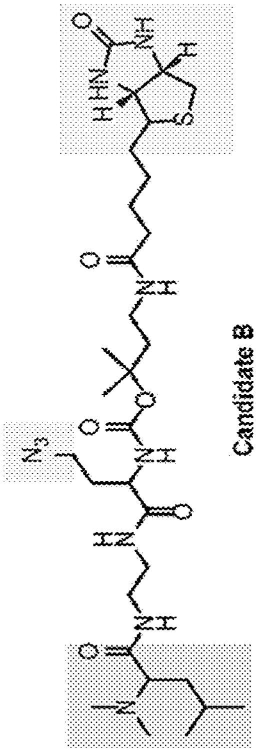
Figure 5:
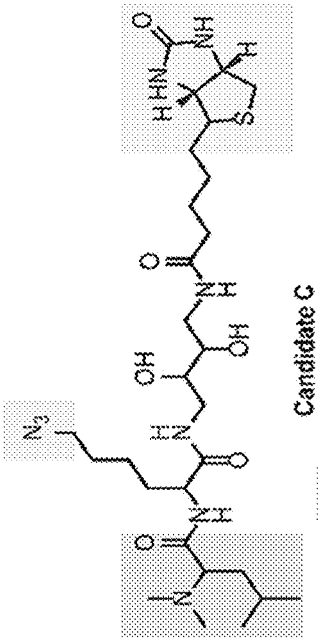
Figure 5:
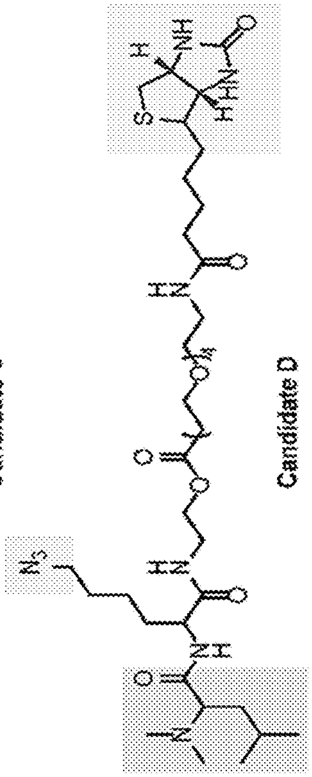
Figure 5:
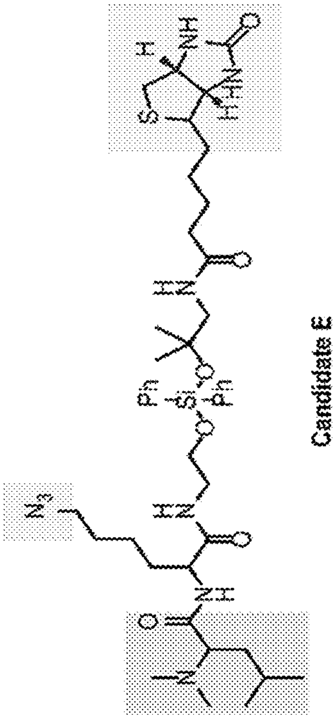

As shown in FIG. 5, several candidates are designed and synthesized as the prototype of DBA tags (protoDBA). DBA tag contains three parts: (i) DiLeu as reporter ion in MS/MS; (ii) biotin moiety for streptavidin enrichment and (iii) an azide group for probing alkyne-modified substrates through CuAAC click chemistry. The general architecture of the tag is a linear molecule with a short side chain. DiLeu and biotin groups are placed on two ends of the molecule with azide functionality left at the terminus on the side chain. Candidate A is the most compact one containing only three essential moieties bridged by an ethanediamine as a linker. While candidates B-E possess an extra feature, a cleavable linker between biotin and DiLeu/azide groups. This is for efficient and convenient release of captured biomolecules from the biotin-streptavidin complexes. Although there were reports suggested that the biotin-streptavidin interaction could be broken to recover intact biotin and streptavidin parts respectively (74, 75), it seems that the mainstream techniques tend to avoid putting cumbersome biotin parts on the conjugates before LC-MS/MS (76-79). Therefore, two different structures were designed for the cleavable DBA tag. Candidate B has an acid sensitive linker mimicking amine protecting group Boc which could be hydrolyzed under acidic condition, whereas candidate C contains a diol group which can be cleaved upon mild peroxide oxidation (such as $NaIO_4$). Candidate D possess a basic labile ester linker which can be facilely released under mild and volatile basic environment—5% ammonium hydroxide ($NH_4OH$), and candidate E has a popular cleavable linker DADPS which is acidic labile and utilized in many chemical probes. Some other candidates such as the one with photocleavable linker can also be proposed (80). After candidates are synthesized, their performance was evaluated using peptide standard and the optimal structure shall then be determined.

Design and synthesize the prototype DBA tags in a compact form and concise manner. The general architecture of DBA tag is designed as a linear molecule with two essential parts-DiLeu and biotin groups—on each end of it, while the azide moiety is at the terminus of the side chain. This design borrows from the first chemical in vitro labeling method that uses a biotin tag to label proteins containing cysteine residues, isotope-coded affinity tag (ICAT) (47, 81). The major novelty is modular synthetic design which makes incorporation of isotopes facile and straightforward. The construction of backbone structure starts from biotin acid, through amide coupling reaction, the structure is extended allowing functionalities to be installed. Tactfully, the fusion of DiLeu group is the last step, where isotopic version of DiLeu could be utilized for the synthesis of multiple channels of isobaric DBA tag. Considering the difficulty of recovering biotin from streptavidin beads, in addition to a compact structure Candidate A, another four cleavable structures (Candidates B-E) were designed, in which either acid/base hydrolysis or mild oxidation could be performed to efficiently remove biotin moiety from the conjugated biomolecules.

Figure 6A:
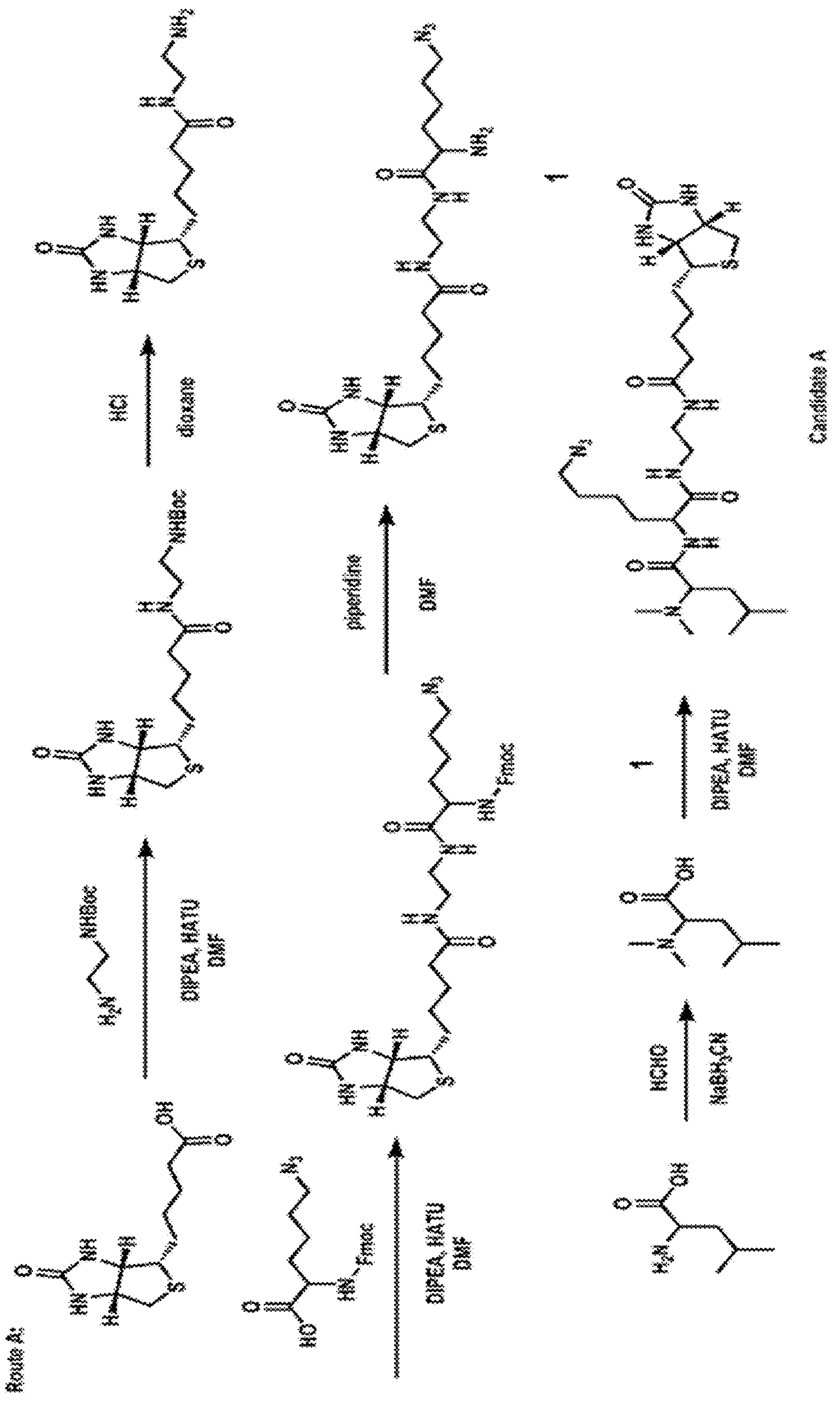
FIG. 6*a* shows synthetic routes of DBA tag candidate A and B (candidate A: non-cleavable protoDBA tag; candidate B: DBA tag with an acid cleavable linker).
Figure 6A:
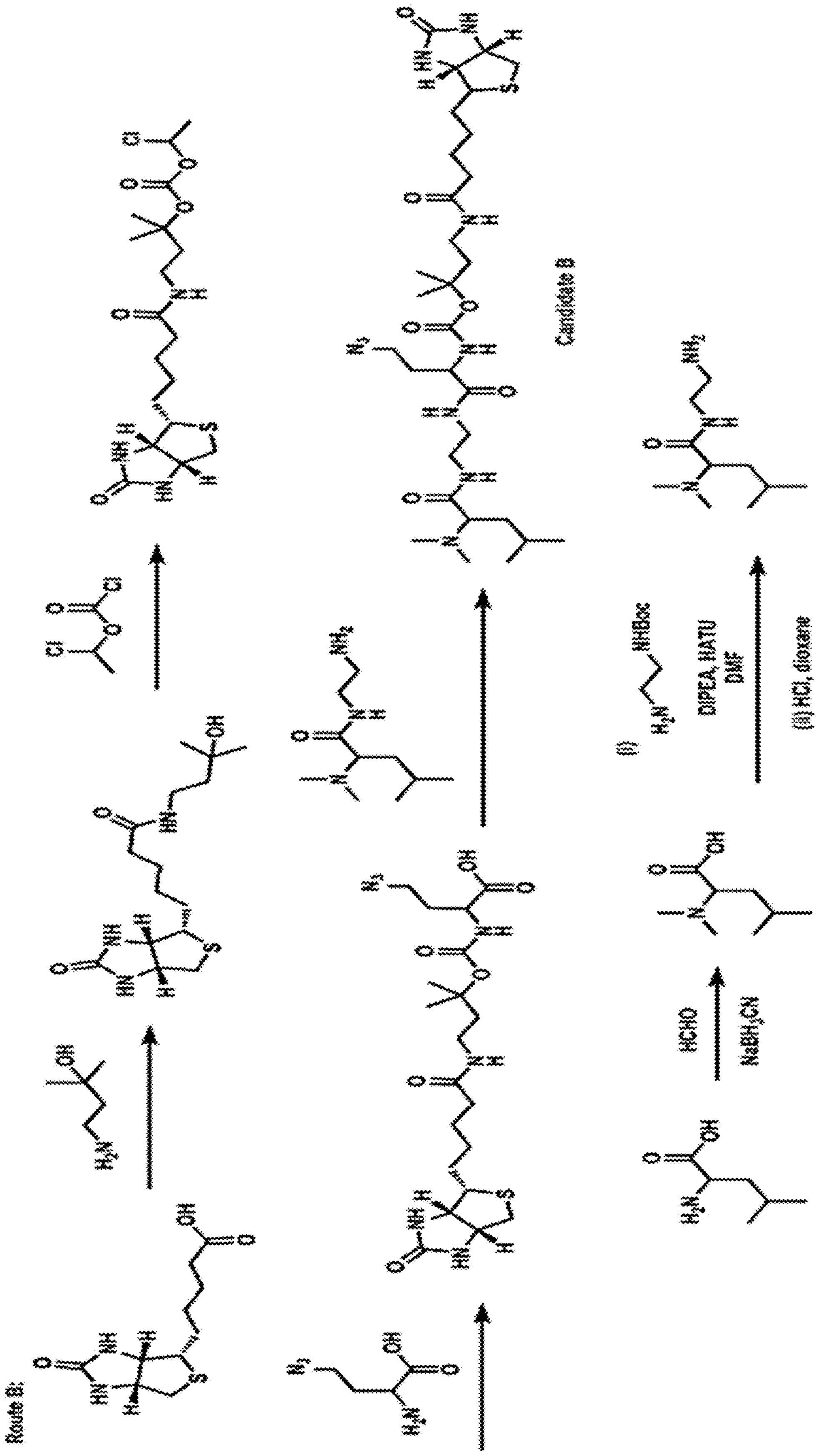

Synthesis of Candidate A. Biotin acid was coupled with N-Boc-ethylenediamine firstly before the Boc protecting group was removed in acidic condition. The biotin-amine was then coupled with a 6-Azido-N-Fmoc-lysine to produce a biotin-azide module 1 after deprotecting Fmoc group. At last, dimethylated leucine was installed onto 1 to make the final product Candidate A. It takes six steps in total and by far is the shortest synthetic route to make a compact DBA tag. (FIG. 6*a*, Route A).

Synthesis of Candidate B. Tertiary alcohol was introduced into biotin acid first. The acid cleavable moiety, while requiring an electrophilic locus, also necessitated the presence of a terminally protected primary amino group for the attachment of the remaining DiLeu-Azide part. To this end, utilizing chlorocarbonate reagent was envisaged for modifying tertiary alcohol which could be substituted subsequently by an azide amino acid (82). When azide module is installed, DiLeu group shall be incorporated lastly. In brief, N-Boc-ethylenediamine is used to convert carboxyl group of DiLeu into an amine functionality, after which the condensation between amine on DiLeu module and carboxyl group on Biotin/Azide module could be implemented to afford the final product. The overall route takes seven steps. (FIG. 6*a*, Route B).

Figure 6B:
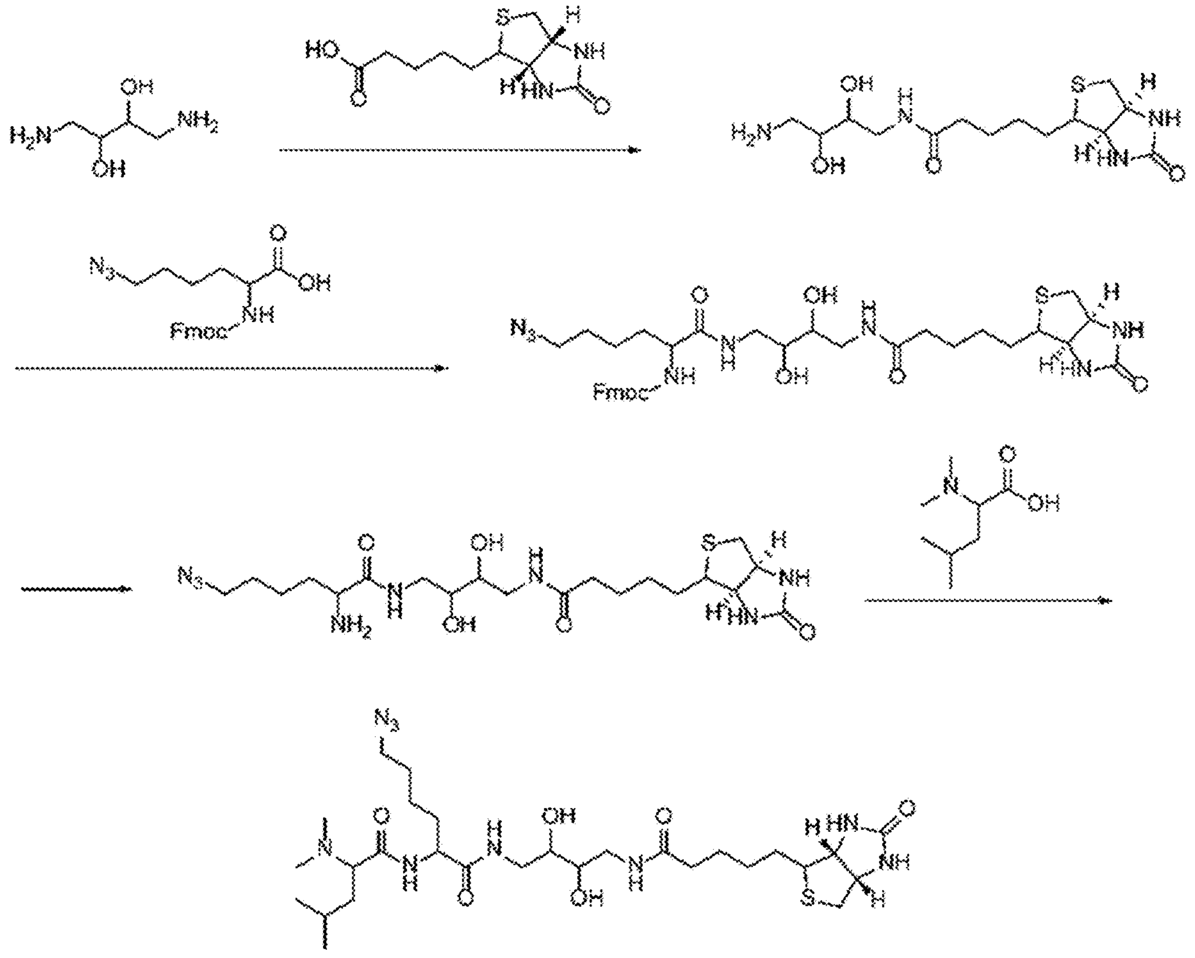
FIG. 6*b* shows synthetic routes of DBA tag candidates C-E (candidate C: cleavable DBA tag with a diol linker; candidate D: cleavable DBA tag with a base cleavable linker, candidate E: cleavable DBA tag with DADPS linker).
Figure 6B:
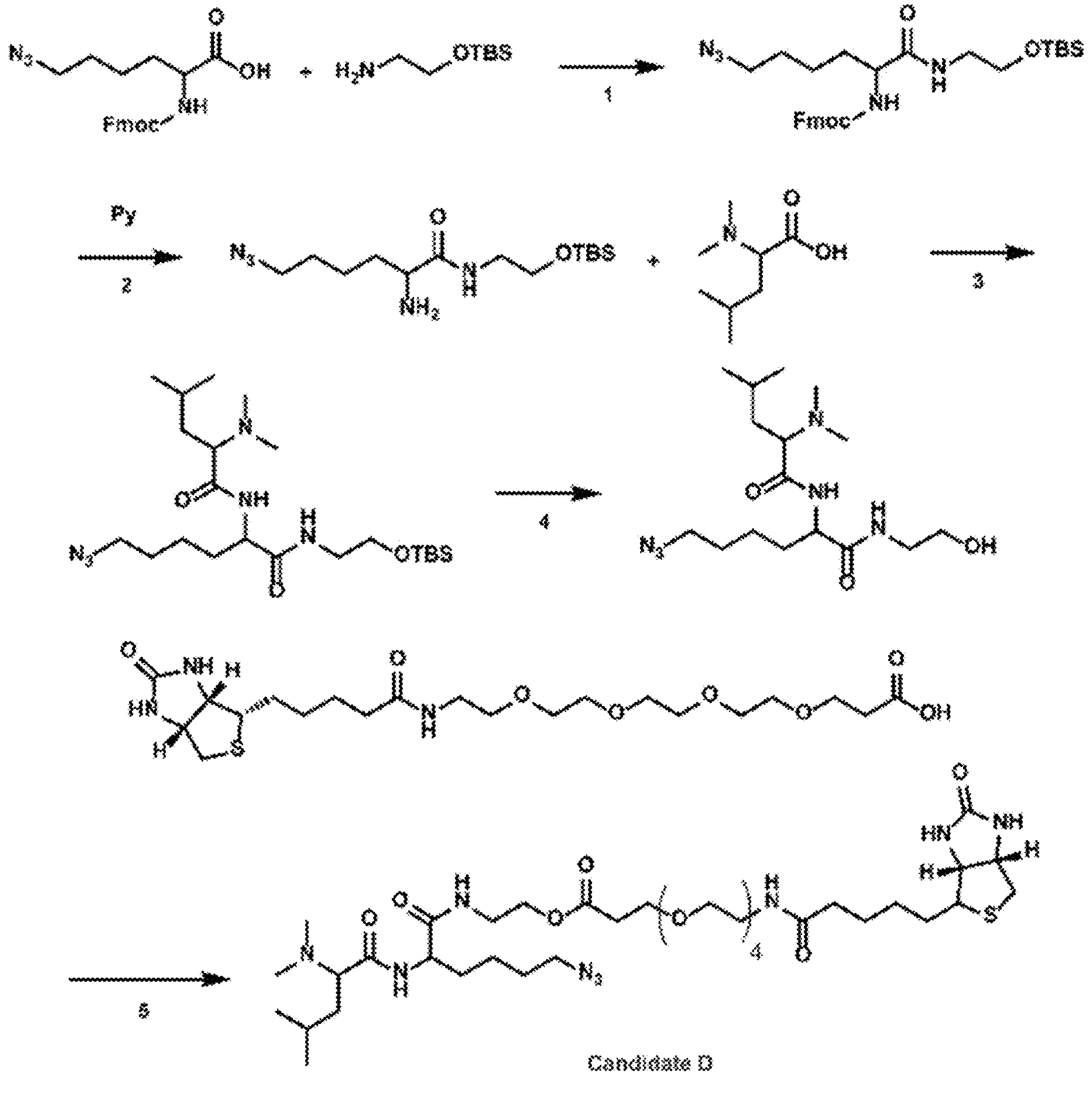
Figure 6B:
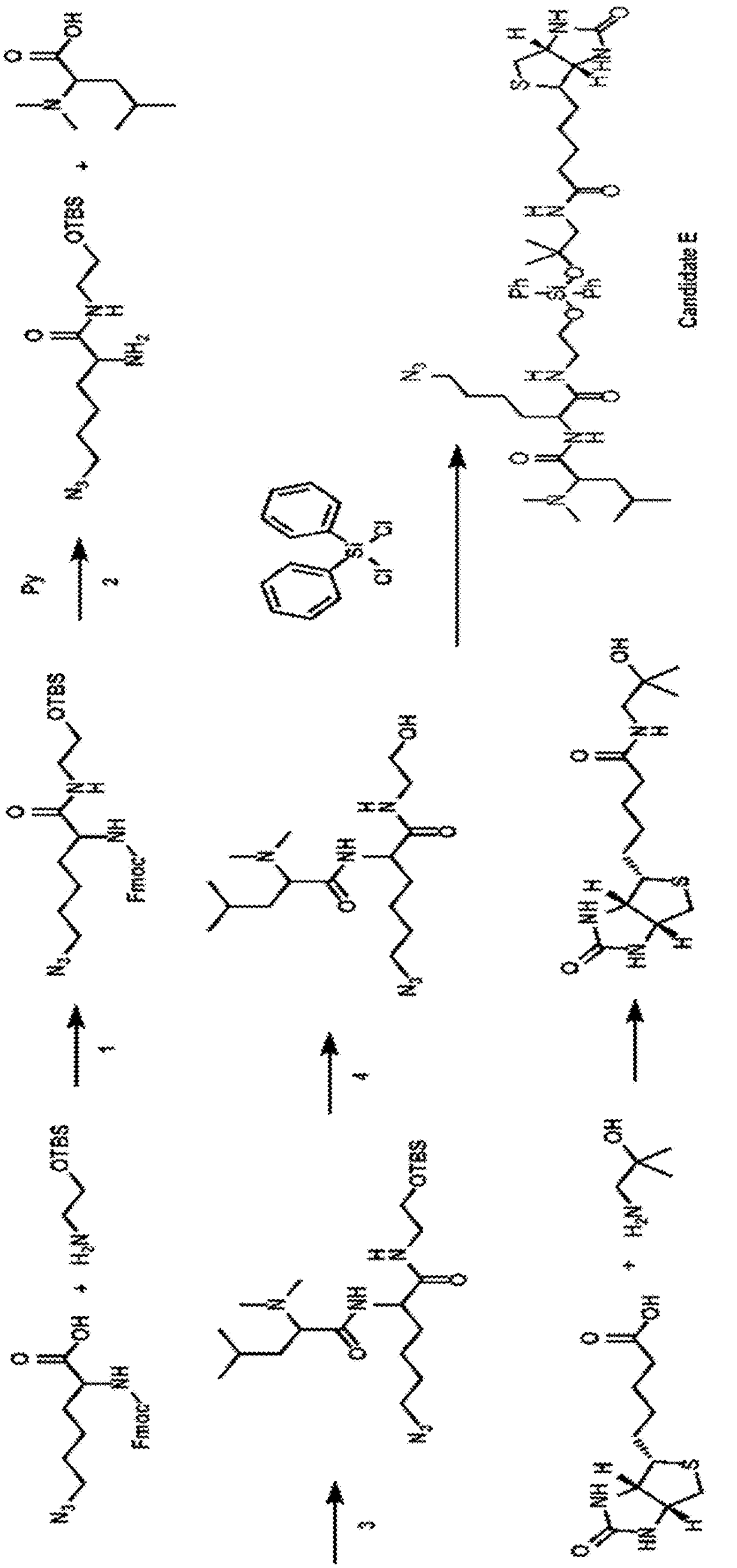

Synthesis of Candidate C. Photocleavable linker (83) and diol linker are both widely adopted cleavable linker in chemical proteomics. To synthesize a DBA tag with a diol linker, 1,4-diaminobutane-2,3-diol was used as the core. By using amide coupling, the core can be extended with biotin and azide lysine to produce the precursor intermediate. Then the intermediate product was deprotected before labeling with DiLeu to get the final product. The route takes four steps in total. (FIG. 6*b*, Route C).

Synthesis of Candidate D and E. The candidate D and E shared same synthetic route in part. The DiLeu was conjugated to azide lysine first following two-step amide coupling and two-step deprotection reaction. The intermediate product with a primary alcohol group was then linked with either a carboxylic acid to afford an ester or labeled with DADPS to afford a base labile cDBA tag. The two routes take five or six steps, respectively. (FIG. 6*b*, Routes D and E).

Evaluation of the performance of prototype DBA tags and determination of the optimal structure. As mentioned above, the designed DBA tag possesses three characteristics: efficient labeling against alkyne group by click chemistry; competent enrichment performance provided by biotin-streptavidin interaction, and unique DiLeu reporter ion generated in MS/MS for relative quantification. Therefore, the performance of synthesized candidates would be evaluated from the following aspects: (i) labeling condition and efficiency; (ii) enrichment efficiency and (iii) fragmentation behavior in MS/MS. Standard peptides or proteins could be used for evaluation and the one with the best performance will be chosen as the optimal structure of DBA tag.

Figure 7:
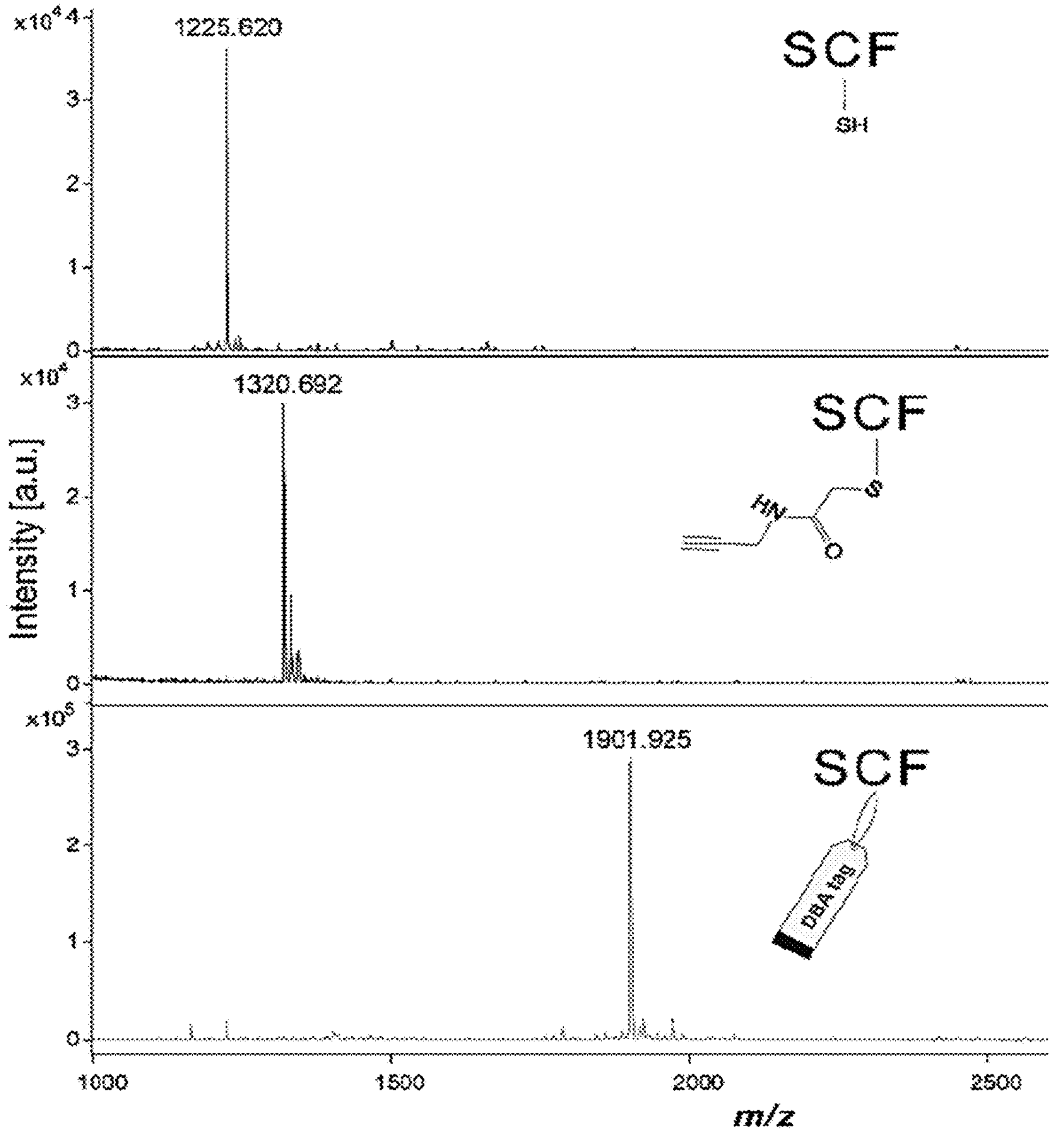
FIG. 7 shows DBA tag labeling condition and performance evaluated using standard atrial natriuretic peptide (ANP), which contains a free cysteine residue in the middle of the sequence (shown here as amino acids SCF), by MALDI-TOF MS. Results acquired using Candidate A (top: native ANP peptide; middle: ANP labeled by IPM; bottom: ANP labeled by protoDBA candidate A).
Figure 7:
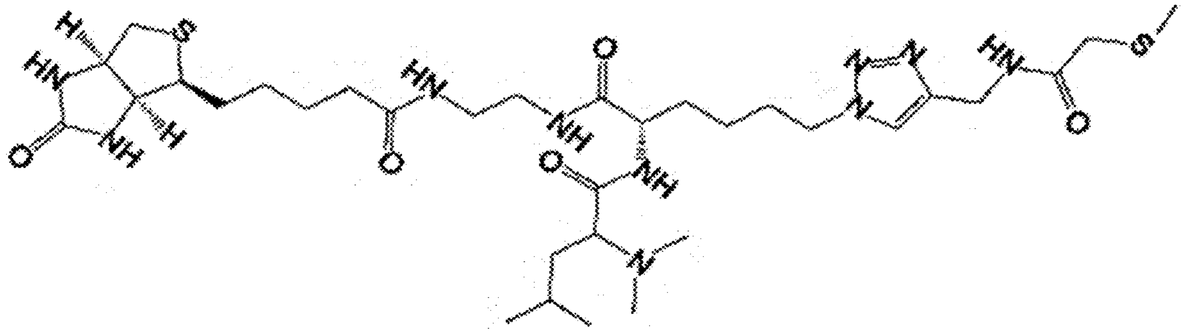

Labeling condition and efficiency. Atrial natriuretic peptide (ANP) was used as a standard peptide for method development and labeling condition optimization. ANP is a natriuretic peptide hormone secreted from the cardiac atria and the main function of ANP is causing a reduction in expanded extracellular fluid (ECF) volume by increasing renal sodium excretion (84). The first 28 amino-acid sequence contains a disulfide bridge (Cys:7-23), in which a shorter peptide with a free cysteine residue in the middle of its sequence could be prepared through reduction and digestion. This segment of ANP was labeled by IPM first to convert thiol group on cysteine residue into an alkyne handle, and protoDBA was then tagged with alkyne modified ANP segment through CuAAC click chemistry. The labeling conditions including substrate concentrations, choice of metal ligands, temperature, reaction time etc. were screened and carefully optimized as in previous studies (85, 86). The reaction was monitored by matrix-assisted laser desorption/ionization-time of flight mass spectrometry (MALDI-TOF MS). As shown in FIG. 7, both alkylation and click chemistry exhibit excellent labeling efficiency. Mass spectral peaks corresponding to the modified mass were clearly observed with minimal signal of reactant barely detected. This result suggests the high efficiency of click chemistry and thiol alkylation, making it readily applied to cysteine modification analysis.

Figure 8:
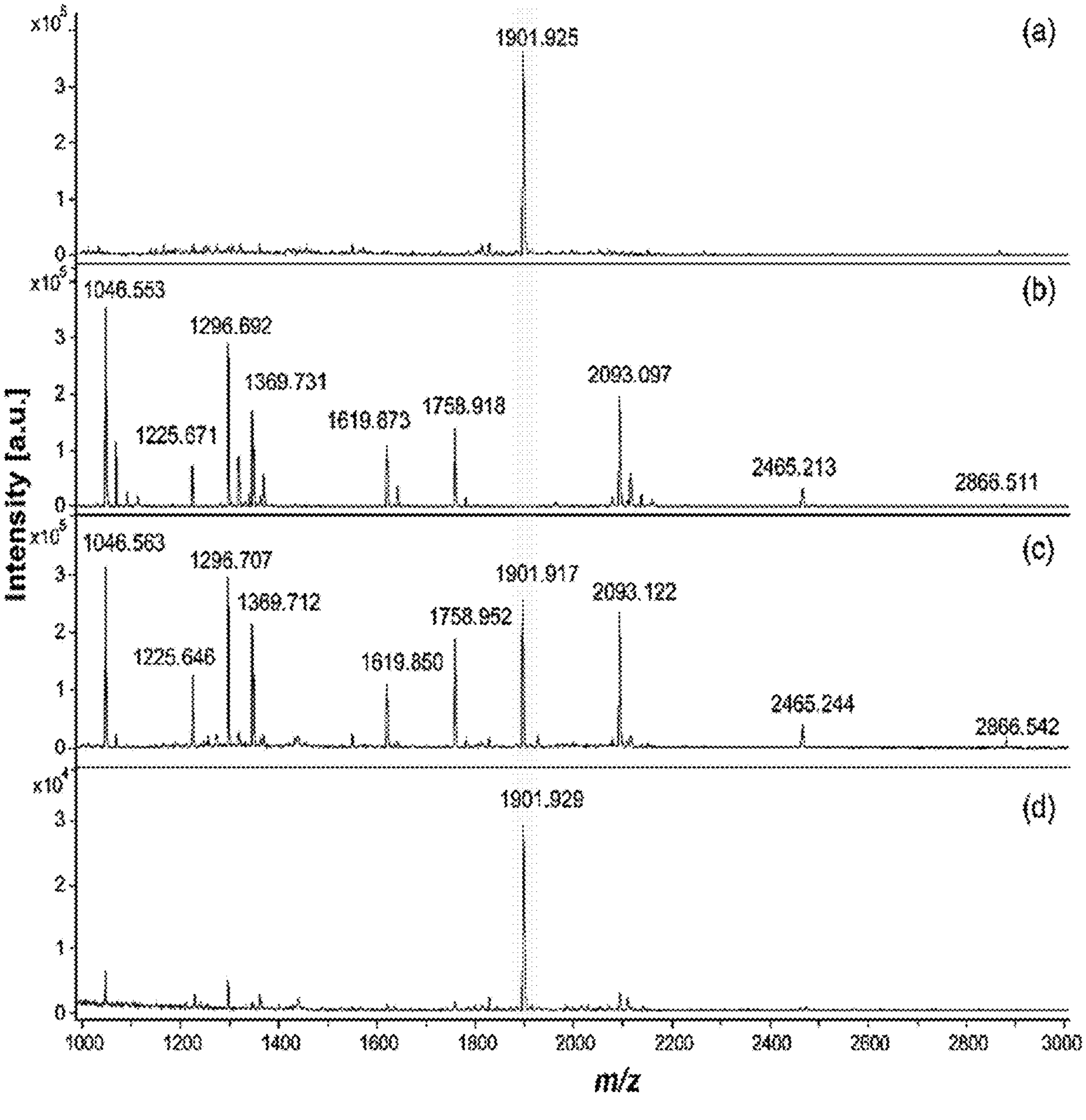
FIG. 8 shows enrichment efficiency evaluation on peptide mixture (panel a: ANP labeled by protoDBA candidate A; panel b: peptide mix; panel c: labeled ANP spiked into peptide mixture before enrichment; panel d: after enrichment).

Enrichment efficiency. Enrichment performance was evaluated at the peptide level first. By spiking protoDBA labeled ANP peptide (FIG. 8, panel a) into a peptide mix (FIG. 8, panel b), the new peptide mixture constitutes an ideal environment for enrichment performance test (FIG. 8, panel c). Because only modified ANP contains a biotin group, the other peptides cannot be bonded onto streptavidin beads and were washed away. Only protoDBA labeled ANP was preserved in elution buffer (FIG. 8, panel d). To test enrichment performance on a more general level, standard proteins BSA and β-casein were used. Tryptic digestion was performed first on both proteins and then BSA was spiked into β-casein at 1:5 and 1:10 ratio. Since BSA is rich of cysteine residues within its sequence while β-casein barely contain any cysteine residue. When performing enrichment protocol similar to that applied to the peptide mixture, the signal intensities from cysteine-containing peptides over total peptides can be used to calculate the enrichment efficiency. As illustrated in FIG. 4, comparable results were acquired compared to commercially available reagent, iodoTMT. These results demonstrated that the biotin enrichment moiety worked well as designed.

Figure 3:
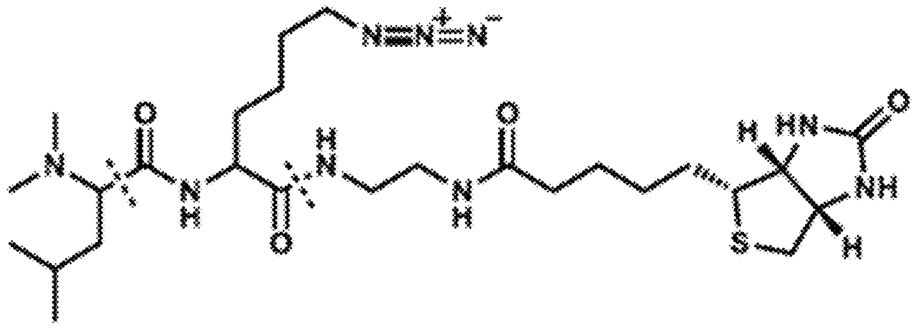
FIG. 3 shows a structure of prototype DBA tag (top) and its MS/MS spectrum (bottom).
Figure 3:
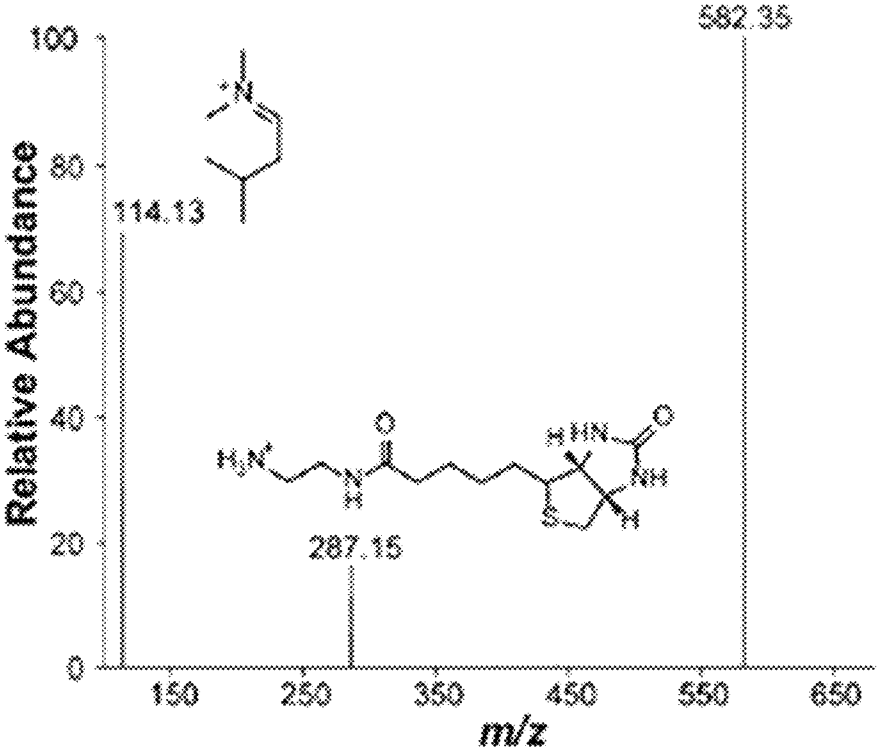

Fragmentation behavior of labeled peptides in MS/MS. Fragmentation of protoDBA tag itself generates two signature ions at m/z 114 and m/z 287, corresponding to the fragments of DiLeu and biotin backbone (FIG. 3). These two signature ions can be also observed at the MS/MS of protoDBA tag labeled peptides from BSA. By altering normalized collisional energy (NCE) to an optimal value, abundant b/y ions of peptide backbone fragmentation accompanied with decent signals of two reporter ions were acquire in a single MS/MS spectrum. The site derivatized by protoDBA can be unambiguously assigned, for both singly tagged and doubly tagged species, in particular, for two adjacent cysteine containing peptides. This result again confirmed the efficient labeling process and demonstrated robust MS/MS fragmentation behavior of protoDBA tag, which will benefit site specific identification and fragment-ion-based relative quantification.

Figure 9:
Prior Art Fig. 9
FIG. 9 shows 12-plex DiLeu reporter ion structures showing stable isotope positions in an embodiment of the invention.
Figure 9:
Prior Art Fig. 9
Figure 9:
Prior Art Fig. 9
Figure 9:
Prior Art Fig. 9
Figure 9:
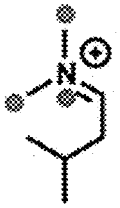
Prior Art Fig. 9
Figure 9:
Prior Art Fig. 9
Figure 9:
Prior Art Fig. 9
Figure 9:
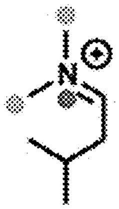
Prior Art Fig. 9
Figure 9:
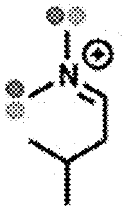
Prior Art Fig. 9
Figure 9:
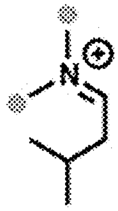
Prior Art Fig. 9
Figure 9:
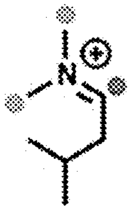
Prior Art Fig. 9
Figure 9:
Prior Art Fig. 9

Multiplexed DBA tag synthesis for high-throughput analysis of PTM. Since the modular synthesis allows DiLeu module to be installed at the last step, the intermediate product containing Biotin/Azide backbone could be prepared in a large quantity. The isotopic version of DiLeu can then be incorporated into the synthesis to make a set of multiplexed isobaric DBA tags. The unique features of DiLeu as a tandem mass tag include strong reporter ion signals and economic synthesis, as well as the introduction of isobaric moiety in a single step. This feature can minimize the cost of required isotopic reagents and make multiplexed DBA tag affordable. The first generation of DiLeu has four channels and by combining the Neucode concept, it was developed into the second generation 12-plex (FIG. 9) and the third generation 21-plex (87). Higher mass spectral resolution is needed to fully resolve reporter ions from different channels as the throughput increase. However, ultra-high resolution commonly accompanied with increased duty cycle with slower data acquisition rate and reduced target identification. Here, 12-plex DiLeu tags are chosen for multiplexed DBA synthesis and a set of 12-plex isobaric DBA tags was designed and constructed based on the structure of candidate D.

Establishment of isobaric tandem orthogonal proteolysis activity-based protein profiling (isoBOP-ABPP) workflow based on DBA tag. To identify the specific reactive amino acid sites of the target protein by using small molecules, Cravatt and co-workers developed a strategy called isotopic tandem orthogonal proteolysis-ABPP (isoTOP-ABPP) based on TEV tag (33). It was then quickly applied to many areas including identifying disease-relevant targets, mapping hyper-reactive and functional hotspots and developing inhibitors against ligandable hotspots (88-91). An isotopically light or heavy valine in TEV tag was employed for quantitative ratiometric MS-based proteomics analysis. Obviously, TEV tag relies on isotopic labeling and can only compare two samples at a time. The DBA tag proposed here employs isobaric labeling and thus can expand the quantitation channels for high-throughput analysis. This method was coined "isoBOP-ABPP" which stands for isobaric tandem orthogonal proteolysis activity-based protein profiling based on DBA tag. The general workflow of isoBOP-ABPP can be established and it is resembling isoTOP-ABPP. Briefly, proteomes are labeled in vivo or in vitro with an alkyne probe toward a particular enzyme class or amino acid modification sites. Then enzymatic digests of the proteomes are labeled with different channels of DBA tags through CuAAC click chemistry. Since the DBA tags are in excess and click chemistry is highly efficient, alkyne probe modified proteome in each sample will be thoroughly converted to isobaric DBA tagged forms. Subsequently, different samples were combined followed by biotin-streptavidin enrichment prior to running LC-MS/MS analysis. Premix ratio test starts with same amounts of proteins or peptides and identical procedure is implemented for all channels. The results of premix ratio test could be used for correction of the ratio obtained from the real sample analysis.

Candidate A was synthesized as the protoDBA tag and evaluated for several crucial performances. These multiplexed isobaric DBA tags can be used as a competing product of TEV tag and offer the ability to quantify up to 12 samples in a single experiment via high-resolution MS. However, the Candidate A has the potential challenge of coeluting with peptide analytes in enrichment as it relies on the release of biotin from streptavidin beads. This issue can be resolved with the design of Candidate B or C due to the addition of cleavable linker.

Global S-nitrosylation in Alzheimer's diseases using multiplexed DBA tag based on quantitative proteomics approach. Emerging evidence have suggested that the occurrence of aberrant S-nitrosylation of proteins could lead to protein misfolding, mitochondrial fission, synaptic damage, or apoptosis, thus contributing to the pathogenesis of Alzheimer's disease (AD) (92-94). For instance, S-nitrosylated NMDAR and caspases induced by low levels of NO can exert neuroprotective effects via suppression of neuronal cell death, whereas S-nitrosylation of Drp1 and Cdk5 lead to excessive mitochondrial fission and thus synaptic damage in AD (95, 96). Additionally, since HSP-90 and PDI are molecular chaperones and XIAP is a ubiquitin E3 ligase, S-nitrosylation of these proteins may contribute to protein misfolding and aggregation in aging neurons (97, 98). Moreover, many S-nitrosylated proteins detected in AD brains are involved in energy metabolism pathway, such as ALDOC and GAPDH (99-101). Hence, this redox reaction could lead to impaired metabolism, contributing to AD pathology. Future applications of these tags and methods also include the use of shotgun proteomics approach assisted by isoBOP-ABPP to identify and quantify global S-nitrosylation and eventually find a panel of potential candidate biomarkers in AD. It is hypothesized that additional biomarkers may exist in CSF of AD patients and can be used for diagnosis and multiplex quantification via isobaric tagging will facilitate and accelerate the search for such novel biomarkers. In addition, patients from multiple AD stages may have different signature biomarkers for monitoring disease progression.

An SNO analysis platform is able to be established based on isoBOP-ABPP using cell samples first to validate its feasibility. Further investigation of global S-nitrosylation is able to be conducted on Alzheimer's diseases mouse models and CSF samples collected from various groups (healthy control, preclinical individuals, patients with mild cognitive impairment (MCI) and AD). Bioinformatics tools can then be applied to identify differentially expressed putative biomarkers and for AD stages classification.

SNO analysis in GSNO-treated and non-treated HeLa extracts using isoBOP-ABPP. Among methods for studying protein S-nitrosylation, the biotin switch technique (BST) or its variants have gained great popularity because of the ease with which it can detect individual S-nitrosylated (SNO) proteins in biological samples (102). BST was brought up by Jaffrey et al. in 2001 and consists of three principal steps: (i) blocking of free cysteine thiols by S-methylthiolation with methylmethane thiosulfonate (MMTS; a reactive thiosulfonate); (ii) conversion of SNOs to thiols with a mild reductant ascorbate; and (iii) in situ labeling by S-biotinylation of the nascent thiols with biotin-HPDP, a reactive mixed disulfide of biotin. The degree of biotinylation (and thus S-nitrosylation) is determined by either anti-biotin immunoblotting or streptavidin pulldown followed by immunoblotting for the protein(s) of interest (61). The present DBA tags constitute another variant of BST for studying S-nitrosylation. Instead of using biotin-HPDP, IPM and DBA tag will be used for chemical labeling. IsoBOP-ABPP enabled MS proteomics will thus achieve high-throughput SNO analysis.

Figure 10:
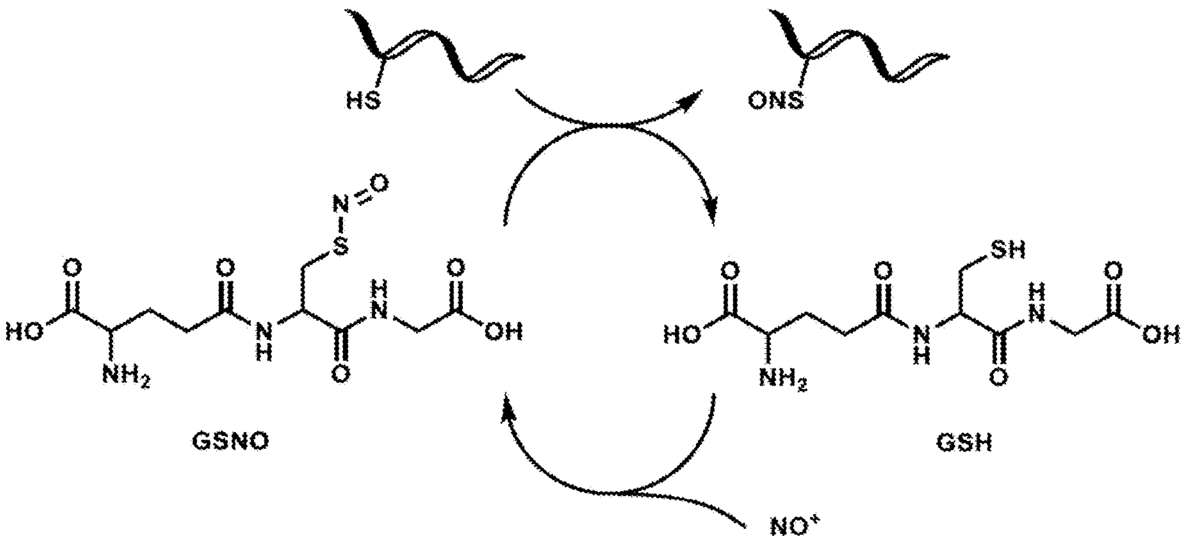
FIG. 10 illustrates GSNO-mediated transnitrosylation.

The feasibility of DBA tag-based BST are tested first using HeLa cell lines. S-Nitrosoglutathione (GSNO) is an endogenous SNO and is a source of bioavailable NO. Cell lysate treated with GSNO will undergo transnitrosylation (FIG. 10), exposing the SNO hyper-reactive cysteine residue and potential substrates of SNO in vivo. Therefore, GSNO stimulated cell lysates can provide a positive control of SNO samples (103). Two channels of DBA tags label GSNO-treated and un-treated HeLa cell lysates, respectively, and the following steps performed according to the isoBOP-ABPP framework. DBA tag-based BST allows a user to discover proteome-wide SNO targets and consensus motifs. Mapping the identified SNO proteins to the HeLa cell proteome based on normalized spectral abundance factors (NSAF) will reveal the SNO targets dynamic range relative to the whole proteome. In addition, differential groups defined by RGSNO:control ratios correspond to distinct reactivity of Cys sites to GSNO. These results can verify feasibility and validity of DBA tag-based BST enabled by isoBOP-ABPP, while providing a blueprint and reference for subsequent global SNO analysis with rodent model and human specimen.

SNO analysis in Alzheimer's diseases mouse model using isoBOP-ABPP. Two key molecules tau and amyloid-β (Aβ) have been extensively implicated in AD, forming fibrillar aggregates via oligomeric intermediates (104,105). Aβ is a small peptide that is derived from the larger amyloid precursor protein (APP). Aggregates of Aβ form histological lesions known as amyloid plaques, which, when surrounded by neurites filled with fibrillary tau, give rise to what are referred to as neuritic plaques (106, 107). Various transgenic mouse models, based on the overexpression of mutant forms of human APP and recapitulating the AD phenotype are currently used to investigate mechanisms underlying disease pathology (108). Here, the APP/PS-1 transgenic mouse model, is selected for demonstration of the isoBOP-ABPP method as several SNO-modified proteins have previously been reported in the brain and synaptosomes from AD subjects (109, 110).

APP/PS-1 (hereafter referred to as AD) and wild type (WT) mice (N=3 for each genotype) will be euthanized using $CO_2$ before brain tissues is harvested and homogenized in an ice-cold phosphate buffer saline (PBS) solution containing 8 M urea. For SNO analysis, 1 mg brain proteins from individual WT or AD mice are treated with IAA to block free sulfhydryl groups. After tryptic digestion, ascorbate is added to the peptide mixture to selectively reduce SNO. Reduced peptides containing nascent sulfhydryl groups are labeled by IPM. Six channels of DBA tags are used to conjugate IPM-modified peptides in WT and AD samples, respectively. The six samples are combined to a single mixture and subject to streptavidin resin for enrichment. Enriched and tagged peptide samples are eluted from the resin and fractionated by SCX and analyzed using nanoLC-MS/MS. Protein level ratios, SNO site occupancy in WT or AD, and SNO ratios between WT and AD can be calculated by using corresponding reporter ion intensities. The results can be examined by comparison with previous literatures and instruct ensuing application on human samples.

Global SNO analysis in CSF samples from human patients using isoBOP-ABPP. At present, a definitive diagnosis of AD can only be obtained at autopsy via the histological quantification of two AD hallmarks: brain amyloid plaques and intraneuronal neurofibrillary tangles (111). Thus, there is an urgent need for the discovery of new biomarkers that will aid in identifying the disease at its most early clinical stages as well as preclinically. Cerebrospinal fluid (CSF), given its contiguity with the brain interstitial space, represents the most direct means to study the biochemical changes occurring in the central nervous system (CNS). People have found certain protein changes directly associated with the progression of AD, for instance, levels of CSF amyloid-β42 (Aβ42) are reduced in AD, even in early and preclinical stages of the disease, and levels of CSF total tau and phosphorylated tau (p-tau) increase in AD and accelerate during later disease stages, concomitant with neurofibrillary tangle formation and synapse and neuron loss (112, 113). However, there are limited research focusing on PTM analysis in various AD stages using CSF samples including S-nitrosylation. To investigate the global SNO changes along with the progression of the disease, and to confidently identify potential candidate biomarkers, high-throughput quantitative tools are essential. Therefore, it was proposed to use isoBOP-ABPP enabled by 12-plex DBA tags to perform quantitative proteomics in CSF samples from different stages of AD.

Figure 11:
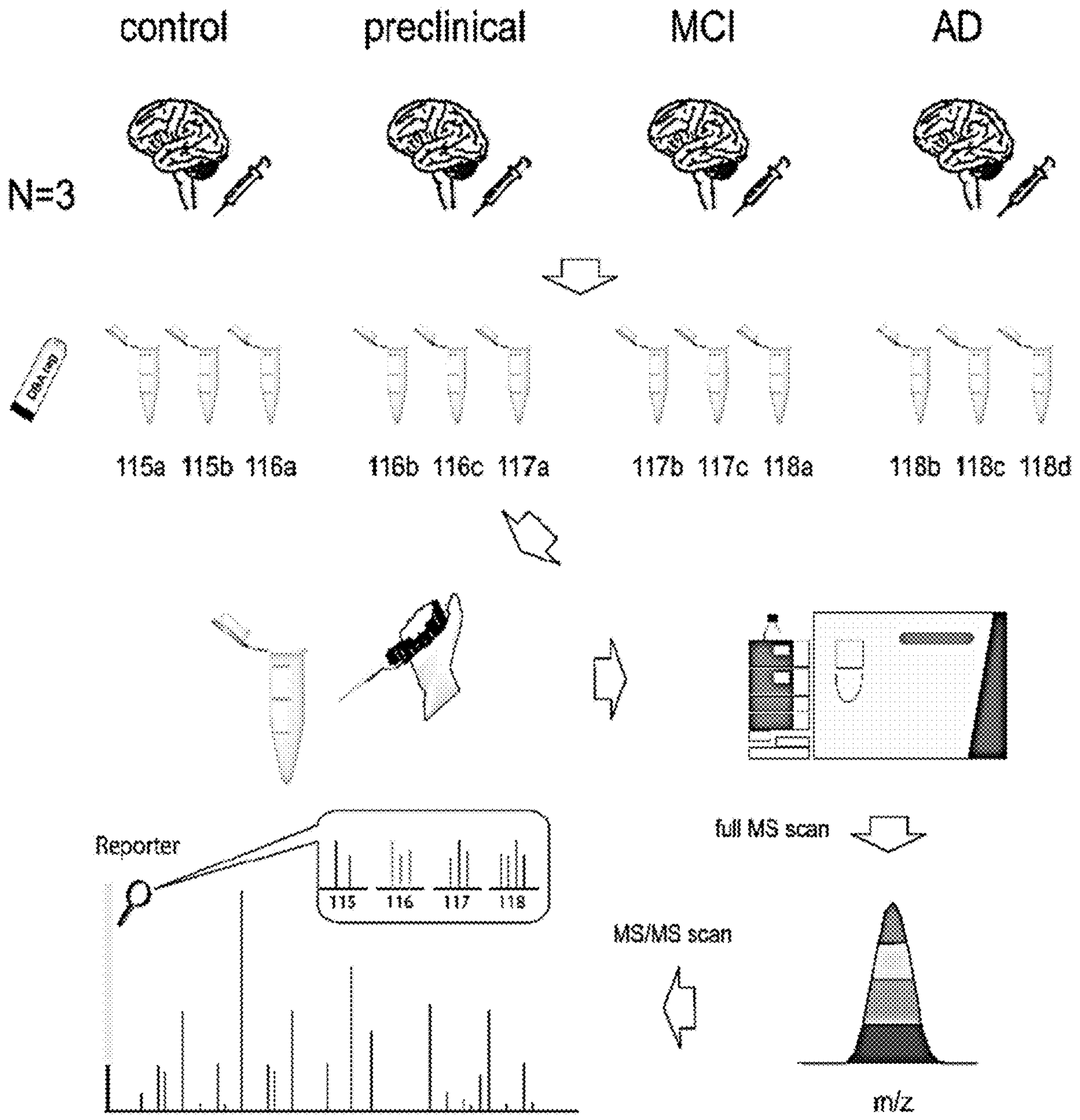
FIG. 11 shows a workflow of 12-plex DBA tag enabled isoBOP-ABPP quantitative proteomics for SNO analysis of CSF samples collected from patients at different stages of AD.

As shown in FIG. 11, four groups (control, preclinical, MCI and AD) of CSF samples are collected corresponding to different stages of disease progression. Each of which has three biological replicates making up twelve samples in total. Identical proteolysis and BST procedure is applied for all samples, and 12-plex DBA reagents are used for chemical labeling of 12 samples respectively, after which they are combined together to a single mixture and performed downstream SNO enrichment and LC-MS/MS analysis. Accurate quantification can be achieved by comparing relative intensities of the zoom-in low mass region for 12 reporter ions, and differentially regulated SNO proteins or sites will be identified for further investigation.

The development of 12-plex DBA reagents will provide unprecedented throughput and capacity for multiplexed PTM quantitative proteomics measurements that will facilitate AD biomarker discovery and deepen understanding of SNO in AD. Smooth development of DBA-based BST method and its application to AD animal model is expected. Moreover, certain identified SNO proteins or sites that are differentially regulated in different CSF sample groups can be regarded as potential biomarkers. Novel biomarkers are validated by the SRM targeted proteomics approach.

Expansion of the scope of application of DBA tag and establishment of a pan-PTM high-throughput quantitative proteomics platform for various PTM study and crosstalk investigation. With the advent of isoTOP-ABPP technique, many novel discoveries were made in PTM research (114-116). The broad utility of isoTOP-ABPP stems from the exquisite design of chemical labeling strategy. It separates the target-site-oriented warhead from functionalities possessing more general purposes such as enrichment and isotope incorporation, thus avoiding redesigning specific chemical probes case-by-case. Click chemistry bridges alkyne and azide in an efficient and robust manner both in vitro and in vivo, making classical TEV tag widely used in various applications (88, 117-119). Similarly, the DBA tag and isoBOP-ABPP pipeline are expected to inherit merits of TEV tag as well as isoTOP-ABPP platform, with distinctive feature of larger sample processing volume. Moreover, more available channels of tags enable quantifying multiple PTMs simultaneously, allowing investigation of PTM crosstalk and interactions.

Cysteine oxidative modification analysis is possible in addition to S-nitrosylation first using DBA tag and isoBOP-ABPP platform. Furthermore, broader application with other PTMs including carbonylation and citrullination are available via chemical proteomics. To this end, bio-orthogonally probing and fishing multiple PTMs in a one-pot manner and quantitatively profiling their interactions and combinatorial effects is envisioned.

Figure 12:
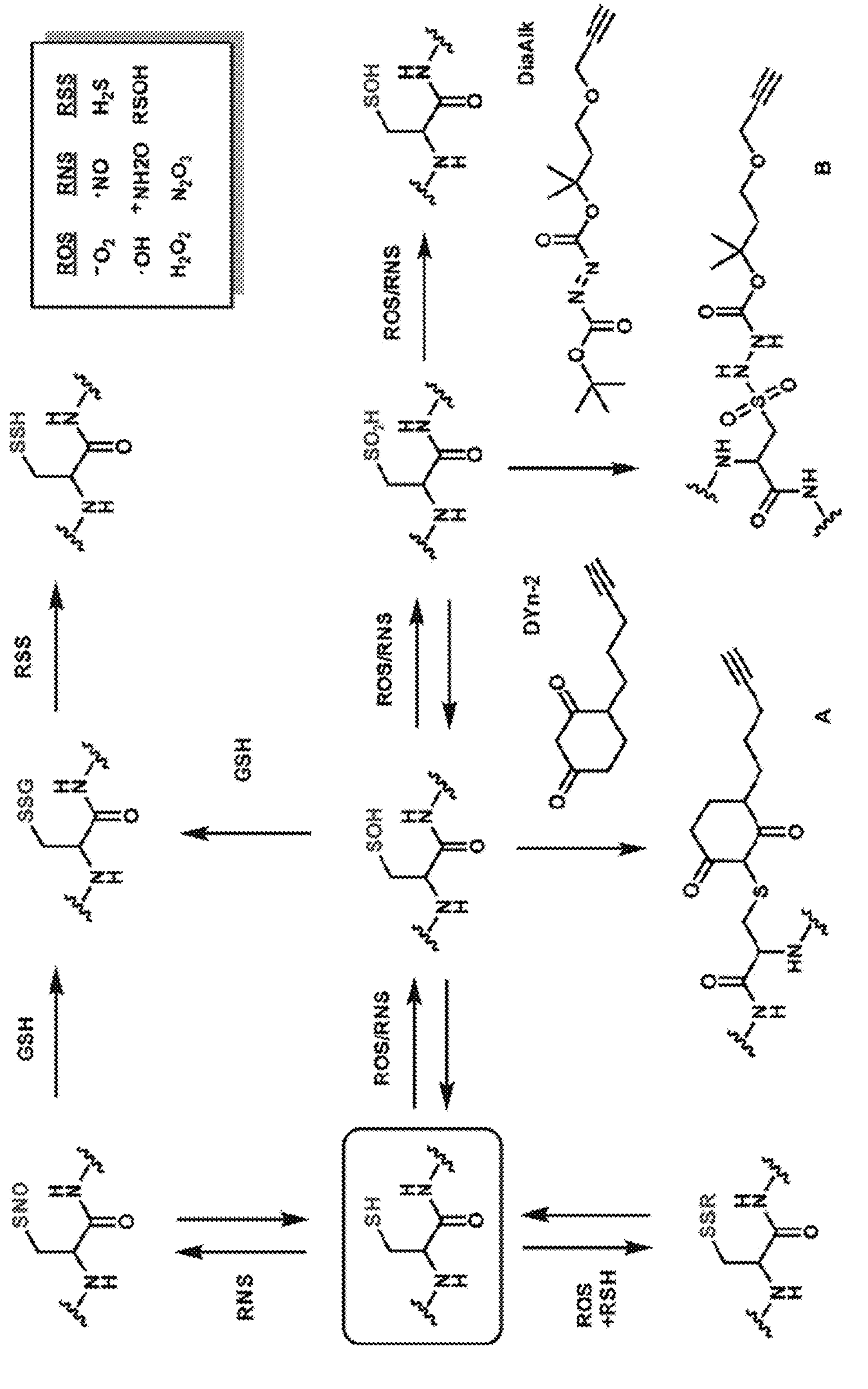
FIG. 12 shows biologically relevant oxidative PTMs of cysteine and chemical probes for —SOH and —$SO_2$H.
Figure 13:
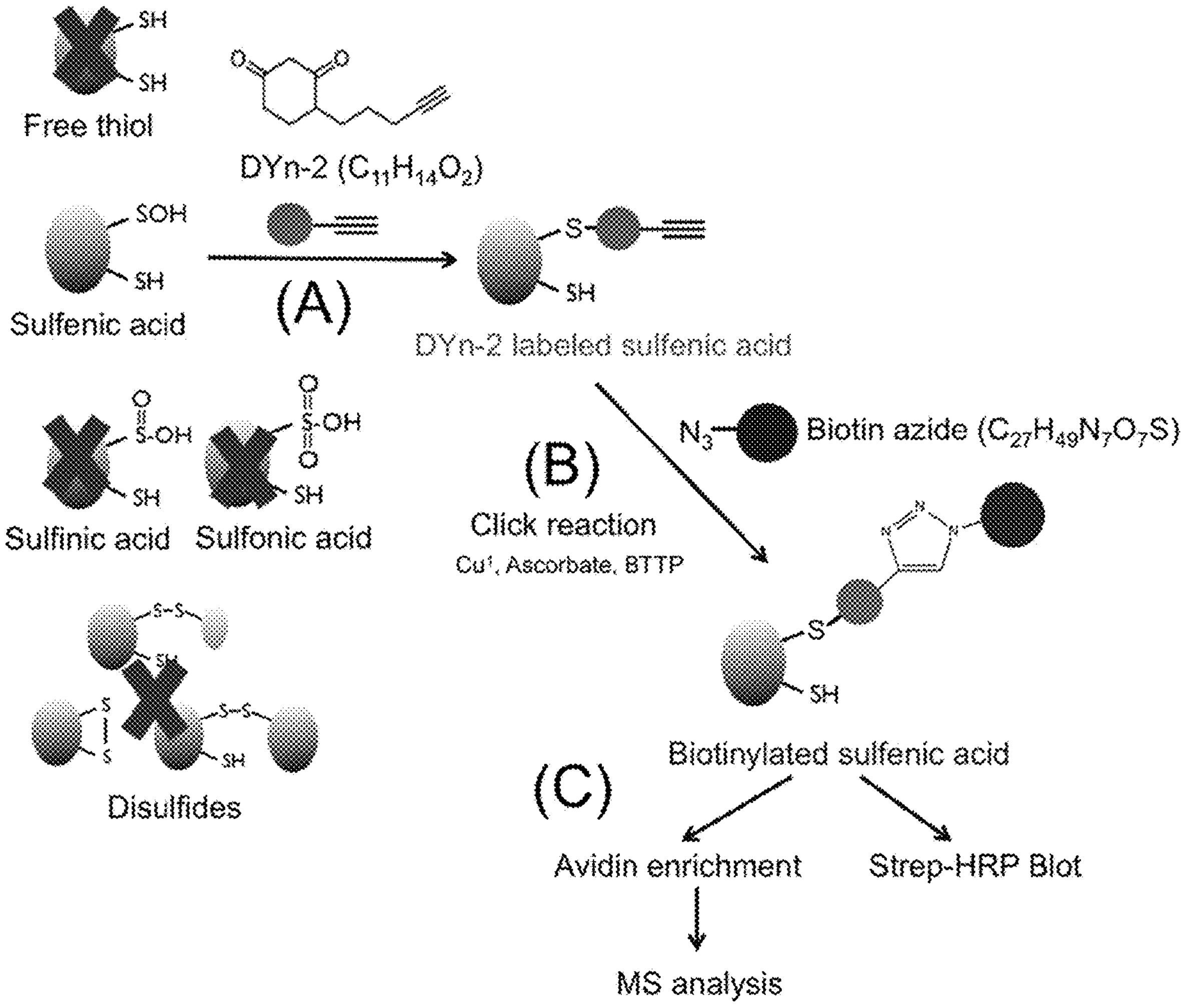
FIG. 13 shows chemical labeling for converting oxidative (SOH) thiol into a terminal alkyne utilizing the chemical reagents DYn-2 (step A), reacting the terminal alkyne with a biotin azide tagging reagent (step B), followed by avidin enrichment and MS analysis (step C).

Application of DBA tag to the analysis of oxidative post-translational modification (OxiPTM). The prerequisite of using DBA tag and isoBOP-ABPP platform for PTM analysis is the prior selective tagging of modification sites with an alkyne handle. Since DBA tag only contains azide group for conjugation enabled by click chemistry, the selectivity of PTM probing is achieved by precursor alkyne modified molecules. In addition to S-nitrosylation, the thiol group of the cysteine side chain is subject to a variety of oxiPTMs (FIG. 12). Each oxidation state of cysteine exhibits different reactivity which, in turn, may determine their functions. These differences in reactivity may be subtle, presenting an interesting challenge in developing chemoselective probes to detect these modifications (120-122). Currently, chemical labeling approaches have been reported for S-sulfenylation (—SOH) and S-sulfinylation (—$SO_2H$) utilizing special chemical reagents DYn-2 and DiaAlk with high chemoselectivity (123, 124). These probes can successfully convert oxidative thiol into a terminal alkyne, which provides an anchor for DBA tag and makes application of isoBOP-ABPP feasible (FIG. 13).

Figure 14:
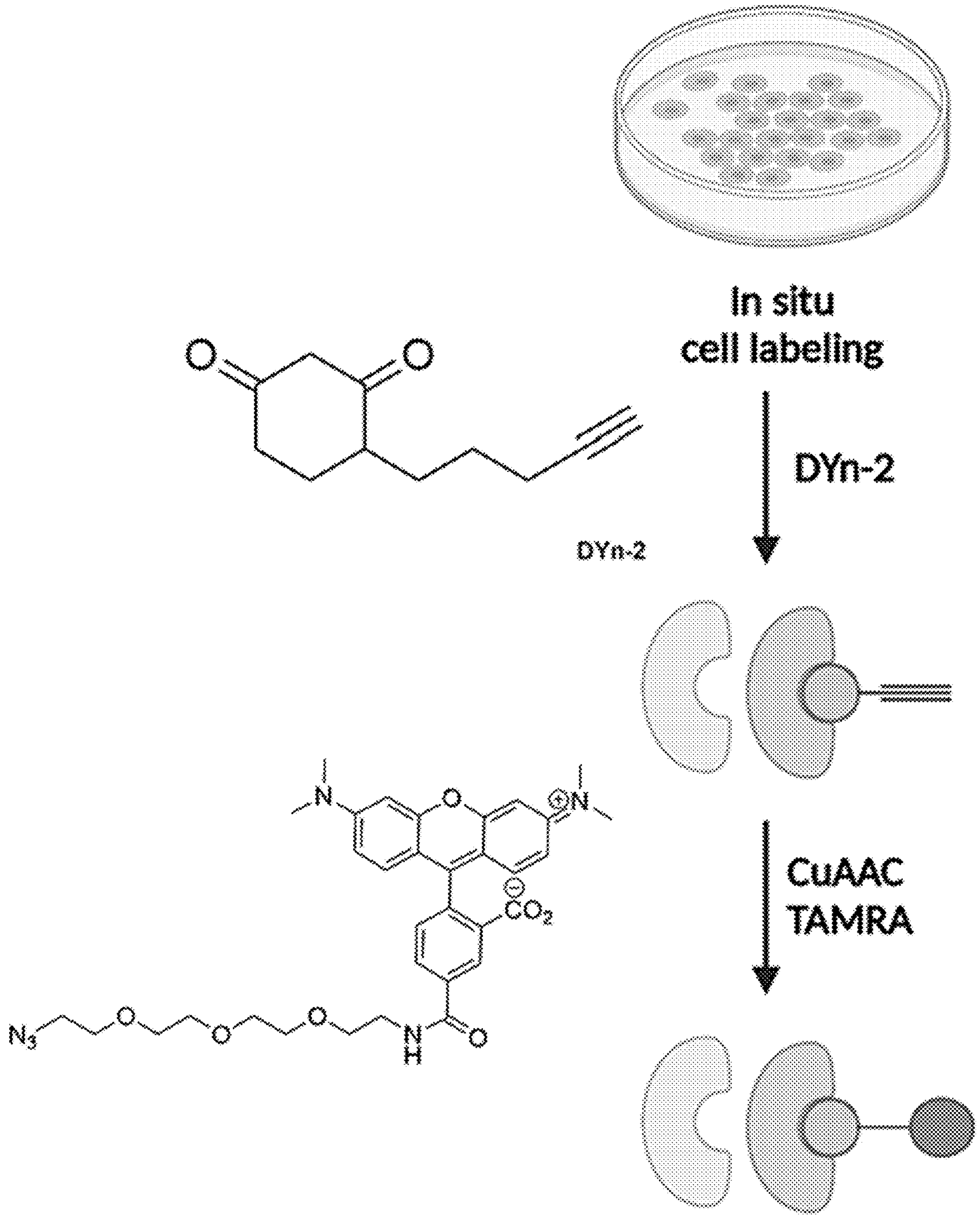
FIG. 14 shows a general strategy for labeling and enrichment of sulfenic acid-modified proteins. Cell lines were treated with Dyn-2 in vivo then labeled proteins were coupled via click chemistry. Sulfenic acid-modified proteins were generated using in-gel.
Figure 15:
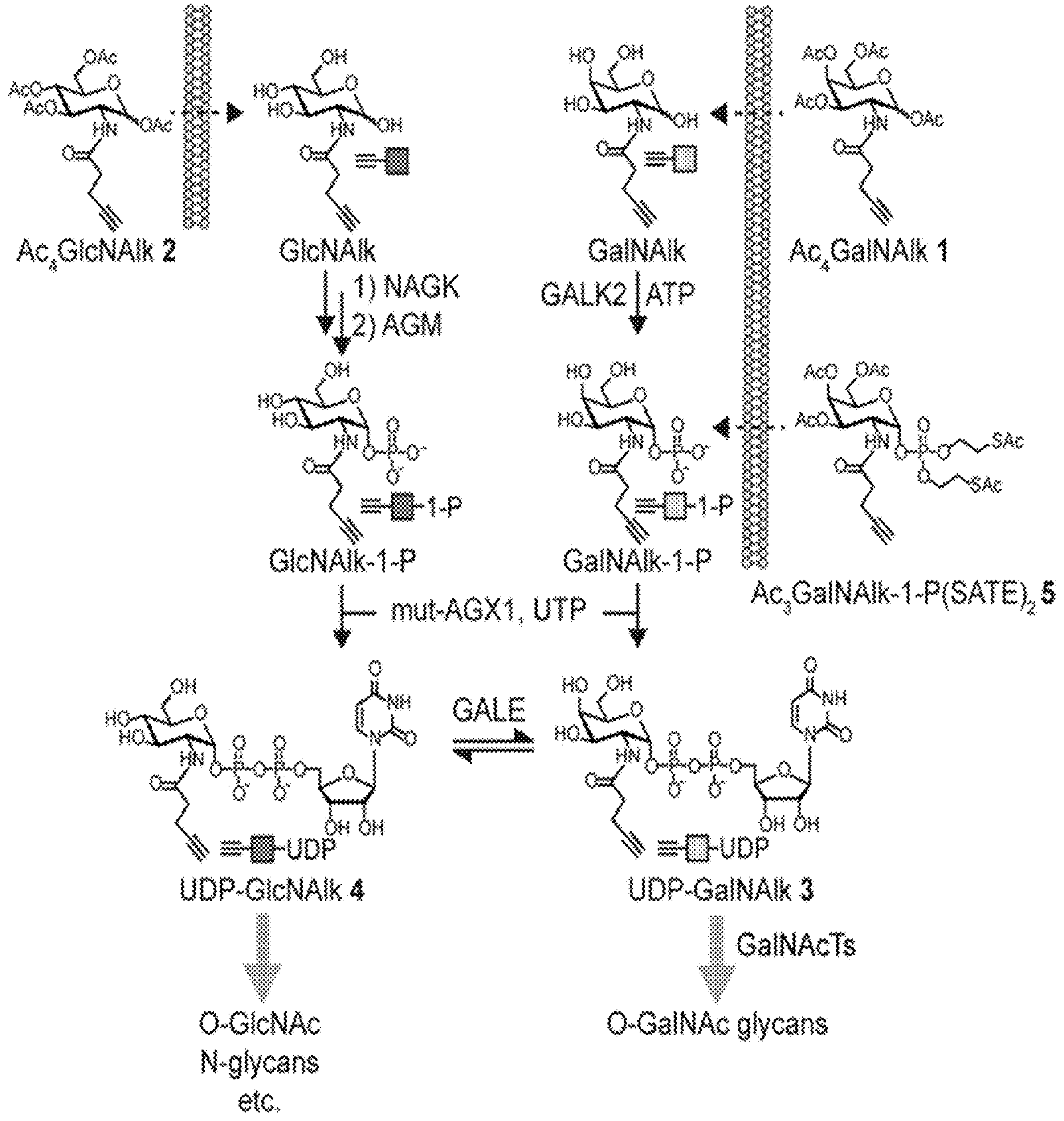
FIG. 15 shows a general strategy for labeling and enrichment of sulfenic acid-modified proteins. Cell lines were treated with Dyn-2 in vivo then labeled proteins were coupled via click chemistry.
Figure 16:
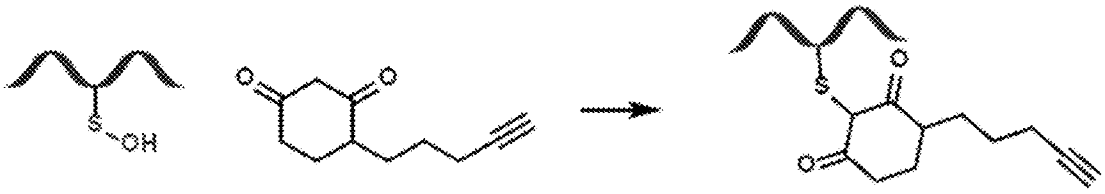
FIG. 16 illustrates reacting modification sites of different post-translationally modified peptides in order to add a probe containing a terminal alkyne.
Figure 16:
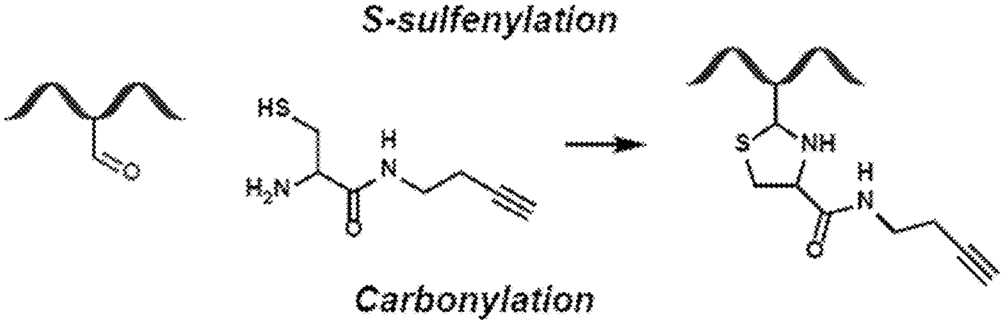
Figure 16:
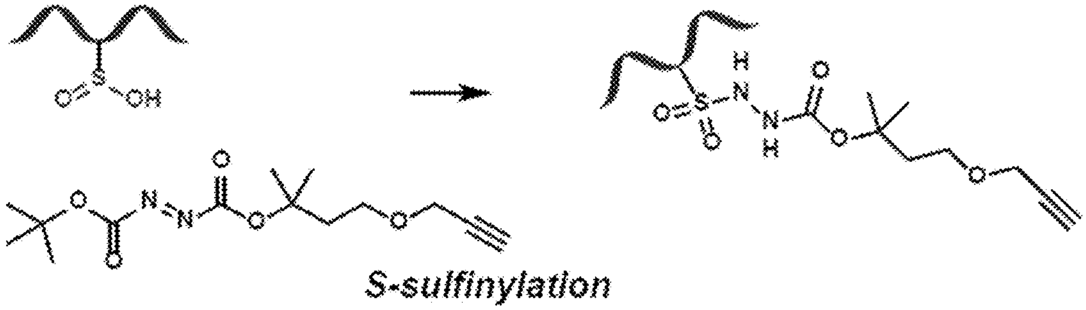
Figure 16:
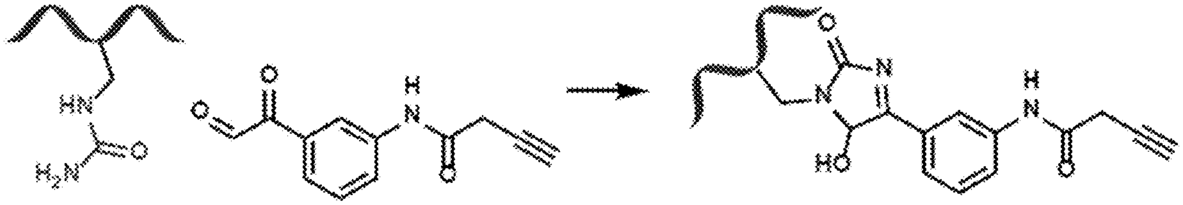

FIG. 14 shows a strategy for labeling and enrichment of sulfenic acid-modified proteins. Cell lines were treated with Dyn-2 in vivo then labeled proteins were enriched by reacting the resulting terminal alkyne with an azide group. FIG. 15 shows a similar strategy for labeling and enrichment of O-GlcNAcylated proteins. FIG. 16 illustrates approaches for reacting modification sites of exemplary PTMs (S-sulfenylation, carbonylation, S-sulfinylation, and citrullination) in order to add a probe containing a terminal alkyne, which can then be used to react with tagging reagents, particularly those containing azide groups, of the present invention.

Peptide ANP is treated with $H_2O_2$ and $FeSO_4$ to prepare sulphenated and sulphinated standard peptides for method development (125). DYn-2 and DiaAlk are then be used to probe SOH and $SO_2H$, respectively. Labeling performance and chemoselectivity is be monitored by MALDI-TOF MS. After optimization of labeling condition, integrating scheme of modified BST and isoBOP-ABPP method, brain tissues from AD mouse model or CSF from different stages of AD patients can be used as complex biological samples, for exploration of broader application of DBA reagents and deepen understanding of OxiPTM in organisms.

Figure 17:
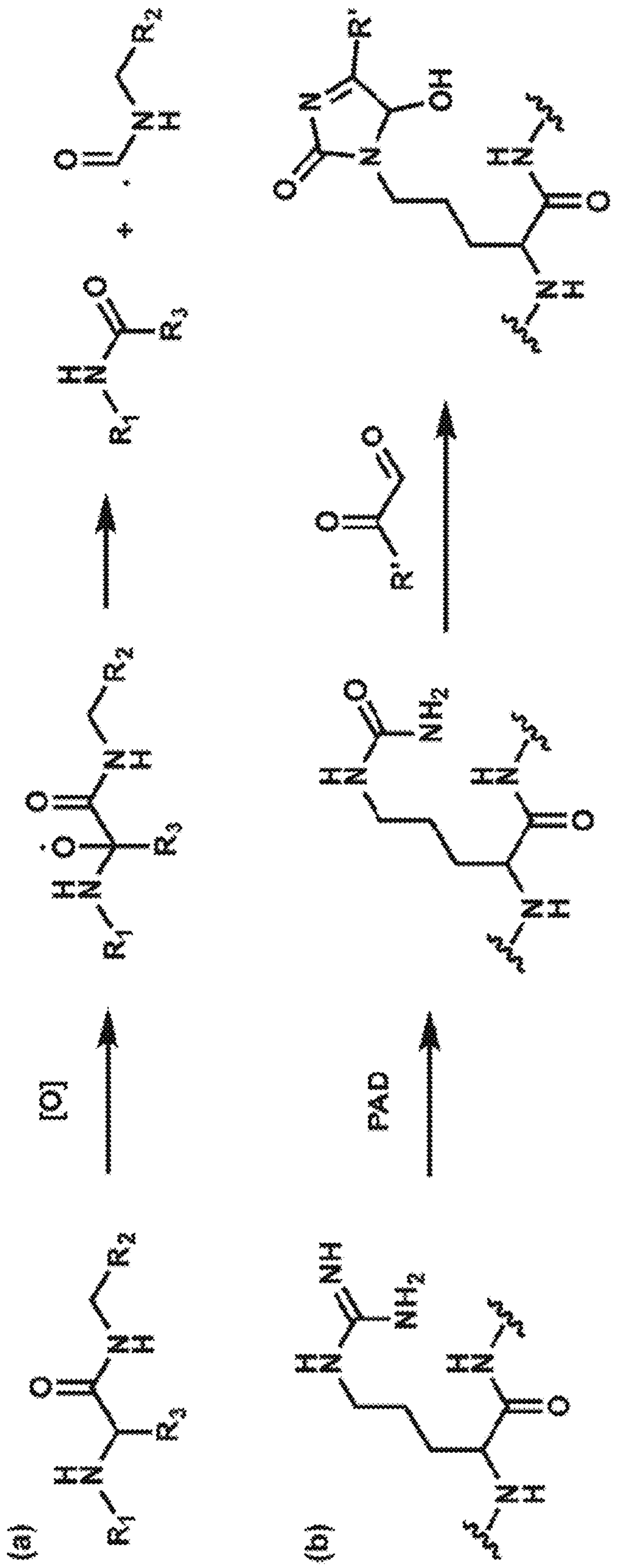
FIG. 17 shows (panel a) Oxygen radical induced peptide backbone bond cleavage results in peptide carbonylation; (panel b) Arginine citrullination and phenylglyoxal chemical derivatization.

Application of DBA tag to the analysis of carbonylation and citrullination PTM. Carbonylation and citrullination are two other PTMs that can be investigated using DBA tag enabled isoBOP-ABPP approach. In addition to OxiPTM on cysteine residue, ROS can also induce peptide cleavage which results in producing electrophilic carbonyl groups, also known as protein carbonylation (126) (FIG. 17, panel a). Recently, quantitative chemoproteomic approaches to globally and site-specifically profile electrophilic carbonyl products formed from peptide backbone cleavages in human proteomes were reported (127, 128). In these studies, researchers employed a nucleophilic probe, alkynyl hydrazine (HZyne), to selectively label and stabilize carbonylated proteins in cell lysates. Then modified version of isoTOP-ABPP platforms were applied for quantitative analysis. Therefore, similar studies can be conducted using DBA tag to label HZyne converted carbonylated proteins/peptides and to perform quantitative comparison based on isoBOP-ABPP.

Citrullination is an arginine modification that is catalyzed by a group of hydrolases called protein arginine deiminases (PADs), in which the positively charged guanidinium is hydrolyzed to the neutral urea (FIG. 17, panel b), which alters the charge and hydrogen bonding potential of this residue and impact important biological processes. Thompson et al. previously developed citrulline-specific probe based on the chemoselective reaction that occurs between glyoxals and either citrulline or arginine under acidic or basic conditions, respectively (129). The initial tag is a rhodamine-derivative and used for visualization of the citrullination in both purified proteins and proteins present in complex mixtures such as serum. Later, biotin-derivative was developed to support chemical proteomics analysis (130, 131). Enlightened by their work, it is envisioned to design and synthesize an alkyne containing molecules which also possess phenylglyoxal moiety. This reagent is expected to introduce a terminal alkyne onto citrullinated sites through selective reaction, which offers opportunity for downstream incorporation of DBA tag and isoBOP-ABPP enabled quantitative proteomics.

Multiplexed DBA tag enabled PTM crosstalk investigation. Typically, PTMs are studied in isolation to determine possible regulation imparted by an individual PTM (132). However, PTM profiling studies have shown that numerous proteins can be modified by multiple PTMs, a finding that suggests the possibility of regulatory crosstalk between unique modification events. For example, the phosphorylation of specific cell-cycle regulators to create phosphodegrons that are recognized by ubiquitin ligases to direct ubiquitylation and subsequent degradation is a well-characterized example of PTM cross-talk (133). Despite classic examples, the breadth of PTM crosstalk, and whether crosstalk is a widely used mechanism of regulation, remains to be determined. Previously, serial PTM enrichment approaches were reported to catalog multiple modification events in a single sample using MS-based approaches (6, 134). More recently, simultaneous affinity enrichment of two PTMs for quantification and site localization provided a quick and cost-effective alternative (135). In light of the effectiveness of biorthogonal reaction and compatibility of isoBOP-ABPP platform, it is envisioned to use DBA tag enabled isoBOP-ABPP to simultaneously enrich multiple PTMs and facilitate deciphering PTM crosstalk.

Nitric oxide (NO) is generated, in most cell types, from arginine and $O_2$ by NO synthases (NOSs) and could possibly modify cysteine residue to afford S-nitrosylation. In the meantime, the other product in this pathway is the citrulline originated from arginine (136). Despite close connection, the correlation and interaction between S-nitrosylation and citrullination has rarely been studied. Specific chemical probes are used to target SNO and citrullination sites in hand, both of which contain the alkyne group. When treating proteome with both probes, respective labeling of SNO and citrullination is envisioned. Sequential click chemistry will introduce DBA tag onto the derivatized PTMs sites which makes it feasible to simultaneously enrich both SNO and citrullination via the isoBOP-ABPP platform. CSF samples from AD patients are used to perform the proof-of-principle experiments, as both S-nitrosylation and citrullination have been reported to play important roles in neurodegenerative diseases but few studies investigate their relationship and connection. Once the co-enrichment of SNO and citrullination proves to be success, this design and framework can be widely used for investigation of multiple PTMs at a time and enhance understanding of the interaction and crosstalk between different PTMs in various biological systems.

A pan-PTM high-throughput quantitative proteomics platform can be established based on the DBA tag. Application scope can also be extended to, but not limited to, S-sulphenation, S-sulphination, carbonylation and citrullination. One potential concern with the investigation of crosstalk between S-nitrosylation and citrullination is the difficulty of bioinformatic analysis. The lack of specific search engine can limit bioinformatic analysis to existing software such as MaxQuant and PEAKS. The default configuration of these search engine may not be appropriate or perform the best analysis in terms of PTM crosstalk. Therefore, custom-designed bioinformatic tool for specifically analyzing multiple DBA tag labeled peptides may be developed to generate useful biological insights.

Conclusions. The compound of this example uniquely integrates advances of biorthogonal reaction empowered chemical proteomics and DiLeu tag-based multiplex quantitative proteomics to enable a novel chemical tool, the cDBA tag. This invention allows for the building of a new analytical platform, isoBOP-ABPP, further allowing for high-throughput quantitative analysis of PTMs and facilitating more comprehensive discovery and validation of SNO biomarkers in AD CSF. In addition, the versatility of the isoBOP-ABPP platform also supports Pan-PTM and PTM crosstalk studies. These new tools will enable a deeper understanding of PTMs and the advances in technology and new insights will have broad impact on discovery of biomarkers in various diseases.

Example 3—Synthesis of Above Candidate Molecules

Synthesis of Candidate A. 5-(2-oxohexahydro-1H-thieno[3,4-d]imidazol-4-yl)pentanoic acid (1 eq), DIPEA, (1.2 eq), and HATU (1.2) were added dry DMF and stirred for 30 min before adding tert-butyl (2-aminoethyl)carbamate (1.2 eq). The resulting reaction was stirred at room temperature for 24 hr before quenching with water and extracting with ethyl acetate. The extras were combined and concentrated before performing column purification to afford the compound tert-butyl (2-(5-(2-oxohexahydro-1H-thieno[3,4-d]imidazol-4-yl)pentanamido)ethyl)carbamate (a1).

Compound a1 was dissolved in 4 N HCl dioxane and stirred for 2 hr and the mixture was vaporized on the rotary evaporator. The crude product was used for the next step without further purification.

N2-(((9H-fluoren-9-yl)methoxy)carbonyl)-N6-diazolysine (1 eq), DIPEA, (1.2 eq), and HATU (1.2) were added dry DMF and stirred for 30 min before adding crude N-(2-aminoethyl)-5-(2-oxohexahydro-1H-thieno[3,4-d]imidazol-4-yl)pentanamide (1.5 eq). The resulting reaction was stirred at room temperature for 24 hr before quenching with water and extracting with ethyl acetate. The extras were combined and concentrated before performing column purification to afford the compound (9H-fluoren-9-yl)methyl (6-azido-1-oxo-1-((2-(5-(2-oxohexahydro-1H-thieno[3,4-d]imidazol-4-yl)pentanamido)ethyl)amino)hexan-2-yl)carbamate (a2).

Compound a2 was dissolved in piperidine DMF and stirred for 2 hr to deprotect the Fmoc group and the mixture was vaporized on the rotary evaporator. The crude product was used for the next step without further purification.

L-leucine (1 eq) and $NaBH_3CN$ (2.2 eq) were dissolved in methanol with ice bath, then formaldehyde (2.2 eq) were added into the reaction dropwise. The reaction was stirred for 4 hr and concentrated on the rotary evaporator before running column purification to afford white solid N,N-dimethyl leucine.

N,N-dimethyl leucine (1 eq), DIPEA, (1.2 eq), and HATU (1.2) were added dry DMF and stirred for 30 min before adding crude 2-amino-6-azido-N-(2-(5-(2-oxohexahydro-1H-thieno[3,4-d]imidazol-4-yl)pentanamido)ethyl)hexanamide (1.5 eq). The resulting reaction was stirred at room temperature for 24 hr before quenching with water and extracting with ethyl acetate. The extras were combined and concentrated before performing column purification to afford the final compound 6-azido-2-(2-(dimethylamino)-4-methylpentanamido)-N-(2-(5-(2-oxohexahydro-1H-thieno[3,4-d]imidazol-4-yl)pentanamido)ethyl)hexanamide (Candidate A). This synthesis is illustrated in Scheme A below.

Scheme A

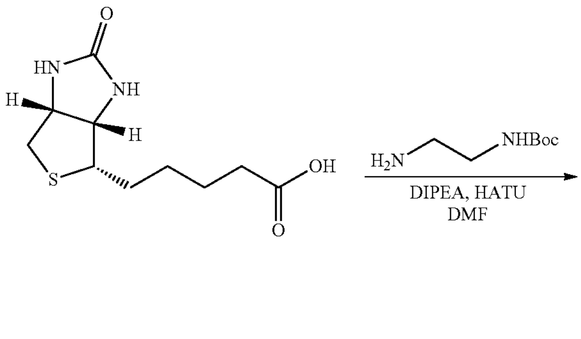

-continued

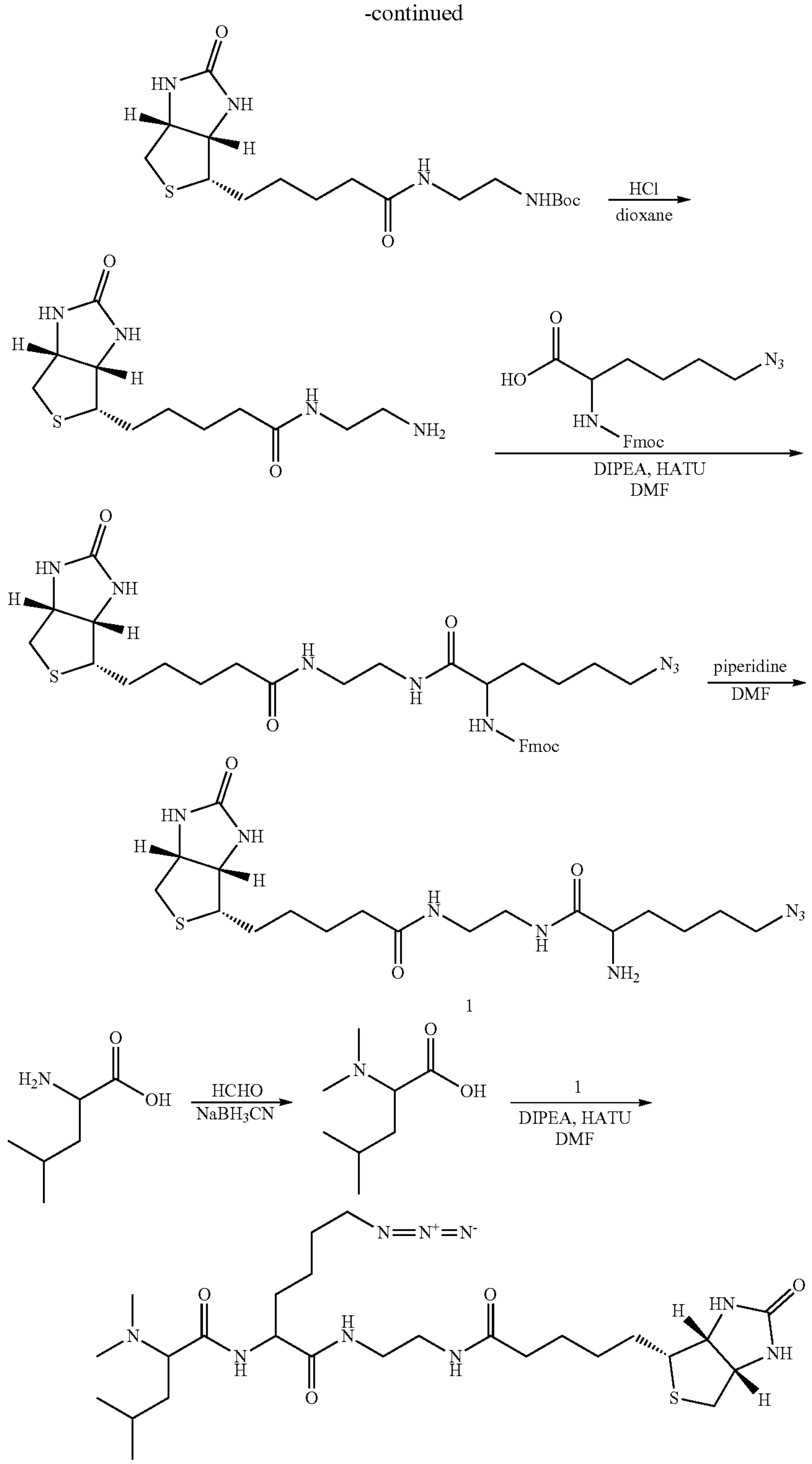

Synthesis of Candidate B. 5-(2-oxohexahydro-1H-thieno[3,4-d]imidazol-4-yl)pentanoic acid (1 eq), DIPEA, (1.2 eq), and HATU (1.2) were added dry DMF and stirred for 30 min before adding 4-amino-2-methylbutan-2-ol (1.2 eq). The resulting reaction was stirred at room temperature for 24 hr before quenching with water and extracting with ethyl acetate. The extras were combined and concentrated before performing column purification to afford the compound N-(3-hydroxy-3-methylbutyl)-5-(2-oxohexahydro-1H-thieno[3,4-d]imidazol-4-yl)pentanamide (b1).

Compound b1 was dissolved in DCM and stirred for 2 hr and 1-chloroethyl carbonochloridate was added dropwise. The mixture was stood for 1 hr and then vaporized on the rotary evaporator. The crude product was purified by column chromatography to get the product 1-chloroethyl (2-methyl-4-(5-(2-oxohexahydro-1H-thieno[3,4-d]imidazol-4-yl)pentanamido)butan-2-yl) carbonate (b2).

Compound b2 (1 eq), 2-amino-4-azidobutanoic acid (1.2 eq), were added dry DCM and stirred for 2 hr. The crude product 4-azido-2-((((2-methyl-4-(5-(2-oxohexahydro-1H-thieno[3,4-d]imidazol-4-yl)pentanamido)butan-2-yl)oxy)carbonyl)amino)butanoic acid (b3) were used without further purification.

L-leucine (1 eq) and $NaBH_3CN$ (2.2 eq) were dissolved in methanol with ice bath, then formaldehyde (2.2 eq) were added into the reaction dropwise. The reaction was stirred for 4 hr and concentrated on the rotary evaporator before running column purification to afford white solid N,N-dimethyl leucine. Then, N,N-dimethyl leucine (1 eq), DIPEA, (1.2 eq), and HATU (1.2) were added dry DMF and stirred for 30 min before adding tert-butyl (2-aminoethyl) carbamate (1.2 eq). The resulting reaction was stirred at room temperature for 24 hr before quenching with water and extracting with ethyl acetate. The extras were combined and concentrated before performing column purification to afford the compound DiLeuEN.

Crude compound b3 (1 eq), DIPEA, (1.2 eq), and HATU (1.2) were added dry DMF and stirred for 30 min before adding DiLeuEN (1.5 eq). The resulting reaction was stirred at room temperature for 24 hr before quenching with saturated $NaHCO_3$ and extracting with ethyl acetate. The extras were combined and concentrated before performing column purification to afford the final compound 2-methyl-4-(5-(2-oxohexahydro-1H-thieno[3,4-d]imidazol-4-yl)pentanamido)butan-2-yl (4-azido-1-((2-(2-(dimethylamino)-4-methylpentanamido)ethyl)amino)-1-oxobutan-2-yl) carbamate (Candidate B). This synthesis is illustrated in Scheme B below.

Scheme B

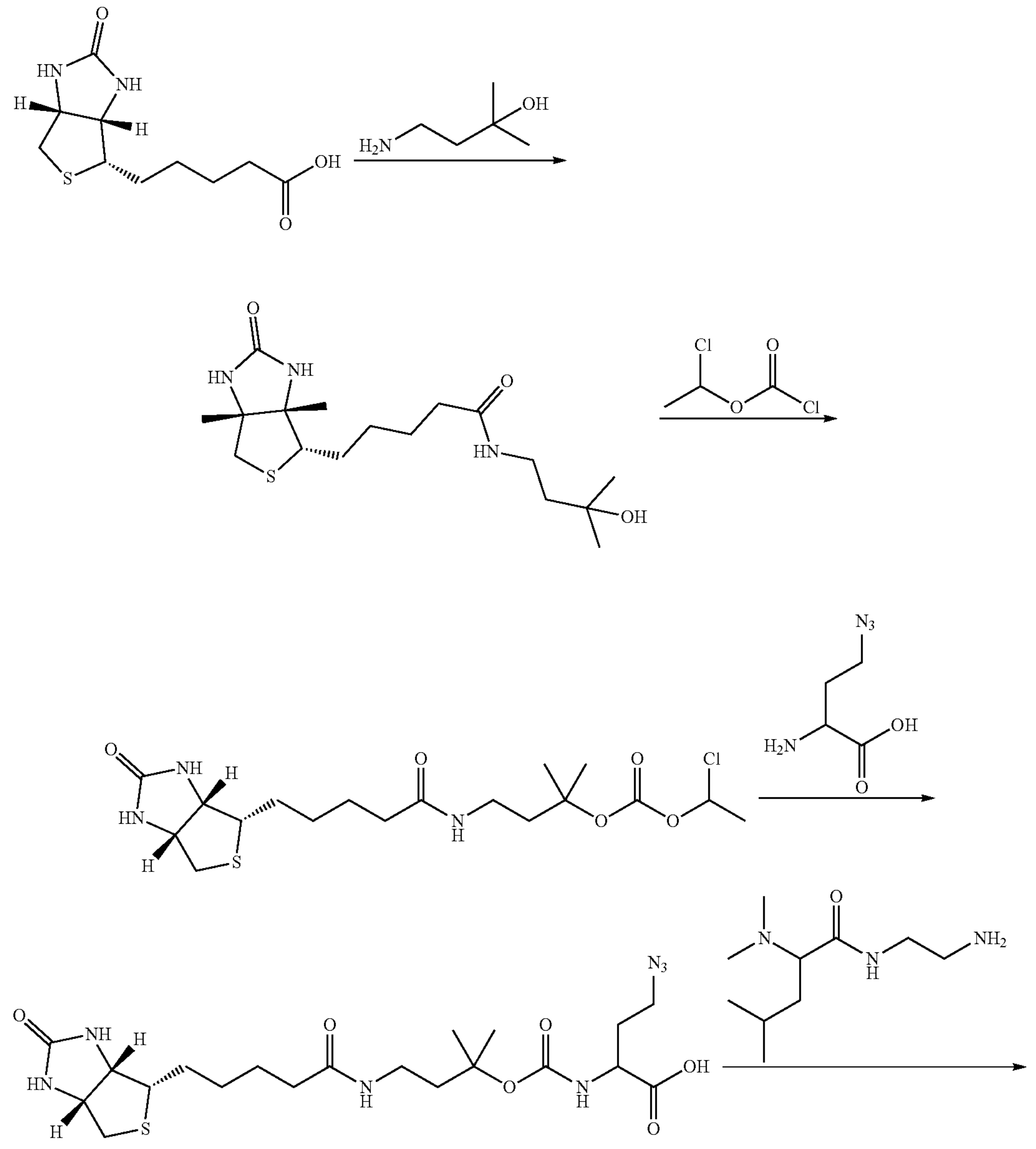

-continued

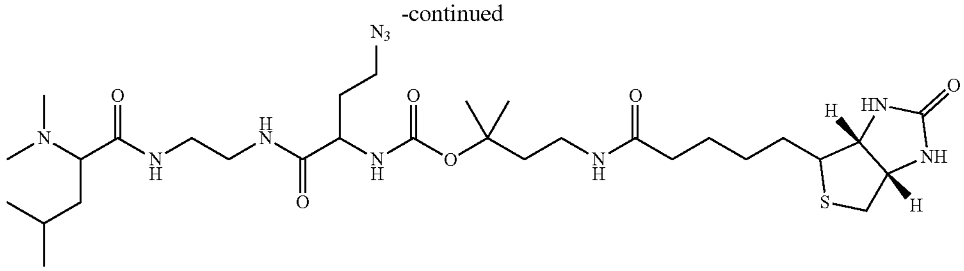

Candidate B

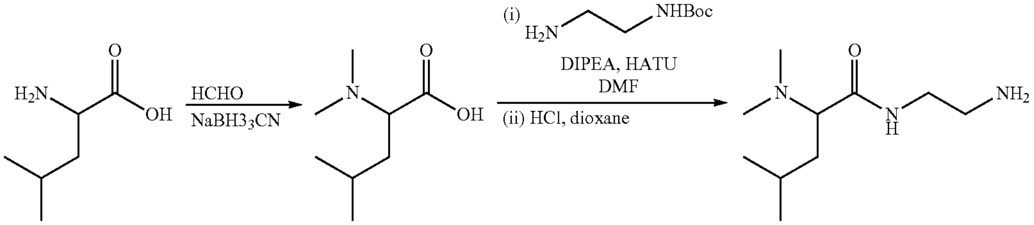

Synthesis of Candidate C. 5-(2-oxohexahydro-1H-thieno[3,4-d]imidazol-4-yl)pentanoic acid (1 eq), DIPEA, (1.2 eq), and HATU (1.2) were added dry DMF and stirred for 30 min before adding 1,4-diaminobutane-2,3-diol (0.9 eq). The resulting reaction was stirred at room temperature for 24 hr before quenching with saturated $NaHCO_3$ and extracting with ethyl acetate. The extras were combined and concentrated before performing column purification to afford the compound N-(4-amino-2,3-dihydroxybutyl)-5-(2-oxohexahydro-1H-thieno[3,4-d]imidazol-4-yl)pentanamide (c1).

N2-(((9H-fluoren-9-yl)methoxy)carbonyl)-N6-diazolysine (1 eq), DIPEA, (1.2 eq), and HATU (1.2) were added dry DMF and stirred for 30 min before adding compound c1 (1.5 eq). The resulting reaction was stirred at room temperature for 24 hr before quenching with water and extracting with ethyl acetate. The extras were combined and concentrated before performing column purification to afford the compound (9H-fluoren-9-yl)methyl (6-azido-1-((2,3-dihydroxy-4-(5-2-oxohexahydro-1H-thieno[3,4-d]imidazol-4-yl)pentanamido)butyl)amino)-1-oxohexan-2-yl) carbamate (c2).

Compound c2 was dissolved in piperidine DMF and stirred for 2 hr to deprotect the Fmoc group and the mixture was vaporized on the rotary evaporator. The crude product was used for the next step without further purification.

L-leucine (1 eq) and $NaBH_3CN$ (2.2 eq) were dissolved in methanol with ice bath, then formaldehyde (2.2 eq) were added into the reaction dropwise. The reaction was stirred for 4 hr and concentrated on the rotary evaporator before running column purification to afford white solid N,N-dimethyl leucine.

N,N-dimethyl leucine (1 eq), DIPEA, (1.2 eq), and HATU (1.2) were added dry DMF and stirred for 30 min before adding crude product 2-amino-6-azido-N-(2,3-dihydroxy-4-(5-(2-oxohexahydro-1H-thieno[3,4-d]imidazol-4-yl)pentanamido)butyl)hexanamide (1.5 eq). The resulting reaction was stirred at room temperature for 24 hr before quenching with saturated $NaHCO_3$ and extracting with ethyl acetate. The extras were combined and concentrated before performing column purification to get the final compound 6-azido-N-(2,3-dihydroxy-4-(5-(2-oxohexahydro-1H-thieno[3,4-d]imidazol-4-yl)pentanamido)butyl)-2-(2-(dimethylamino)-4-methylpentanamido)hexanamide (Candidate C). This synthesis is illustrated in Scheme C below.

Scheme C

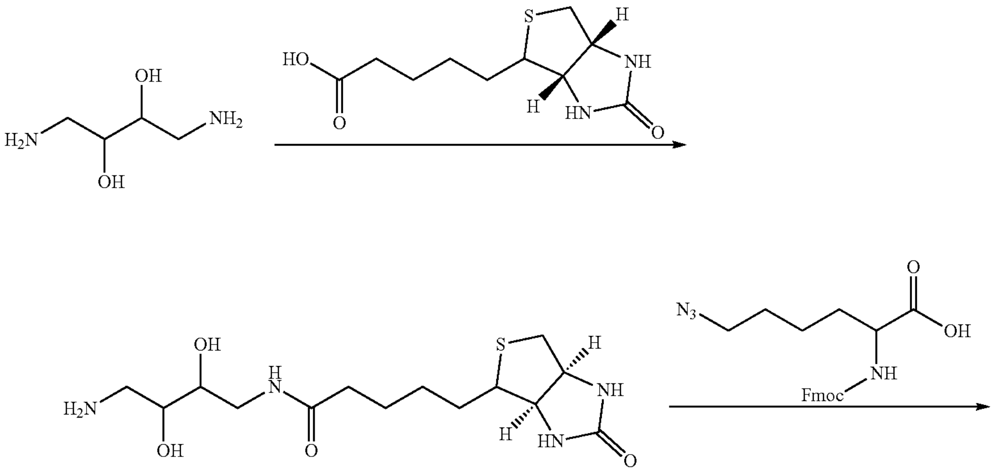

-continued

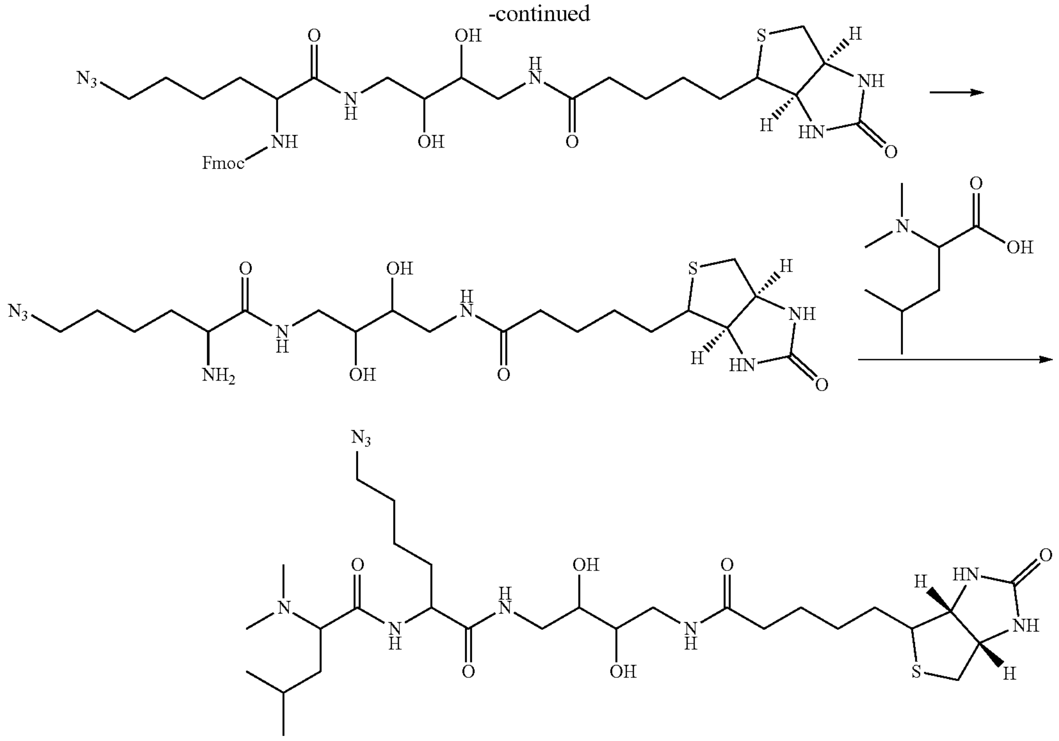

Candidate C

Synthesis of Candidate D.

N2-(((9H-fluoren-9-yl)methoxy)carbonyl)-N6-diazolysine (1 eq), DIPEA, (1.2 eq), and HATU (1.2) were added dry DMF and stirred for 30 min before adding compound 2-((tert-butyldimethylsilyl)oxy)ethan-1-amine (1.2 eq). The resulting reaction was stirred at room temperature for 24 hr before quenching with saturated $NaHCO_3$ and extracting with ethyl acetate. The extras were combined and concentrated before performing column purification to afford the compound (9H-fluoren-9-yl)methyl (6-azido-1-((2-((tert-butyldimethylsilyl)oxy) ethyl)amino)-1-oxohexan-2-yl)carbamate (d1).

Compound d1 was dissolved in piperidine DMF and stirred for 2 hr to deprotect the Fmoc group and the mixture was vaporized on the rotary evaporator. The crude product was used for the next step without further purification. L-leucine (1 eq) and $NaBH_3CN$ (2.2 eq) were dissolved in methanol with ice bath, then formaldehyde (2.2 eq) were added into the reaction dropwise. The reaction was stirred for 4 hr and concentrated on the rotary evaporator before running column purification to afford white solid N,N-dimethyl leucine.

N,N-dimethyl leucine (1 eq), DIPEA, (1.2 eq), and HATU (1.2) were added dry DMF and stirred for 30 min before adding crude product 2-amino-6-azido-N-(2-((tert-butyldimethylsilyl)oxy)ethyl)hexanamide. The resulting reaction was stirred at room temperature for 24 hr before quenching with saturated $NaHCO_3$ and extracting with ethyl acetate. The extras were combined and concentrated before performing column purification to get the intermediate product 6-azido-N-(2-((tert-butyldimethylsilyl)oxy)ethyl)-2-(2-(dimethylamino)-4-methylpentanamido)hexanamide. Then, the intermediate product was treated with TBAF in THF and the TBS group was deprotected to get the compound 6-azido-2-(2-(dimethylamino)-4-methylpentanamido)-N-(2-hydroxyethyl)hexanamide (d2).

Biotin-PEG4-OH (1 eq), DIPEA, (1.2 eq), and HATU (1.2) were added dry DMF and stirred for 30 min before adding compound d2 was added. The resulting reaction was stirred at room temperature for 24 hr before quenching with saturated $NaHCO_3$ and extracting with ethyl acetate. The extras were combined and concentrated before performing column purification to afford the final compound (Candidate D). This synthesis is illustrated in Scheme D below.

Scheme D

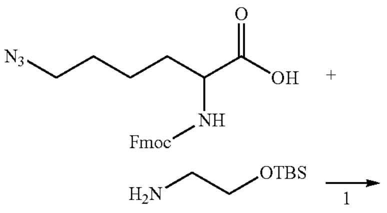

-continued

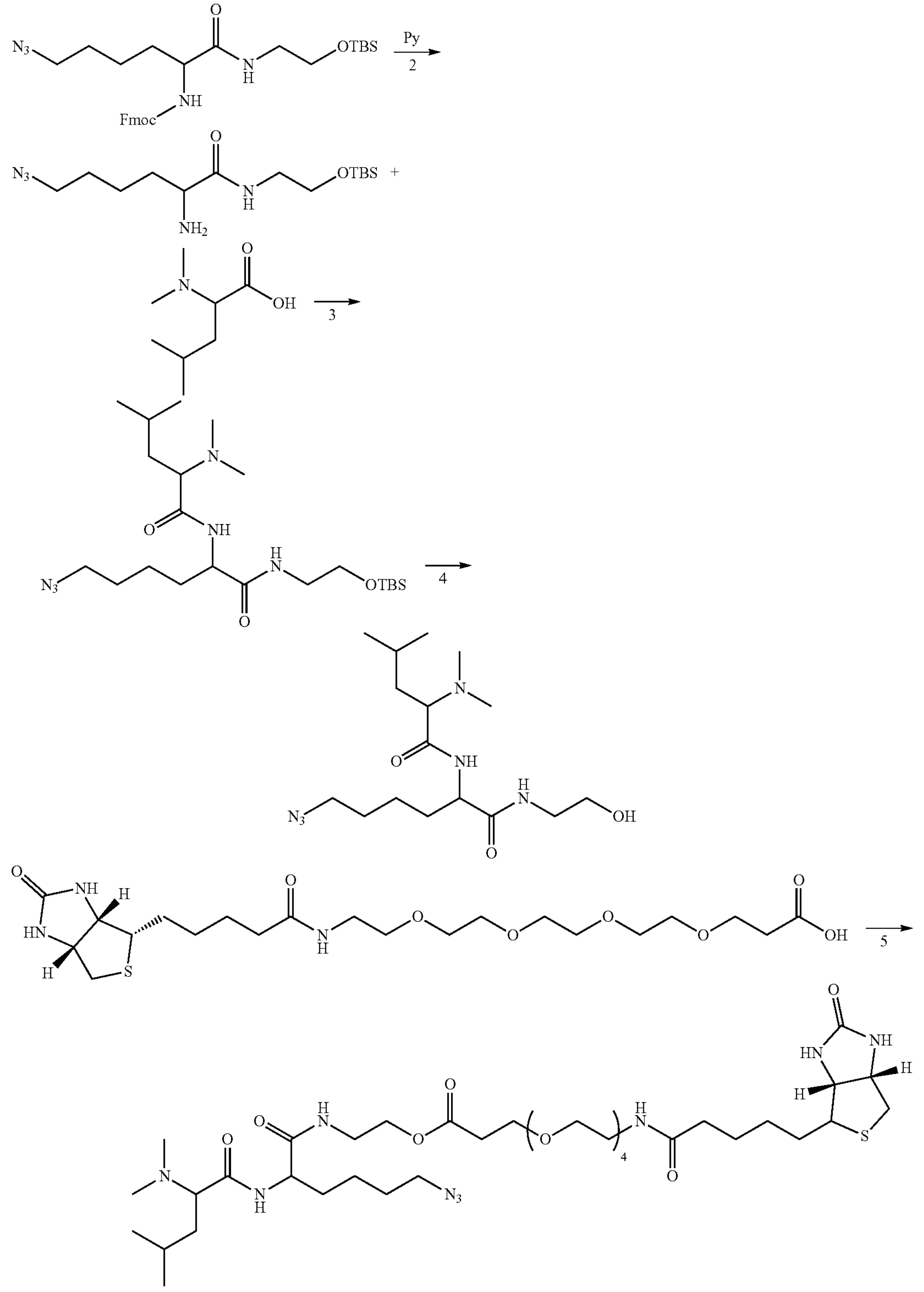

Synthesis of Candidate E. The intermediate compound d2 was made following the same scheme mentioned above.

5-(2-oxohexahydro-1H-thieno[3,4-d]imidazol-4-yl)pentanoic acid (1 eq), DIPEA, (1.2 eq), and HATU (1.2) were added dry DMF and stirred for 30 min before adding 1-amino-2-methylpropan-2-ol (1.2 eq). The resulting reaction was stirred at room temperature for 24 hr before filtering to get the white solid N-(2-hydroxy-2-methylpropyl)-5-(2-oxohexahydro-1H-thieno[3,4-d]imidazol-4-yl)pentanamide.

Triethylamine (20 eq) and dichlorodiphenylsilane (50 eq) were added in sequence to a solution of N-(2-hydroxy-2-methylpropyl)-5-(2-oxohexahydro-1H-thieno[3,4-d]imidazol-4-yl)pentanamide (1 equiv) in DCM and the resulting solution was stirred for 2 h at room temperature. The compound d2 in DCM was added and the solution was stirred for 18 h at room temperature. The reaction mixture was diluted with aqueous $NaHCO_3$ and the layers that formed were separated. The aqueous layer was extracted with DCM, and the organic layers were combined. The combined organic layers were dried over sodium sulfate. The dried solution was filtered and the filtrate was concentrated by rotary evaporation. The residue obtained was purified by flash column chromatography to afford the cleavable Biotin-DiLeu-Azide (Candidate E). This synthesis is illustrated in Scheme E below.

Scheme E

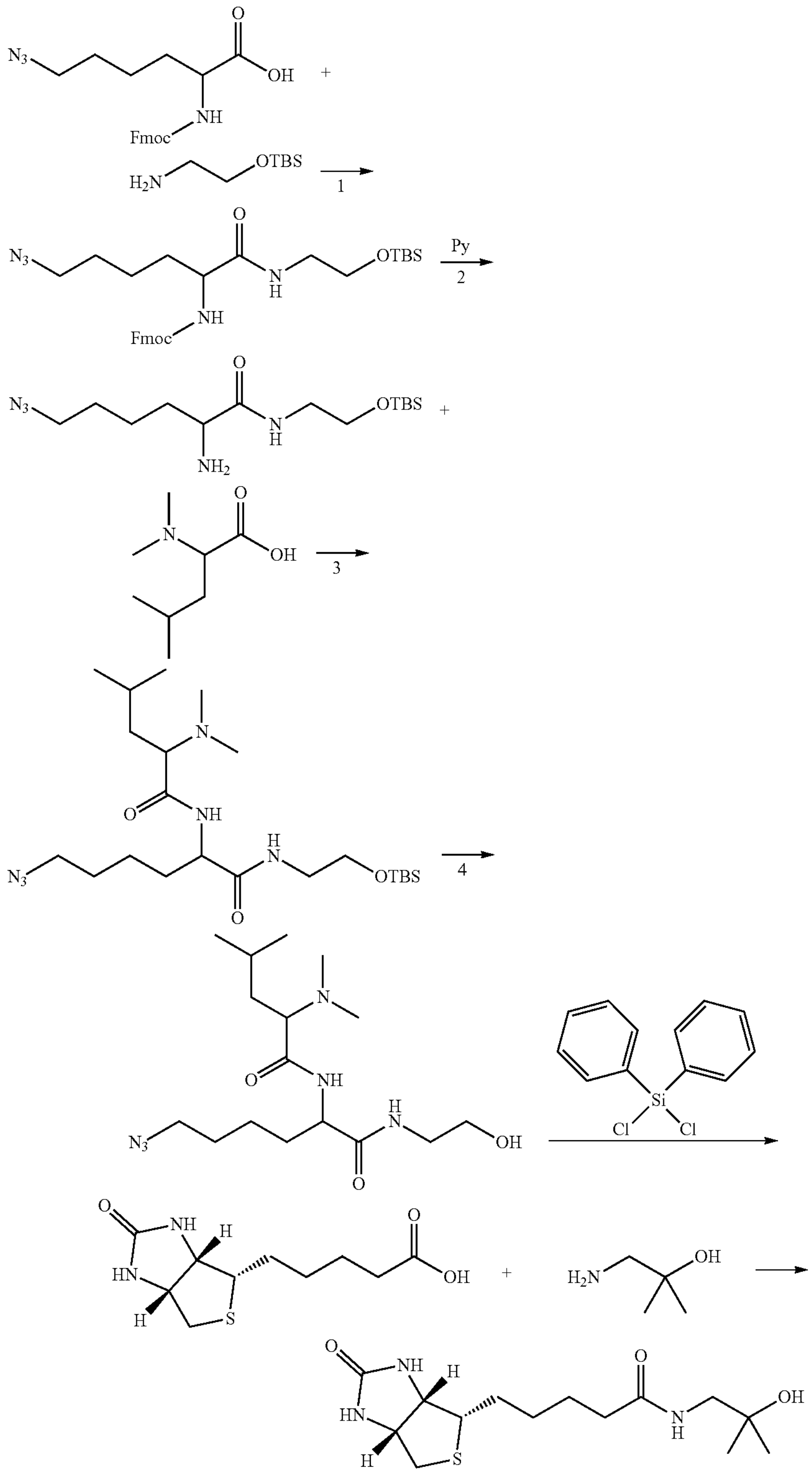

-continued

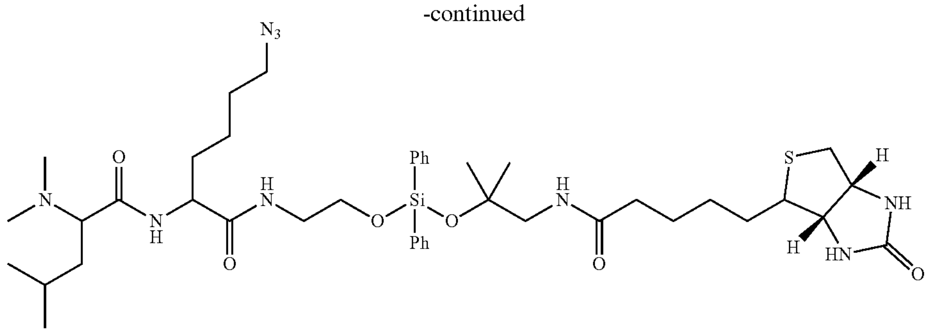

Candidate E

Synthesis of DADPS Linker-1.

Figure 18:
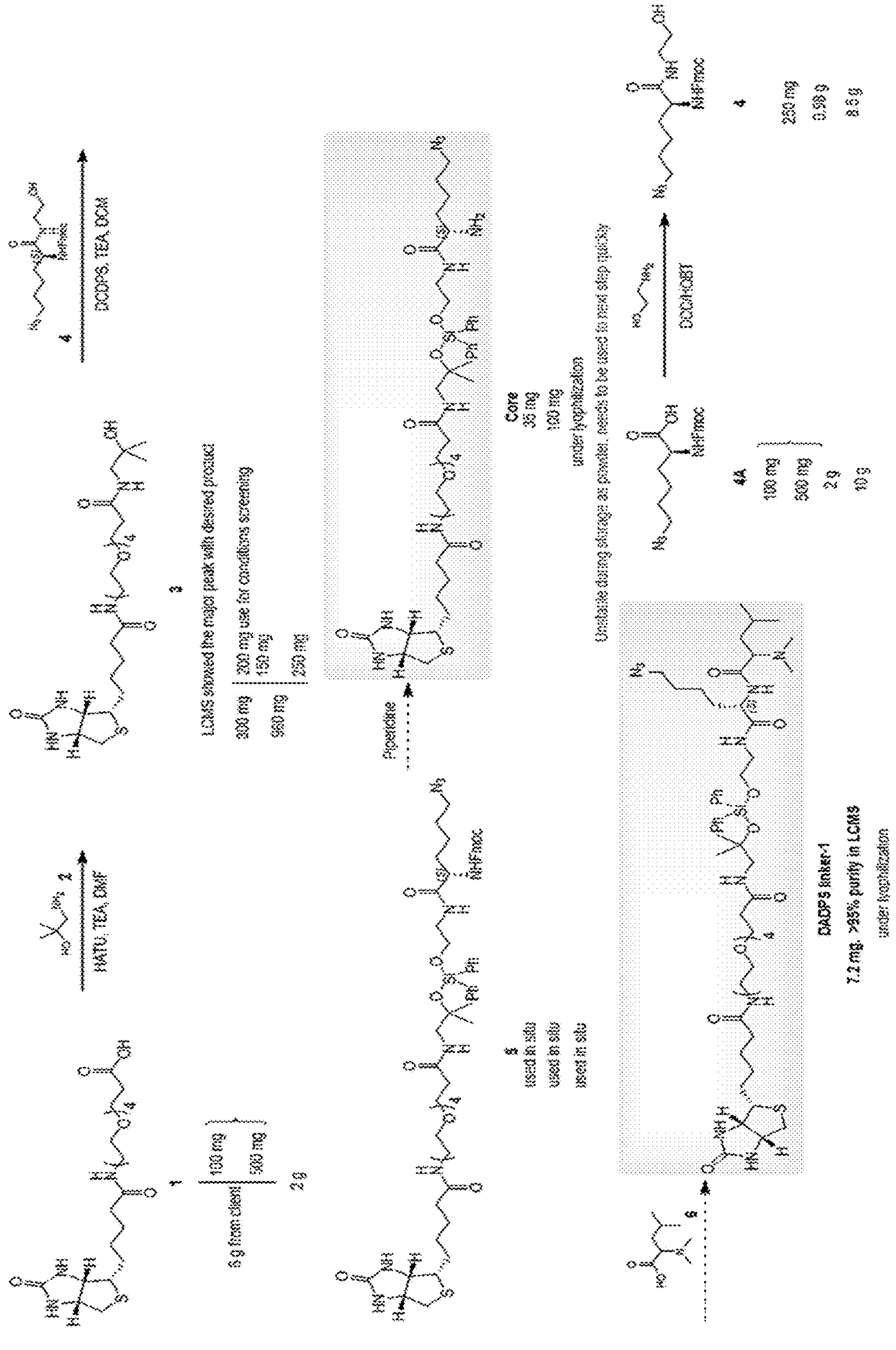
FIG. 18 shows synthetic route of cDBA tag candidate named DADPS linker-1.

FIG. 18 shows cDBA tag candidate containing a DADPS linker and a PEG-biotin linker using a synthetic route similar to those described above. The reporter ion moiety is not limited to DiLeu as the reporter group and may comprise other dimethylated, diethylated and asymmetric alkylated amino acid (D and L) structures. For example, in an embodiment, the isobaric tag portion can comprise dimethyl valine, diethyl valine, and/or asymmetric alkylated valine; dimethyl alanine, diethyl alanine, and/or asymmetric alkylated alanine. Heavy isotopes such as $^{13}C$, $^{2}H$, $^{15}N$, $^{18}O$ may be present at any atom or in any combination in the reporter group.

Having now fully described the present invention in some detail by way of illustration and examples for purposes of clarity of understanding, it will be obvious to one of ordinary skills in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components, or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

REFERENCES

1. Collins, F. S., Lander, E. S., Rogers, J., Waterston, R. H., and Int Human Genome Sequencing, C. (2004) Finishing the euchromatic sequence of the human genome. Nature 431, 931-945
2. Jensen, O. N. (2004) Modification-specific proteomics: characterization of post-translational modifications by mass spectrometry. Current Opinion in Chemical Biology 8, 33-41
3. Chaiyawat, P., Netsirisawan, P., Svasti, J., and Champattanachai, V. (2014) Aberrant O-GlcNAcylated proteins: new perspectives in breast and colorectal cancer. Frontiers in Endocrinology 5
4. Morino, K., Petersen, K. F., Dufour, S., Befroy, D., Frattini, J., Shatzkes, N., Neschen, S., White, M. F., Bilz, S., Sono, S., Pypaert, M., and Shulman, G. I. (2005) Reduced mitochondrial density and increased IRS-1 serine phosphorylation in muscle of insulin-resistant offspring of type 2 diabetic parents. Journal of Clinical Investigation 115, 3587-3593

5. Martin, L., Latypova, X., and Terro, F. (2011) Post-translational modifications of tau protein: Implications for Alzheimer's disease. Neurochemistry International 58, 458-471
6. Swaney, D. L., Beltrao, P., Starita, L., Guo, A., Rush, J., Fields, S., Krogan, N. J., and Villen, J. (2013) Global analysis of phosphorylation and ubiquitylation cross-talk in protein degradation. Nature Methods 10, 676-+
7. Yao, Q., Li, H., Liu, B. Q., Huang, X. Y., and Guo, L. (2011) SUMOylation-regulated Protein Phosphorylation, Evidence from Quantitative Phosphoproteomics Analyses. Journal of Biological Chemistry 286, 27342-27349
8. Lu, Z. K., Cheng, Z. Y., Zhao, Y. M., and Volchenboum, S. L. (2011) Bioinformatic Analysis and Post-Translational Modification Crosstalk Prediction of Lysine Acetylation. Plos One 6
9. Bulaj, G., Kortemme, T., and Goldenberg, D. P. (1998) Ionization-reactivity relationships for cysteine thiols in polypeptides. Biochemistry 37, 8965-8972
10. Reddie, K. G., and Carroll, K. S. (2008) Expanding the functional diversity of proteins through cysteine oxidation. Current Opinion in Chemical Biology 12, 746-754
11. Nakamura, T., Tu, S. C., Akhtar, M. W., Sunico, C. R., Okamoto, S. I., and Lipton, S. A. (2013) Aberrant Protein S-Nitrosylation in Neurodegenerative Diseases. Neuron 78, 596-614
12. Nakamura, T., Prikhodko, O. A., Pirie, E., Nagar, S., Akhtar, M. W., Oh, C. K., McKercher, S. R., Ambasudhan, R., Okamoto, S., and Lipton, S. A. (2015) Aberrant protein S-nitrosylation contributes to the pathophysiology of neurodegenerative diseases. Neurobiology of Disease 84, 99-108
13. Castro, R., Pinzón, H. S., and Alvis-Guzman, N. (2015) A systematic review of observational studies on oxidative/nitrosative stress involvement in dengue pathogenesis. Colomb Med (Cali) 46, 135-143
14. Filipović, D., Todorović, N., Bernardi, R. E., and Gass, P. (2017) Oxidative and nitrosative stress pathways in the brain of socially isolated adult male rats demonstrating depressive- and anxiety-like symptoms. Brain Struct Funct 222, 1-20
15. Maes, M., Stevens, W. J., Declerck, L. S., Bridts, C. H., Peeters, D., Schotte, C., and Cosyns, P. (1993) Significantly increased expression of T-cell activation markers (interleukin-2 and HLA-DR) in depression: further evidence for an inflammatory process during that illness. Prog Neuropsychopharmacol Biol Psychiatry 17, 241-255
16. Marletta, M. A., Hurshman, A. R., and Rusche, K. M. (1998) Catalysis by nitric oxide synthase. Current Opinion in Chemical Biology 2, 656-663
17. Heinrich, T. A., da Silva, R. S., Miranda, K. M., Switzer, C. H., Wink, D. A., and Fukuto, J. M. (2013) Biological nitric oxide signalling: chemistry and terminology. British Journal of Pharmacology 169, 1417-1429
18. Hess, D. T., Matsumoto, A., Kim, S. O., Marshall, H. E., and Stamler, J. S. (2005) Protein S-nitrosylation: Purview and parameters. Nature Reviews Molecular Cell Biology 6, 150-166
19. Sayre, L. M., Perry, G., and Smith, M. A. (2008) Oxidative stress and neurotoxicity. Chemical Research in Toxicology 21, 172-188
20. Chung, K. K. K., Thomas, B., Li, X. J., Pletnikova, O., Troncoso, J. C., Marsh, L., Dawson, V. L., and Dawson, T. M. (2004) S-nitrosylation of Parkin regulates ubiquitination and compromises Parkin's protective function. Science 304, 1328-1331
21. Uehara, T., Nakamura, T., Yao, D. D., Shi, Z. Q., Gu, Z. Z., Ma, Y. L., Masliah, E., Nomura, Y., and Lipton, S. A. (2006) S-Nitrosylated protein-disulphide isomerase links protein misfolding to neurodegeneration. Nature 441, 513-517
22. Shankar, G. M., Bloodgood, B. L., Townsend, M., Walsh, D. M., Selkoe, D. J., and Sabatini, B. L. (2007) Natural oligomers of the Alzheimer amyloid-beta protein induce reversible synapse loss by modulating an NMDA-type glutamate receptor-dependent signaling pathway. Journal of Neuroscience 27, 2866-2875
23. Qu, J., Nakamura, T., Cao, G., Holland, E. A., McKercher, S. R., and Lipton, S. A. (2011) S-Nitrosylation activates Cdk5 and contributes to synaptic spine loss induced by beta-amyloid peptide. Proceedings of the National Academy of Sciences of the United States of America 108, 14330-14335
24. Zhang, P., Yu, P. C., Tsang, A. H. K., Chen, Y., Fu, A. K. Y., Fu, W. Y., Chung, K. K., and Ip, N. Y. (2010) S-Nitrosylation of Cyclin-Dependent Kinase 5 (Cdk5) Regulates Its Kinase Activity and Dendrite Growth During Neuronal Development. Journal of Neuroscience 30, 14366-14370
25. Dixon, S. J., and Stockwell, B. R. (2009) Identifying druggable disease-modifying gene products. Current Opinion in Chemical Biology 13, 549-555
26. Parker, C. G., Galmozzi, A., Wang, Y. J., Correia, B. E., Sasaki, K., Joslyn, C. M., Kim, A. S., Cavallaro, C. L., Lawrence, R. M., Johnson, S. R., Narvaiza, I., Saez, E., and Cravatt, B. F. (2017) Ligand and Target Discovery by Fragment-Based Screening in Human Cells. Cell 168, 527-+
27. Deng, H., Lei, Q., Wu, Y. P., He, Y., and Li, W. M. (2020) Activity-based protein profiling: Recent advances in medicinal chemistry. European Journal of Medicinal Chemistry 191
28. Chen, X., Wong, Y. K., Wang, J. G., Zhang, J. B., Lee, Y. M., Shen, H. M., Lin, Q. S., and Hua, Z. C. (2017) Target identification with quantitative activity based protein profiling (ABPP). Proteomics 17
29. Roberts, A. M., Ward, C. C., and Nomura, D. K. (2017) Activity-based protein profiling for mapping and pharmacologically interrogating proteome-wide ligandable hotspots. Current Opinion in Biotechnology 43, 25-33
30. Moellering, R. E., and Cravatt, B. F. (2012) How Chemoproteomics Can Enable Drug Discovery and Development. Chemistry & Biology 19, 11-22
31. Chakrabarty, S., Kahler, J. P., van de Plassche, M. A. T., Vanhoutte, R., and Verhelst, S. H. L. (2019) Recent Advances in Activity-Based Protein Profiling of Proteases. Activity-Based Protein Profiling 420, 253-281
32. Yang, P. Y., and Liu, K. (2015) Activity-Based Protein Profiling: Recent Advances in Probe Development and Applications. Chembiochem 16, 712-724
33. Weerapana, E., Wang, C., Simon, G. M., Richter, F., Khare, S., Dillon, M. B. D., Bachovchin, D. A., Mowen, K., Baker, D., and Cravatt, B. F. (2010) Quantitative reactivity profiling predicts functional cysteines in proteomes. Nature 468, 790-U779
34. Weerapana, E., Wang, C., Simon, G. M., Richter, F., Khare, S., Dillon, M. B. D., Bachovchin, D. A., Mowen, K., Baker, D., and Cravatt, B. F. (2011) Quantitative reactivity profiling predicts functional cysteines in proteomes. Abstracts of Papers of the American Chemical Society 241

35. Sieber, S. A., and Cravatt, B. F. (2006) Analytical platforms for activity-based protein profiling—exploiting the versatility of chemistry for functional proteomics. Chemical Communications, 2311-2319
36. Rauniyar, N., and Yates, J. R. (2014) Isobaric Labeling-Based Relative Quantification in Shotgun Proteomics. Journal of Proteome Research 13, 5293-5309
37. Nunez, E. V., Domont, G. B., and Nogueira, F. C. S. (2017) iTRAQ-Based Shotgun Proteomics Approach for Relative Protein Quantification. In Multiplex Biomarker Techniques: Methods and Applications (Guest, P. C., ed) Vol. 1546 pp. 267-274
38. Li, J. M., Van Vranken, J. G., Vaites, L. P., Schweppe, D. K., Huttlin, E. L., Etienne, C., Nandhikonda, P., Viner, R., Robitaille, A. M., Thompson, A. H., Kuhn, K., Pike, I., Bomgarden, R. D., Rogers, J. C., Gygi, S. P., and Paulo, J. A. (2020) TMTpro reagents: a set of isobaric labeling mass tags enables simultaneous proteome-wide measurements across 16 samples. Nature Methods 17, 399-+
39. Xiang, F., Ye, H., Chen, R. B., Fu, Q., and Li, L. J. (2010) N,N-Dimethyl Leucines as Novel Isobaric Tandem Mass Tags for Quantitative Proteomics and Peptidomics. Analytical Chemistry 82, 2817-2825
40. Ficarro, S. B., McCleland, M. L., Stukenberg, P. T., Burke, D. J., Ross, M. M., Shabanowitz, J., Hunt, D. F., and White, F. M. (2002) Phosphoproteome analysis by mass spectrometry and its application to *Saccharomyces cerevisiae*. Nature Biotechnology 20, 301-305
41. Stensballe, A., Andersen, S., and Jensen, O. N. (2001) Characterization of phosphoproteins from electrophoretic gels by nanoscale Fe(Ill) affinity chromatography with off-line mass spectrometry analysis. Proteomics 1, 207-222
42. Larsen, M. R., Thingholm, T. E., Jensen, O. N., Roepstorff, P., and Jorgensen, T. J. D. (2005) Highly selective enrichment of phosphorylated peptides from peptide mixtures using titanium dioxide microcolumns. Molecular & Cellular Proteomics 4, 873-886
43. Yang, Z. P., and Hancock, W. S. (2004) Approach to the comprehensive analysis of glycoproteins isolated from human serum using a multi-lectin affinity column. Journal of Chromatography A 1053, 79-88
44. Tian, Y. A., Zhou, Y., Elliott, S., Aebersold, R., and Zhang, H. (2007) Solid-phase extraction of N-linked glycopeptides. Nature Protocols 2, 334-339
45. Zhao, Y. M., and Jensen, O. N. (2009) Modification-specific proteomics: Strategies for characterization of post-translational modifications using enrichment techniques. Proteomics 9, 4632-4641
46. Bantscheff, M., Schirle, M., Sweetman, G., Rick, J., and Kuster, B. (2007) Quantitative mass spectrometry in proteomics: a critical review. Analytical and Bioanalytical Chemistry 389, 1017-1031
47. Gygi, S. P., Rist, B., Gerber, S. A., Turecek, F., Gelb, M. H., and Aebersold, R. (1999) Quantitative analysis of complex protein mixtures using isotope-coded affinity tags. Nature Biotechnology 17, 994-999
48. Xiang, F., Ye, H., Chen, R., Fu, Q., and Li, L. (2010) N, N-dimethyl leucines as novel isobaric tandem mass tags for quantitative proteomics and peptidomics. Analytical chemistry 82, 2817-2825
49. Frost, D. C., Greer, T., and Li, L. (2014) High-resolution enabled 12-plex DiLeu isobaric tags for quantitative proteomics. Analytical chemistry 87, 1646-1654
50. Hao, L., Zhong, X., Greer, T., Ye, H., and Li, L. (2015) Relative quantification of amine-containing metabolites using isobaric N, N-dimethyl leucine (DiLeu) reagents via LC-ESI-MS/MS and CE-ESI-MS/MS. Analyst 140, 467-475
51. Hebert, A. S., Merrill, A. E., Bailey, D. J., Still, A. J., Westphall, M. S., Strieter, E. R., Pagliarini, D. J., and Coon, J. J. (2013) Neutron-encoded mass signatures for multiplexed proteome quantification. Nature Methods 10, 332-+
52. Sleno, L. (2012) The use of mass defect in modern mass spectrometry. Journal of Mass Spectrometry 47, 226-236
53. Feng, Y., Chen, B. M., Yu, Q. Y., Zhong, X. F., Frost, D. C., Ikonomidou, C., and Li, L. J. (2019) Isobaric Multiplex Labeling Reagents for Carbonyl-Containing Compound (SUGAR) Tags: A Probe for Quantitative Glycomic Analysis. Analytical Chemistry 91, 3141-3146
54. Feng, Y., Li, M. Y., Lin, Y. Y., Chen, B. M., and Li, L. J. (2019) Multiplex Quantitative Glycomics Enabled by Periodate Oxidation and Triplex Mass Defect Isobaric Multiplex Reagents for Carbonyl-Containing Compound Tags. Analytical Chemistry 91, 11932-11937
55. Wong, J., Chilkoti, A., and Moy, V. T. (1999) Direct force measurements of the streptavidin-biotin interaction. Biomolecular Engineering 16, 45-55
56. Hems, E. S., Wagstaff, B. A., Saalbach, G., and Field, R. A. (2018) CuAAC click chemistry for the enhanced detection of novel alkyne-based natural product toxins. Chemical Communications 54, 12234-12237
57. Meldal, M., and Diness, F. (2020) Recent Fascinating Aspects of the CuAAC Click Reaction. Trends in Chemistry 2, 569-584
58. Chio, T. I., and Bane, S. L. (2020) Click Chemistry Conjugations. Antibody-Drug Conjugates: Methods and Protocols 2078, 83-97
59. Araki, K., Kusano, H., Sasaki, N., Tanaka, R., Hatta, T., Fukui, K., and Natsume, T. (2016) Redox Sensitivities of Global Cellular Cysteine Residues under Reductive and Oxidative Stress. Journal of Proteome Research 15, 2548-2559
60. Qu, Z., Meng, F. J., Bomgarden, R. D., Viner, R. I., Li, J. L., Rogers, J. C., Cheng, J. L., Greenlief, C. M., Cui, J. K., Lubahn, D. B., Sun, G. Y., and Gu, Z. Z. (2014) Proteomic Quantification and Site-Mapping of S-Nitrosylated Proteins Using Isobaric iodoTMT Reagents. Journal of Proteome Research 13, 3200-3211
61. Jaffrey, S. R., Erdjument-Bromage, H., Ferris, C. D., Tempst, P., and Snyder, S. H. (2001) Protein S-nitrosylation: a physiological signal for neuronal nitric oxide. Nature Cell Biology 3, 193-197
62. Chen, Y. J., Ching, W. C., and Lin, Y. P. (2013) Methods for detection and characterization of protein S-nitrosylation. Methods 62, 138-150
63. Lopez-Sanchez, L. M., Muntane, J., de la Mata, M., and Rodriguez-Ariza, A. (2009) Unraveling the S-nitrosoproteome: Tools and strategies. Proteomics 9, 808-818
64. Giron, P., Dayon, L., and Sanchez, J. C. (2011) CYSTEINE TAGGING FOR MS-BASED PROTEOMICS. Mass Spectrometry Reviews 30, 366-395
65. Petritis, K., Chaimbault, P., Elfakir, C., and Dreux, M. (2000) Parameter optimization for the analysis of underivatized protein amino acids by liquid chromatography and ionspray tandem mass spectrometry. Journal of Chromatography A 896, 253-263
66. Nie, L. T., Zhu, M. R., Sun, S. N., Zhai, L. H., Wu, Z. X., Qian, L. L., and Tan, M. J. (2016) An optimization of the LC-MS/MS workflow for deep proteome profiling on an Orbitrap Fusion. Analytical Methods 8, 425-434

67. Lange, V., Picotti, P., Domon, B., and Aebersold, R. (2008) Selected reaction monitoring for quantitative proteomics: a tutorial. Molecular Systems Biology 4

68. Speers, A. E., Adam, G. C., and Cravatt, B. F. (2003) Activity-based protein profiling in vivo using a copper (I)-catalyzed azide-alkyne 3+2 cycloaddition. Journal of the American Chemical Society 125, 4686-4687

69. Ovaa, H., van Swieten, P. F., Kessler, B. M., Leeuwenburgh, M. A., Fiebiger, E., van den Nieuwendijk, A., Galardy, P. J., van der Marel, G. A., Ploegh, H. L., and Overkleeft, H. S. (2003) Chemistry in living cells: Detection of active proteasomes by a two-step labeling strategy. Angewandte Chemie-International Edition 42, 3626-3629

70. Evans, M. J., and Cravatt, B. F. (2006) Mechanism-based profiling of enzyme families. Chemical Reviews 106, 3279-3301

71. Paulick, M. G., and Bogyo, M. (2008) Application of activity-based probes to the study of enzymes involved in cancer progression. Current Opinion in Genetics & Development 18, 97-106

72. Speers, A. E., and Cravatt, B. F. (2005) A tandem orthogonal proteolysis strategy for high-content chemical proteomics. Journal of the American Chemical Society 127, 10018-10019

73. Su, Y., Ge, J. Y., Zhu, B. W., Zheng, Y. G., Zhu, Q., and Yao, S. Q. (2013) Target identification of biologically active small molecules via in situ methods. Current Opinion in Chemical Biology 17, 768-775

74. Holmberg, A., Blomstergren, A., Nord, O., Lukacs, M., Lundeberg, J., and Uhlen, M. (2005) The biotin-streptavidin interaction can be reversibly broken using water at elevated temperatures. Electrophoresis 26, 501-510

75. Hyre, D. E., Amon, L. M., Penzotti, J. E., Le Trong, I., Stenkamp, R. E., Lybrand, T. P., and Stayton, P. S. (2002) Early mechanistic events in biotin dissociation from streptavidin. Nature Structural Biology 9, 582-585

76. Rudolf, G. C., Heydenreuter, W., and Sieber, S. A. (2013) Chemical proteomics: ligation and cleavage of protein modifications. Current Opinion in Chemical Biology 17, 110-117

77. Szychowski, J., Mahdavi, A., Hodas, J. J. L., Bagert, J. D., Ngo, J. T., Landgraf, P., Dieterich, D. C., Schuman, E. M., and Tirrell, D. A. (2010) Cleavable Biotin Probes for Labeling of Biomolecules via Azide-Alkyne Cycloaddition. Journal of the American Chemical Society 132, 18351-18360

78. Fonovic, M., Verhelst, S. H. L., Sorum, M. T., and Bogyo, M. (2007) Proteomics evaluation of chemically cleavable activity-based probes. Molecular & Cellular Proteomics 6, 1761-1770

79. Geurink, P. P., Florea, B. I., Li, N., Witte, M. D., Verasdonck, J., Kuo, C. L., van der Marel, G. A., and Overkleeft, H. S. (2010) A Cleavable Linker Based on the Levulinoyl Ester for Activity-Based Protein Profiling. Angewandte Chemie-International Edition 49, 6802-6805

80. Yonezawa, H., Nishiyama, Y., Takeo, K., Iwatsubo, T., Tomita, T., Yokoshima, S., and Fukuyama, T. (2014) New photocleavable linker: alpha-Thioacetophenone-type linker. Bioorganic & Medicinal Chemistry Letters 24, 2831-2833

81. Craft, G. E., Chen, A., and Nairn, A. C. (2013) Recent advances in quantitative neuroproteomics. Methods 61, 186-218

82. Fauq, A. H., Kache, R., Khan, M. A., and Vega, I. E. (2006) Synthesis of acid-cleavable light isotope-coded affinity tags (ICAT-L) for potential use in proteomic expression profiling analysis. Bioconjugate Chemistry 17, 248-254

83. Neckers, D. C., Kellogg, R. M., Prins, W. L., and Schoustr. B. (1971) DEVELOPMENTAL PHOTO-CHEMISTRY—NORRISH TYPE-II REACTION. Journal of Organic Chemistry 36, 1838-&

84. Black, L. S., Monroe, W. E., Lee, J. C., and Robertson, J. L. (1994) ATRIAL-NATRIURETIC-PEPTIDE. Compendium on Continuing Education for the Practicing Veterinarian 16, 717-&

85. Sun, N. N., Wang, Y., Wang, J., Sun, W. C., Yang, J. B., and Liu, N. (2020) Highly Efficient Peptide-Based Click Chemistry for Proteomic Profiling of Nascent Proteins. Analytical Chemistry 92, 8292-8297

86. Rudolf, G. C., and Sieber, S. A. (2013) Copper-Assisted Click Reactions for Activity-Based Proteomics: Fine-Tuned Ligands and Refined Conditions Extend the Scope of Application. Chembiochem 14, 2447-2455

87. Frost, D. C., Feng, Y., and Li, L. J. (2020) 21-plex DiLeu Isobaric Tags for High-Throughput Quantitative Proteomics. Analytical Chemistry 92, 8228-8234

88. Wang, C., and Cravatt, B. F. (2014) A Chemoproteomic Platform To Quantitatively Map Targets Of Lipid-Derived Electrophiles. Protein Science 23, 191-191

89. Zhou, Y. N., Wynia-Smith, S. L., Couvertier, S. M., Kalous, K. S., Marletta, M. A., Smith, B. C., and Weerapana, E. (2016) Chemoproteomic Strategy to Quantitatively Monitor Transnitrosation Uncovers Functionally Relevant S-Nitrosation Sites on Cathepsin D and HADH2. Cell Chemical Biology 23, 727-737

90. Bateman, L. A., Zaro, B. W., Miller, S. M., and Pratt, M. R. (2018) An Alkyne-Aspirin Chemical Reporter for the Detection of Aspirin-Dependent Protein Modification in Living Cells (vol 135, pg 14568, 2013). Journal of the American Chemical Society 140, 4954-4954

91. Bak, D. W., Gao, J. J., Wang, C., and Weerapana, E. (2018) A Quantitative Chemoproteomic Platform to Monitor Selenocysteine Reactivity within a Complex Proteome. Cell Chemical Biology 25, 1157-+

92. Wijasa, T. S., Sylvester, M., Brocke-Ahmadinejad, N., Schwartz, S., Santarelli, F., Gieselmann, V., Klockgether, T., Brosseron, F., and Heneka, M. T. (2020) Quantitative proteomics of synaptosome S-nitrosylation in Alzheimer's disease. Journal of Neurochemistry 152, 710-726

93. Zhao, Q. F., Yu, J. T., and Tan, L. (2015) S-Nitrosylation in Alzheimer's disease. Molecular Neurobiology 51, 268-280

94. Abrams, A. J., Farooq, A., and Wang, G. F. (2011) S-Nitrosylation of ApoE in Alzheimer's Disease. Biochemistry 50, 3405-3407

95. Nakamura, T., and Lipton, S. A. (2013) Emerging Role of Protein-Protein Transnitrosylation in Cell Signaling Pathways. Antioxidants & Redox Signaling 18, 239-249

96. Qu, J., Nakamura, T., Holland, E. A., McKercher, S. R., and Lipton, S. A. (2012) S-nitrosylation of Cdk5 Potential implications in amyloid-beta-related neurotoxicity in Alzheimer disease. Prion 6, 364-370

97. Retzlaff, M., Stahl, M., Eberl, H. C., Lagleder, S., Beck, J., Kessler, H., and Buchner, J. (2009) Hsp90 is regulated by a switch point in the C-terminal domain. Embo Reports 10, 1147-1153

98. Walker, A. K., Farg, M. A., Bye, C. R., McLean, C. A., Horne, M. K., and Atkin, J. D. (2010) Protein disulphide isomerase protects against protein aggregation and is S-nitrosylated in amyotrophic lateral sclerosis. Brain 133, 105-116

99. Chakravarti, R., Aulak, K. S., Fox, P. L., and Stuehr, D. J. (2010) GAPDH regulates cellular heme insertion into inducible nitric oxide synthase. Proceedings of the National Academy of Sciences of the United States of America 107, 18004-18009
100. Moskovitz, J. (2014) Detection and Localization of Methionine Sulfoxide Residues of Specific Proteins in Brain Tissue. Protein and Peptide Letters 21, 52-55
101. Sun, M. K., and Alkon, D. L. (2002) Carbonic anhydrase gating of attention: memory therapy and enhancement. Trends in Pharmacological Sciences 23, 83-89
102. Forrester, M. T., Foster, M. W., and Stamler, J. S. (2007) Assessment and application of the biotin switch technique for examining protein S-nitrosylation under conditions of pharmacologically induced oxidative stress. Journal of Biological Chemistry 282, 13977-13983
103. Mnatsakanyan, R., Markoutsa, S., Walbrunn, K., Roos, A., Verhelst, S. H. L., and Zahedi, R. P. (2019) Proteome-wide detection of S-nitrosylation targets and motifs using bioorthogonal cleavable-linker-based enrichment and switch technique. Nature Communications 10
104. Polanco, J. C., Li, C. Z., Bodea, L. G., Martinez-Marmol, R., Meunier, F. A., and Gotz, J. (2018) Amyloid-beta and tau complexity—towards improved biomarkers and targeted therapies. Nature Reviews Neurology 14, 22-39
105. Goedert, M. (2015) Alzheimer's and Parkinson's diseases: The prion concept in relation to assembled A beta, tau, and alpha-synuclein. Science 349
106. Glenner, G. G., and Wong, C. W. (2012) ALZHEIMER'S DISEASE: INITIAL REPORT OF THE PURIFICATION AND CHARACTERIZATION OF A NOVEL CEREBROVASCULAR AMYLOID PROTEIN (Reprinted from BIOCHEMICAL AND BIOPHYSICAL RESEARCH COMMUNICATIONS, vol 120, pg 885-890, 1984). Biochemical and Biophysical Research Communications 425, 534-539
107. Masters, C. L., Simms, G., Weinman, N. A., Multhaup, G., McDonald, B. L., and Beyreuther, K. (1985) AMYLOID PLAQUE CORE PROTEIN IN ALZHEIMER-DISEASE AND DOWN SYNDROME. Proceedings of the National Academy of Sciences of the United States of America 82, 4245-4249
108. Zareba-Koziol, M., Szwajda, A., Dadlez, M., Wyslouch-Cieszynska, A., and Lalowski, M. (2014) Global Analysis of S-nitrosylation Sites in the Wild Type (APP) Transgenic Mouse Brain-Clues for Synaptic Pathology. Molecular & Cellular Proteomics 13, 2288-2305
109. Gu, L. Q., and Robinson, R. A. S. (2016) High-throughput endogenous measurement of S-nitrosylation in Alzheimer's disease using oxidized cysteine-selective cPILOT. Analyst 141, 3904-3915
110. Gu, L. Q., and Robinson, R. A. S. (2016) Proteomic approaches to quantify cysteine reversible modifications in aging and neurodegenerative diseases. Proteomics Clinical Applications 10, 1159-1177
111. Hyman, B. T., and Trojanowski, J. Q. (1997) Editorial on consensus recommendations for the postmortem diagnosis of Alzheimer disease from the National Institute on Aging and the Reagan Institute working group on diagnostic criteria for the neuropathological assessment of Alzheimer disease. Journal of Neuropathology and Experimental Neurology 56, 1095-1097
112. Fagan, A. M., Mintun, M. A., Shah, A. R., Aldea, P., Roe, C. M., Mach, R. H., Marcus, D., Morris, J. C., and Holtzman, D. M. (2009) Cerebrospinal fluid tau and ptau(181) increase with cortical amyloid deposition in cognitively normal individuals: Implications for future clinical trials of Alzheimer's disease. Embo Molecular Medicine 1, 371-380
113. Fagan, A. M., Head, D., Shah, A. R., Marcus, D., Mintun, M., Morris, J. C., and Holtzman, D. M. (2009) Decreased Cerebrospinal Fluid A beta(42) Correlates with Brain Atrophy in Cognitively Normal Elderly. Annals of Neurology 65, 176-183
114. Backus, K. M., Correia, B. E., Lum, K. M., Forli, S., Horning, B. D., Gonzalez-Paez, G. E., Chatterjee, S., Lanning, B. R., Teijaro, J. R., Olson, A. J., Wolan, D. W., and Cravatt, B. F. (2016) Proteome-wide covalent ligand discovery in native biological systems. Nature 534, 570-+
115. Bar-Peled, L., Kemper, E. K., Suciu, R. M., Vinogradova, E. V., Backus, K. M., Horning, B. D., Paul, T. A., Ichu, T. A., Svensson, R. U., Olucha, J., Chang, M. W., Kok, B. P., Zhu, Z., Ihle, N. T., Dix, M. M., Jiang, P., Hayward, M. M., Saez, E., Shaw, R. J., and Cravatt, B. F. (2017) Chemical Proteomics Identifies Druggable Vulnerabilities in a Genetically Defined Cancer. Cell 171, 696-+
116. van Esbroeck, A. C. M., Janssen, A. P. A., Cognetta, A. B., Ogasawara, D., Shpak, G., van der Kroeg, M., Kantae, V., Baggelaar, M. P., de Vrij, F. M. S., Deng, H., Allara, M., Fezza, F., Lin, Z., van der Wel, T., Soethoudt, M., Mock, E. D., den Dulk, H., Baak, I. L., Florea, B. I., Hendriks, G., de Petrocellis, L., Overkleeft, H. S., Hankemeier, T., De Zeeuw, C. I., Di Marzo, V., Maccarrone, M., Cravatt, B. F., Kushner, S. A., and van der Stelt, M. (2017) Activity-based protein profiling reveals off-target proteins of the FAAH inhibitor BIA 10-2474. Science 356, 1084-1087
117. Deng, X., Weerapana, E., Ulanovskaya, O., Sun, F., Liang, H. H., Ji, Q. J., Ye, Y., Fu, Y., Zhou, L., Li, J. X., Zhang, H. Y., Wang, C., Alvarez, S., Hicks, L. M., Lan, L. F., Wu, M., Cravatt, B. F., and He, C. (2013) Proteome-wide Quantification and Characterization of Oxidation-Sensitive Cysteines in Pathogenic Bacteria. Cell Host & Microbe 13, 358-370
118. Medina-Cleghorn, D., Bateman, L. A., Ford, B., Heslin, A., Fisher, K. J., Dalvie, E. D., and Nomura, D. K. (2015) Mapping Proteome-Wide Targets of Environmental Chemicals Using Reactivity-Based Chemoproteomic Platforms. Chemistry & Biology 22, 1394-1405
119. Huang, Z., Ogasawara, D., Seneviratne, U. I., Cognetta, A. B., Ende, C. W. A., Nason, D. M., Lapham, K., Litchfield, J., Johnson, D. S., and Cravatt, B. F. (2019) Global Portrait of Protein Targets of Metabolites of the Neurotoxic Compound BIA 10-2474. Acs Chemical Biology 14, 192-197
120. Alcock, L. J., Perkins, M. V., and Chalker, J. M. (2018) Chemical methods for mapping cysteine oxidation. Chemical Society Reviews 47, 231-268
121. Lo Conte, M., and Carroll, K. S. (2013) The Redox Biochemistry of Protein Sulfenylation and Sulfinylation. Journal of Biological Chemistry 288, 26480-26488
122. Miseta, A., and Csutora, P. (2000) Relationship between the occurrence of cysteine in proteins and the complexity of organisms. Molecular Biology and Evolution 17, 1232-1239
123. Yang, J., Gupta, V., Tallman, K. A., Porter, N. A., Carroll, K. S., and Liebler, D. C. (2015) Global, in situ, site-specific analysis of protein S-sulfenylation. Nature Protocols 10, 1022-1037
124. Akter, S., Fu, L., Jung, Y., Lo Conte, M., Lawson, J. R., Lowther, W. T., Sun, R., Liu, K. K., Yang, J., and Carroll, K. S. (2018) Chemical proteomics reveals new targets of cysteine sulfinic acid reductase. Nature Chemical Biology 14, 995-+
125. Shetty, V., Spellman, D. S., and Neubert, T. A. (2007) Characterization by tandem mass spectrometry of stable cysteine sulfenic acid in a cysteine switch peptide of matrix metalloproteinases. Journal of the American Society for Mass Spectrometry 18, 1544-1551
126. Fedorova, M., Bollineni, R. C., and Hoffmann, R. (2014) PROTEIN CARBONYLATION AS A MAJOR HALLMARK OF OXIDATIVE DAMAGE: UPDATE OF ANALYTICAL STRATEGIES. Mass Spectrometry Reviews 33, 79-97
127. Tian, C. P., Liu, K. K., Sun, R., Fu, L., and Yang, J. (2018) Chemoproteomics Reveals Unexpected Lysine/Arginine-Specific Cleavage of Peptide Chains as a Potential Protein Degradation Machinery. Analytical Chemistry 90, 794-800
128. Chen, Y., Cong, Y., Quan, B. Y., Lan, T., Chu, X. Y., Ye, Z., Hou, X. M., and Wang, C. (2017) Chemoproteomic profiling of targets of lipid-derived electrophiles by bioorthogonal aminooxy probe. Redox Biology 12, 712-718
129. Bicker, K. L., Subramanian, V., Chumanevich, A. A., Hofseth, L. J., and Thompson, P. R. (2012) Seeing Citrulline: Development of a Phenylglyoxal-Based Probe To Visualize Protein Citrullination. Journal of the American Chemical Society 134, 17015-17018
130. Lewallen, D. M., Bicker, K. L., Subramanian, V., Clancy, K. W., Slade, D. J., Martell, J., Dreyton, C. J., Sokolove, J., Weerapana, E., and Thompson, P. R. (2015) Chemical Proteomic Platform To Identify Citrullinated Proteins. Acs Chemical Biology 10, 2520-2528
131. Nemmara, V. V., and Thompson, P. R. (2019) Development of Activity-Based Proteomic Probes for Protein Citrullination. Activity-Based Protein Profiling 420, 233-251
132. Altelaar, A. F. M., Munoz, J., and Heck, A. J. R. (2013) Next-generation proteomics: towards an integrative view of proteome dynamics. Nature Reviews Genetics 14, 35-48
133. Mocciaro, A., and Rape, M. (2012) Emerging regulatory mechanisms in ubiquitin-dependent cell cycle control. Journal of Cell Science 125, 255-263
134. Mertins, P., Qiao, J. W., Patel, J., Udeshi, N. D., Clauser, K. R., Mani, D. R., Burgess, M. W., Gillette, M. A., Jaffe, J. D., and Carr, S. A. (2013) Integrated proteomic analysis of post-translational modifications by serial enrichment. Nature Methods 10, 634-+
135. Xie, X. S., Shah, S. M., Holtz, A. A., Rose, A. O., Basisty, N. H., and Schilling, B. R. (2020) Simultaneous Affinity Enrichment of Two Post-Translational Modifications for Quantification and Site Localization. Jove-Journal of Visualized Experiments
136. Lima, B., Forrester, M. T., Hess, D. T., and Stamler, J. S. (2010) S-Nitrosylation in Cardiovascular Signaling. Circulation Research 106, 633-646.

The invention claimed is:

1. A mass spectrometry tagging reagent comprising a compound having:

a) an isobaric tag comprising a reporter group having at least one atom that is optionally isotopically labeled and a balancing group also having at least one atom that is optionally isotopically labeled;

b) an enrichment moiety; and c) a conjugation moiety able to bind to a molecule of interest, wherein the tagging reagent comprises the formula:

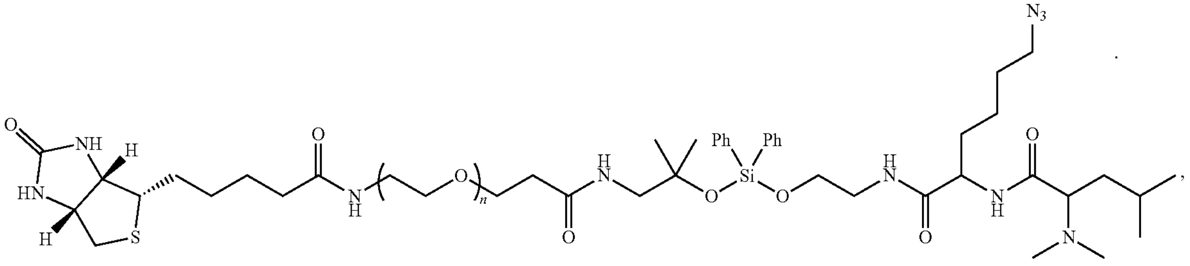

where n is an integer ranging from 0 to 10,

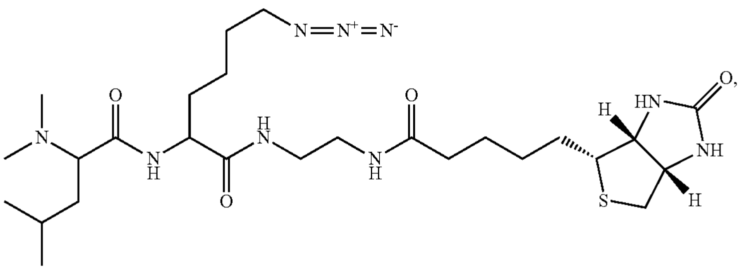

-continued
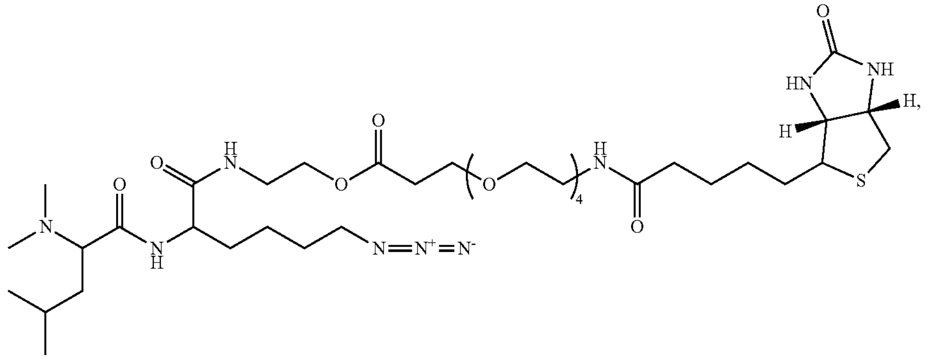
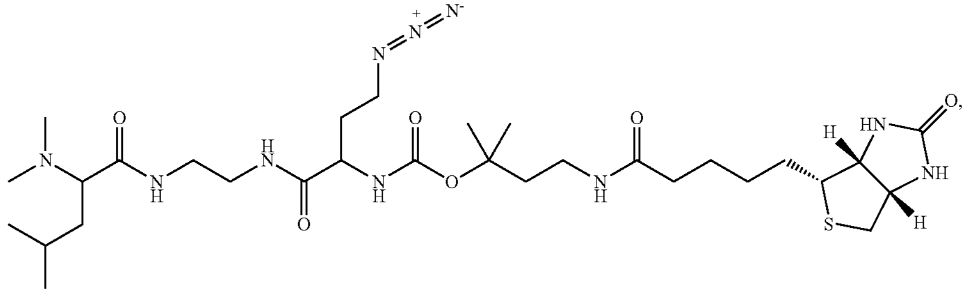
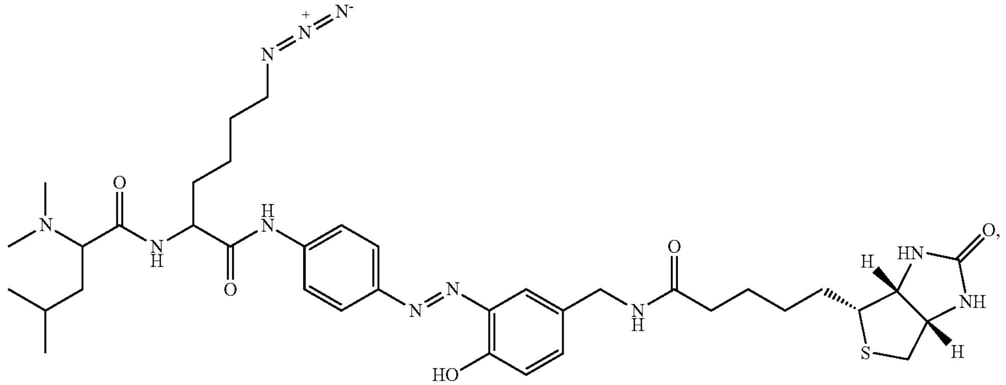
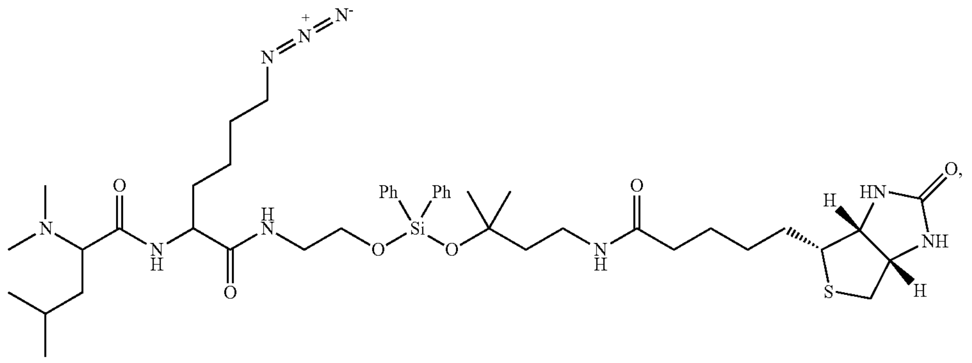
or

-continued

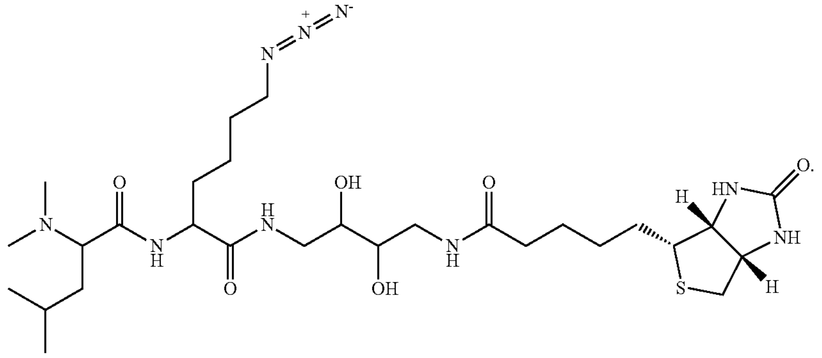

2. The tagging reagent of claim 1, wherein one or more carbon atoms in the reporter group are $^{13}C$, one or more oxygen atoms are $^{18}O$, one or more nitrogen atoms in the reporter group $^{15}N$, or combinations thereof.

3. The tagging reagent of claim 1, wherein the conjugation moiety is able to bind to a terminal alkyne or dibenzocyclooctyne (DBCO) group having the formula:

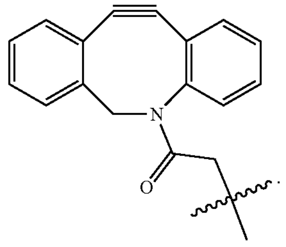 [SMILES: *CC(=O)N1Cc2ccccc2C#Cc2ccccc21]

4. A method of analyzing a molecule, said method comprising the steps of:

a) providing the molecule;

b) labeling the molecule with a compound having:

i) an isobaric tag comprising a reporter group having at least one atom that is optionally isotopically labeled and a balancing group also having at least one atom that is optionally isotopically labeled;

ii) an enrichment moiety; and iii) a conjugation moiety able to bind to a molecule of interest;

c) purifying or enriching the labeled molecule;

d) fragmenting the purified molecule to generate an immonium ion from the reporter group of the purified molecule; and e) detecting and analyzing fragments of the purified molecule, wherein the compound comprises the formula:

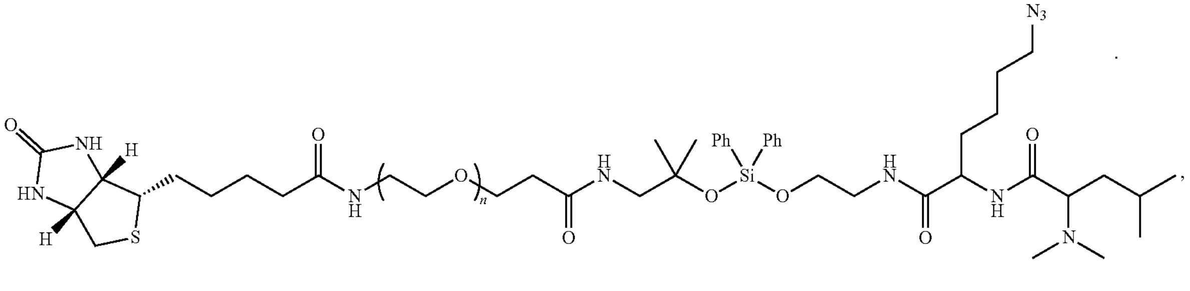

where n is an integer ranging from 0 to 10,

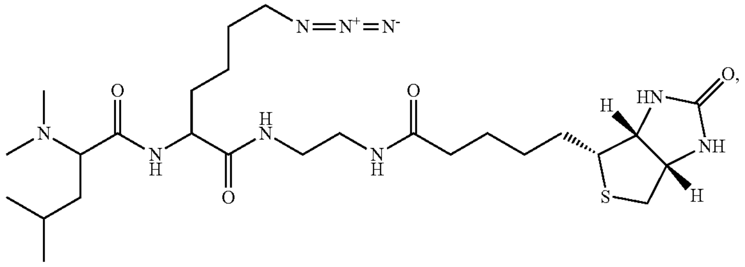

-continued
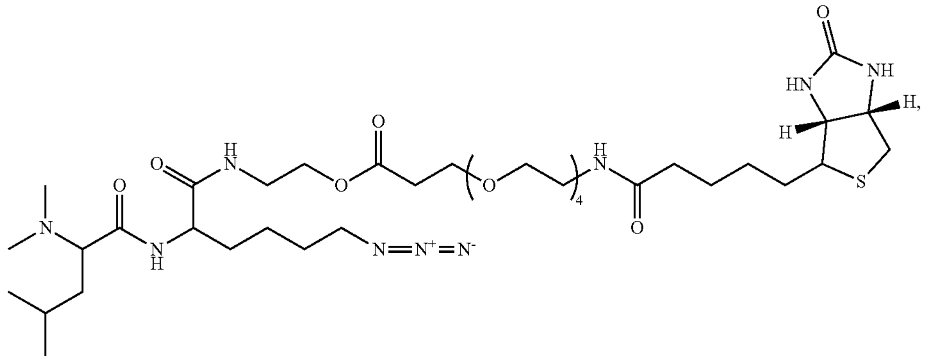
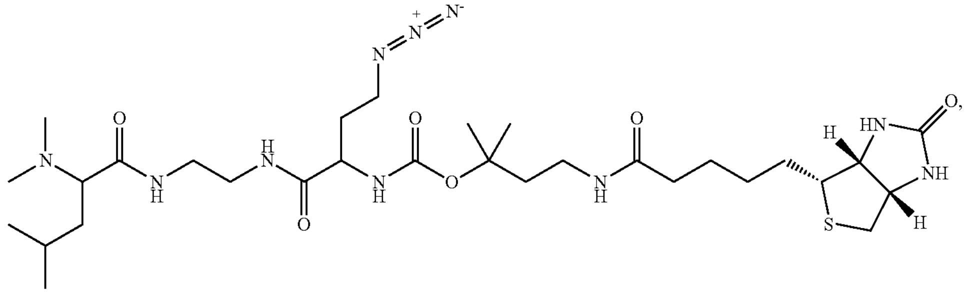
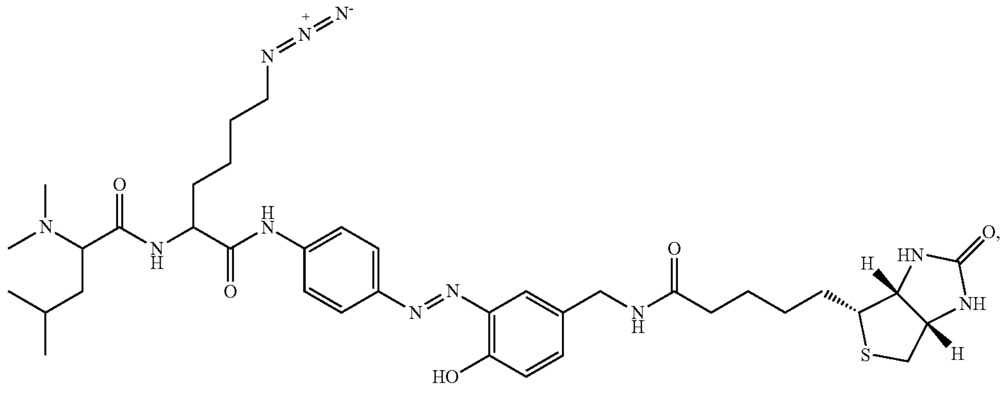
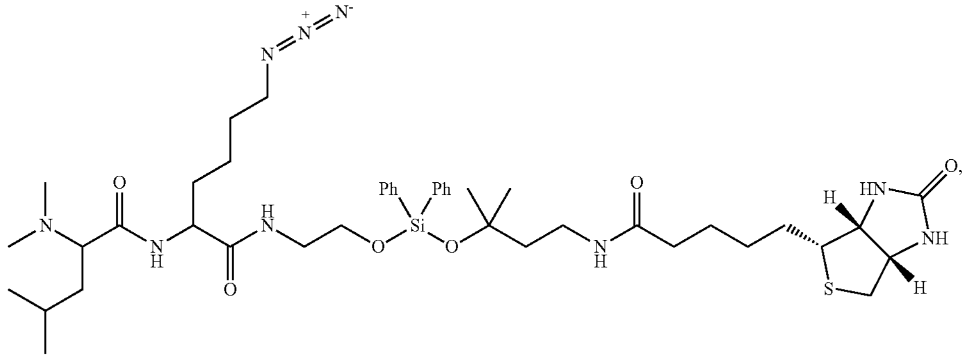
or

-continued

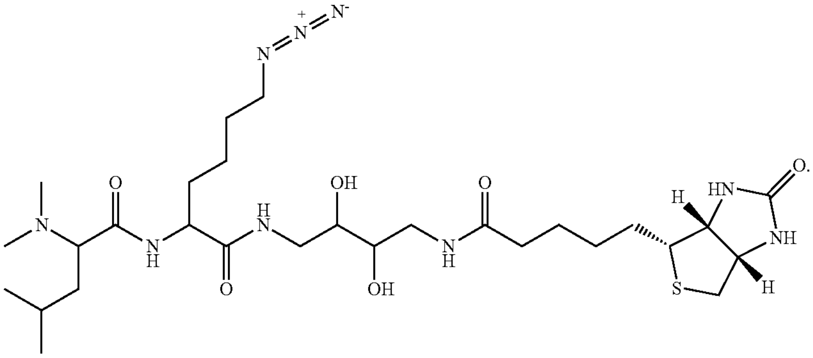

5. The method of claim 4, wherein the molecule is a peptide or protein comprising one or more post-translational modifications (PTMs).

6. The method of claim 5, wherein labeling the molecule comprises the step of reacting the modification site of the peptide or protein to contain a terminal alkyne or DBCO group able to react with an azide group of the labeling compound.

7. The method of claim 4, wherein labeling the molecule comprises the step of reacting the conjugation moiety to an alkynyl group of the molecule.

8. A mass spectrometry tagging reagent comprising a compound having:

a) an isobaric tag comprising a reporter group having at least one atom that is optionally isotopically labeled and a balancing group also having at least one atom that is optionally isotopically labeled;

b) an enrichment moiety; and c) a conjugation moiety able to bind to a molecule of interest, wherein the tagging reagent comprises the formula:

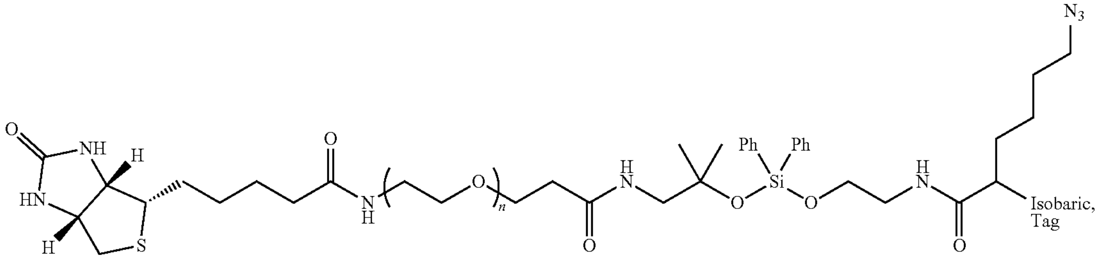

where n is an integer ranging from 0 to 10,

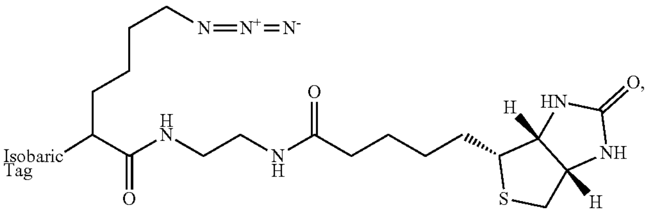

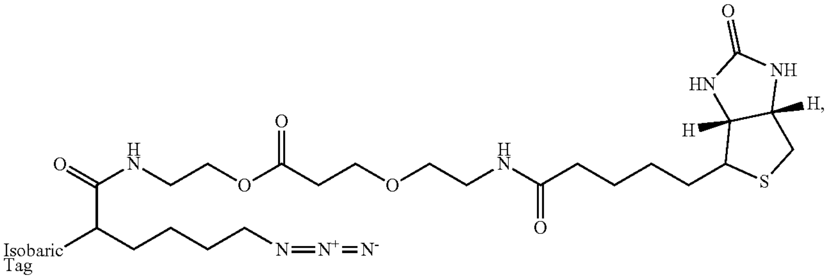

-continued
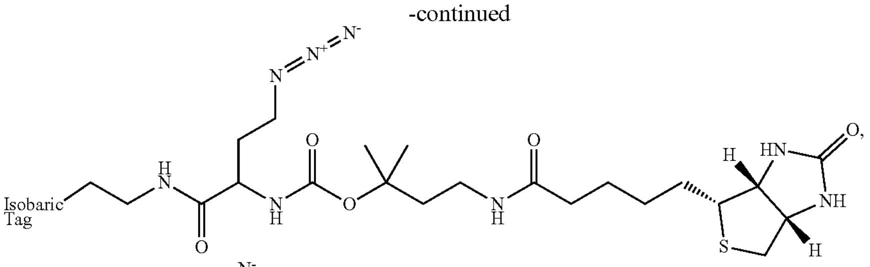
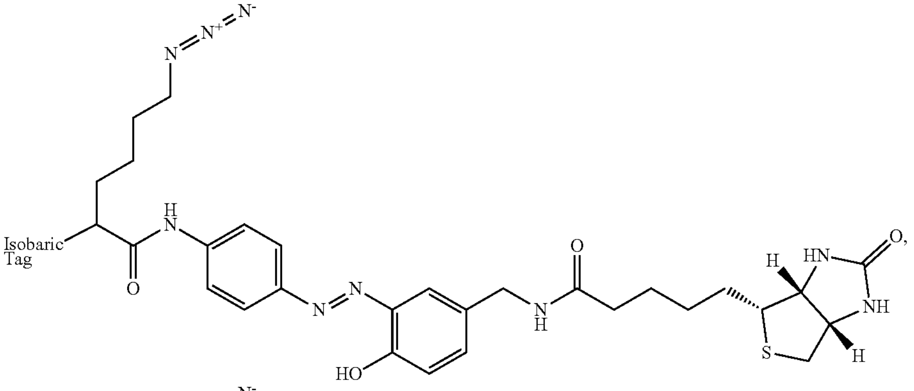
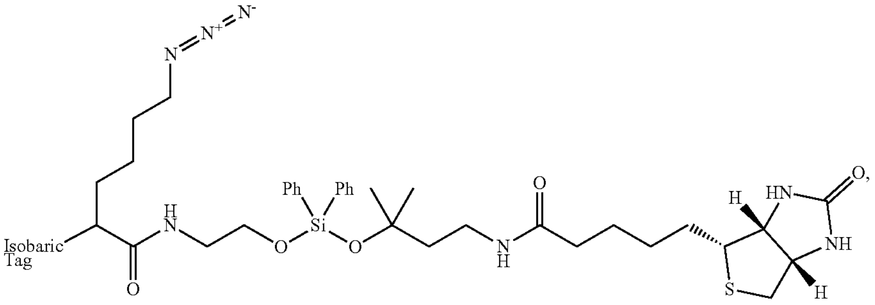
or
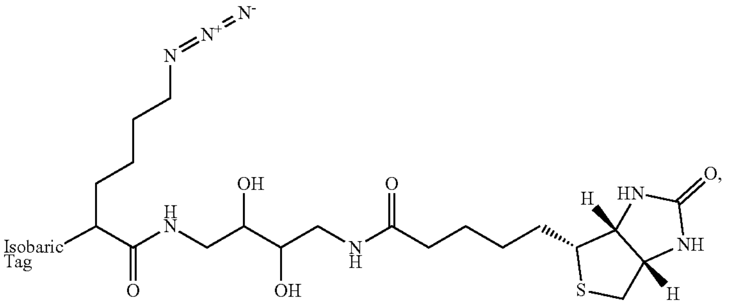
wherein the isobaric tag comprises N,N-dimethyl leucine (DiLeu); N,N-dimethyl isoleucine (Di Ile); N,N-dimethyl alanine (DiAla); N,N-dimethyl glycine (DiGly); N,N-dimethyl valine (DiVal); N,N-dimethyl histidine (DiHis); N,N-dimethyl phenylalanine (DiPhe); N,N-dimethyl tryptophan (DiTrp); N,N-dimethyl lysine (DiLys), or N,N-dimethyl tyrosine (DiTyr).
* * * * *